US009965585B2

(12) United States Patent
Lo et al.

(10) Patent No.: US 9,965,585 B2
(45) Date of Patent: May 8, 2018

(54) DETECTION OF GENETIC OR MOLECULAR ABERRATIONS ASSOCIATED WITH CANCER

(71) Applicant: The Chinese University of Hong Kong, Sha Tin, New Territories (CN)

(72) Inventors: Yuk-Ming Dennis Lo, Homantin (CN); Kwan Chee Chan, Mei Foo Sun Chuen (CN); Rossa Wai Kwun Chiu, Sha Tin (CN); Peiyong Jiang, Sha Tin (CN)

(73) Assignee: The Chinese University of Hong Kong, Shatin (HK)

(*) Notice: Subject to any disclaimer, the term of this patent is extended or adjusted under 35 U.S.C. 154(b) by 0 days. days.

(21) Appl. No.: 14/255,415

(22) Filed: Apr. 17, 2014

(65) Prior Publication Data

US 2014/0227699 A1 Aug. 14, 2014

Related U.S. Application Data

(62) Division of application No. 13/308,473, filed on Nov. 30, 2011, now Pat. No. 8,741,811.

(Continued)

(51) Int. Cl.

*G06F 19/22* (2011.01)
*C12Q 1/68* (2018.01)
*G06F 19/18* (2011.01)

(52) U.S. Cl.

CPC .......... *G06F 19/22* (2013.01); *C12Q 1/6809* (2013.01); *C12Q 1/6869* (2013.01);

(Continued)

(58) Field of Classification Search

None

See application file for complete search history.

(56) References Cited

U.S. PATENT DOCUMENTS 5,952,170 A 9/1999 Stroun et al.
7,163,789 B2 1/2007 Chen et al.

(Continued)

FOREIGN PATENT DOCUMENTS

CA 2786564 A1 7/2011
CN 101849236 A 9/2010

(Continued)

OTHER PUBLICATIONS

Conrads et al., Expert Rev. Mol. Diagn. 3(4), 2003.*

(Continued)

*Primary Examiner* — Larry D Riggs, II
(74) *Attorney, Agent, or Firm* — Kilpatrick Townsend & Stockton LLP; David B. Raczkowski

(57) ABSTRACT

Systems, apparatus, and methods are provided for determining genetic or molecular aberrations in a biological sample. Biological samples including cell-free DNA fragments are analyzed to identify imbalances in chromosomal regions, e.g., due to deletions and/or amplifications in a tumor. Multiple loci are used for each chromosomal region. Such imbalances can be used to diagnose (screen) a patient for cancer, as well as prognosticate a patient with cancer, or to detect the presence or to monitor the progress of a premalignant condition in a patient. Severity of an imbalance and the number of regions exhibiting an imbalance can be used. A systematic analysis of non-overlapping genomic segments can provide a general screening tool. A patient can be tested over time to track severity of each of one or more chromosomal regions and a number of chromosomal regions to enable screening and prognosticating, as well as monitoring of progress (e.g. after treatment).

27 Claims, 29 Drawing Sheets

Related U.S. Application Data

(60) Provisional application No. 61/418,391, filed on Nov. 30, 2010, provisional application No. 61/529,877, filed on Aug. 31, 2011.

(52) U.S. Cl.
CPC .......... *C12Q 1/6886* (2013.01); *G06F 19/18* (2013.01); *C12Q 2600/156* (2013.01); *C12Q 2600/172* (2013.01)

(56) References Cited

U.S. PATENT DOCUMENTS

| | | | | |
|---|---|---|---|---|
| 7,700,286 | B2 | 4/2010 | Stroun et al. | |
| 7,704,687 | B2 | 4/2010 | Wang et al. | |
| RE44,596 | E | 11/2013 | Stroun et al. | |
| 2003/0064371 | A1 | 4/2003 | Sidransky | |
| 2009/0029377 | A1 | 1/2009 | Lo et al. | |
| 2009/0087847 | A1 | 4/2009 | Lo et al. | |
| 2010/0041048 | A1 | 2/2010 | Diehl et al. | |
| 2010/0136560 | A1 | 6/2010 | Vogelstein et al. | |
| 2010/0227768 | A1 | 9/2010 | Wigler et al. | |
| 2011/0245085 | A1 * | 10/2011 | Rava | C12Q 1/6806 506/2 |
| 2012/0034685 | A1 * | 2/2012 | Sparks | C12Q 1/6827 435/287.2 |
| 2012/0059670 | A1 * | 3/2012 | Sanborn | G06Q 50/24 705/3 |

FOREIGN PATENT DOCUMENTS

| | | | | |
|---|---|---|---|---|
| EA | 201000231 | A1 | 6/2010 | |
| EA | 201200690 | A1 | 5/2013 | |
| EA | 201201551 | A1 | 8/2013 | |
| JP | 2010534068 | A | 11/2010 | |
| WO | 98/08980 | A1 | 3/1998 | |
| WO | WO 2008016374 | A2 * | 2/2008 | C12Q 1/6886 |
| WO | 2009/013492 | A1 | 1/2009 | |
| WO | 2009/013496 | A1 | 1/2009 | |
| WO | 2011/057094 | A1 | 5/2011 | |
| WO | 2011/103236 | A2 | 8/2011 | |

OTHER PUBLICATIONS

Rifkin et al., SIAM Review, 45(4), 706-723, 2003.*
Su et al., Cancer Research 61, 7388-7393, Oct. 15, 2001.*
European Search Report dated May 8, 2014 in European Patent Application No. EP11845367.9, 7 pages.
Office Action (English Translation) dated Mar. 18, 2015 in Eurasian Patent Application No. 201300649, 2 pages.
Laframboise, et al., "Allele-Specific Amplification in Cancer Revealed by SNP Array Analysis," PLoS Computational Biology, 2005, vol. 1, No. 6, e65, 11 pages.
Thierry, et al., "Origin and Quantification of Circulating DNA in Mice with Human Colorectal Cancer Xenografts," Nucleic Acids Research, 2010, vol. 38, No. 18, pp. 6159-6175.
Zhao, et al., "Homozygous Deletions and Chromosome Amplifications in Human Lung Carcinomas Revealed by Single Nucleotide Polymorphism Array Analysis," Cancer Research, 2005, vol. 65, No. 13, pp. 5561-5570.
Taback, B., et al., "Prognostic Significance of Circulating Microsatellite Markers in the Plasma of Melanoma Patients", Cancer Research, Aug. 1, 2001, vol. 61, pp. 5723-5726.
International Application No. PCT/AU2011/001562, International Search Report and Written Opinion dated Feb. 17, 2012, 8 Pages.
Liao, Gary J.W., et al., "Targeted Massively Parallel Sequencing of Maternal Plasma DNA Permits Efficient and Unbiased Detection of Fetal Alleles;" 2011; Clinical Chemistry; vol. 57; No. 1; pp. 92-101.
Lun, Fiona M. F., et al., "Noninvasive prenatal diagnosis of monogenic diseases by digital size selection and relative mutation dosage on DNA in maternal plasma;" Dec. 16, 2008; PNAS; vol. 105; No. 50; pp. 19920-19925.
Schwarzenbach, Heidi, et al., "Cell-free nucleic acids as biomarkers in cancer patients;" Jun. 2011; Nature; vol. 11, pp. 426-437.
Prokunina-Olsson, Ludmilla and Chanock, Stephen J., "Cancer Sequencing Gets a Little More Personal;" Feb. 24, 2010; www.ScienceTranslationalMedicine.org; vol. 2; Issue 20; pp. 1-3.
Mueller, Imke, et al., "Identification of Loss of Heterozygosity on Circulating Free DNA in Peripheral Blood of Prostate Cancer Patients: Potential and Technical Improvements;" 2008; Clinical Chemistry; vol. 54; No. 4; pp. 688-696.
Psifidi, Androniki, et al., "Novel Quantitative Real-Time LCR for the Sensitive Detection of SNP Frequencies in Pooled DNA: Method Development, Evaluation and Application;" Jan. 1, 2011; PLoS ONE; vol. 6; Issue 1; pp. 1-11.
Salani, Ritu, et al., "Benign Effusions Length in Cell-Free DNA Distinguish Malignant versus Measurement of Cyclin E Genomic Copy Number and Strand;" Published online Oct. 1, 2007; Clin Cancer Res 2007; vol. 13; pp. 5805-5809.
Weber, Axel, et al., "Detection of human tumor cells by amplicon fusion site polymerase chain reaction (AFS-PCR);" Feb. 2011; The Journal of Clinical Investigation; vol. 121; No. 2; 545-553.
Chang, Hsueh-Wei, et al., "Assessment of Plasma DNA Levels, Allelic Imbalance, and CA 125 as Diagnostic Tests for Cancer;" Nov. 20, 2002; Journal of the National Cancer Institute; vol. 94; No. 22; pp. 1697-1703.
Hanlon, Katy, et al., "Evaluation of 13q14 Status in Multiple Myeloma by Digital Single Nucleotide Polymorphism Technology;" Sep. 2009; Journal of Molecular Diagnostics; vol. 11; No. 5; pp. 450-457.
Qin, Jian, et al., "Studying copy number variations using a nanofluidic platform;" 2008; Nucleic Acids Research; vol. 36; No. 18; pp. 1-8.
Shaw, Jacqueline A., et al., "Genomic analysis of circulating cell free DNA infers breast cancer dormancy;" published online Oct. 11, 2011; Genome Res; 13 pages.
Snyder, Thomas M., "Universal noninvasive detection of solid organ transplant rejection;" Apr. 12, 2011; PNAS; vol. 108; No. 15; pp. 6229-6234.
Yung, Tony, K.F., et al., "Single-Molecule Detection of Epidermal Growth Factor Receptor Mutations in Plasma by Microfluidics Digital PCR in Non-Small Cell Lung Cancer Patients;" Mar. 15, 2009; Clin Cancer Res 2009; vol. 15, No. 6; pp. 2076-2084.
Diehl, Frank, et al., "Circulating mutant DNA to assess tumor dynamics;" published online Jul. 31, 2008; Nature Medicine; pp. 1-6.
Diehl, Frank, et al., "Detection and quantification of mutations in the plasma of patients with colorectal tumors;" Nov. 8, 2005; PNAS; vol. 102; No. 45; pp. 16368-16373.
Jung, Klaus, et al., "Cell-free DNA in the blood as a solid tumor biomarker—A critical appraisal of the literature;" 2010; Clinica Chimica Acta; vol. 411; pp. 1611-1624.
Leary, Rebecca J., et al., "Development of Personalized Tumor Biomarkers Using Massively Parallel Sequencing;" Feb. 24, 2010; www.ScienceTranslationalMedicine.org; vol. 2; Issue 20; 8 pages.
Wang, Tian-Li, et al., "Digital Karyotyping," PNAS, Dec. 10, 2002, vol. 99, No. 25, pp. 16156-16161.
Beck, Julia, et al., "Profile of the Circulating DNA in Apparently Healthy Individuals," Clinical Chemistry, 2009, vol. 55, No. 4, pp. 730-738.
Beck, Julia, et al., "Next Generation Sequencing of Serum Circulating Nucleic Acids from Patients with Invasive Ductal Breast Cancer Reveals Differences to Health and Nonmalignant Controls," American Association for Cancer Research, 2010, pp. 335-342, [online], retrieved from the internet URL: www.aacrjournals.org.
McDermott, M. B., et al., "Genomics and the Continuum of Cancer Care," The New England Journal of Medicine, Jan. 27, 2011, pp. 340-350, [online], retrieved from the internet URL: nejm.org.
Stratton, Michael, R., "Exploring the Genomes of Cancer Cells: Progress and Promise," Science, Mar. 25, 2011, pp. 1553-1558, [online], retrieved from the internet URL: www.sciencemag.org.
Navin, Nicholas, et al., "Future Medical Applications of Single-Cell Sequencing in Cancer," Genome Medicine, 2011, vol. 3, No. 31, 12 pages.

(56) References Cited

OTHER PUBLICATIONS

Navin, Nicholas, et al., "Tumour Evolution Inferred by Single-Cell Sequencing," Nature, Apr. 7, 2011, vol. 472, 6 pages.
Deligezer, Ugur et al.; "Size distribution of circulating cell-free DNA in sera of breast cancer patients in the course of adjuvant chemotherapy"; Clinical Chemistry and Laboratory Medicine; 2008; vol. 46, Issue 3; pp. 311-317.
Patent Examination Report No. 1 dated Nov. 16, 2016 in AU Patent Application No. 2015205935. 6 pages.
English translation of Office Action dated Jul. 12, 2016 in JP Patent Application 2013-541152. 2 pages.
English translation of Office Action dated Aug. 25, 2017 in KR Patent Application No. 2013-7016780. 5 pages.
Sun, Miao et al.; "Copy-Number Mutations on Chromosome 17q24. 2-q24.3 in Congenital Generalized Hypertrichosis Terminalis with or without Gingival Hyperplasia"; The American Journal of Human Genetics; Jun. 12, 2009; vol. 84; pp. 807-813.
Extended European Search Report dated Oct. 9, 2017 in EP Patent Application No. 17168020.0. 10 pages.
Urbanova, Marketa et al.; "Circulating nucleic acids as a new diagnostic tool"; Cellular and Molecular Biology Letters; published online Feb. 25, 2010; vol. 15, DOI: 10.2478/s11658-010-0004-6; pp. 242-259.
Office Action dated Oct. 24, 2017 in CA Patent Application No. 2,817,370. 5 pages.

* cited by examiner 310 320 330 340

| Cancer type | Gain | Loss | Reference |
|---|---|---|---|
| Thyroid carcer | 7p, 8q, and 9q | 22 | Hemmer et al. Am J Pathol, 1999;154:1539-47. |
| Gastric cancer | 2q37, 3p21, 5q34-35,7q34-36, 11q13, 11q23-25, 12q24, 15q23-25, 17q21-25, and 20q12-13 | 4q, 13q, 5q, 6q, and 18p | Noguchi et al.Am J ClinPathol 2001; 115:828-34 |
| Prostate cancer | 1q32, 3q26, 4q26, 7q21, 8q22, 9q33, 17q25, and Xq21 | 2q22, 4q27–4q28, 5q15, 6q15, 8p21, 10q23, 12p13, 13q21, 15q23, 16q22, and 18q21–22 | Sun et al. Prostate 2007;67:692-700. |
| Small cell lung cancer | 3q26-29, 5p12-13, and 8q23-24 | 3p13-14,4q32-35, 5q32-35,8p21-22,10q25, 13q13-14,and 17p12-13 | Balsara et al. Oncogene 2002;21:6877-83. |
| Non small cell lung cancer | 1q31, 3q25-27, 5p13-14, and 8q23-24 | 31p21,8p22, 9p21-22,13q22, and 17p12-13 | Balsara et al. Oncogene 2002;21:6877-83. |
| Nasopharyngeal carcinoma | 1p34, 3q26, 6q25, and 3q26 | 3p, 9p, 9q, 11q, 13q, and14q | Lo et al. Semin Cancer Biol 2002;12:451-62 |
| Bladder cancer | 1q, 5p, 6p, 8q, 11q, 17q, and 20q | 3p, 4q, 4q, 6q, 8p, 9p, and 18q | El-Rifai et al. Am J Pathol 2000;156:871-8 |
| Colorectal cancer | 13q and 20q | 4q and 18q | De Angelis et al. Int J Colorectal Dis 2001;16:38-45. |
| Head and neck cancer | 3q26 and 11q13 | 3p, 9p, and 17p | Smeets et al. Oncogene 2006;25:2558-64 |
| Melanoma | 1q, 2, 6p, 7, 8, 17, and 20 | 6q, 8p, 9, and 10 | Bastian et al. Cancer Res 1998;58:2170-5. |
| Lymphoma | 1q, 3, 6p, 7, 11, 12, 18, and X | 1p, 8p, and X | Monni et al. Blood 1996;87:5269-78 |

| Fractional concentration of cancer-derived DNA 1510 | Estimated no. of molecules required per segment 1520 | Size of each segment (kb) 1530 | Total no. of molecules to be analyzed for the whole genome (million) 1540 |
|---|---|---|---|
| 50% | 950 | 100 | 28.5 |
| | | 1,000 | 2.85 |
| | | 5,000 | 0.570 |
| | | 10,000 | 0.285 |
| 25% | 3,800 | 100 | 114 |
| | | 1,000 | 11.4 |
| | | 5,000 | 2.28 |
| | | 10,000 | 1.14 |
| 12.5% | 15,000 | 100 | 450 |
| | | 1,000 | 45 |
| | | 5,000 | 9 |
| | | 10,000 | 4.5 |
| 6.3% | 60,000 | 100 | 1,800 |
| | | 1,000 | 180 |
| | | 5,000 | 36 |
| | | 10,000 | 18 |
| 3.2% | 240,000 | 100 | 7,200 |
| | | 1,000 | 720 |
| | | 5,000 | 144 |
| | | 10,000 | 72 |

FIG. 15

```
                          SEQUENCE LISTING


<160> NUMBER OF SEQ ID NOS: 2

<210> SEQ ID NO 1
<211> LENGTH: 11
<212> TYPE: DNA
<213> ORGANISM: Artificial Sequence
<220> FEATURE:
<223> OTHER INFORMATION: synthetic nuclotide - Hap I

<400> SEQUENCE: 1

atgcctgaat c                                                          11


<210> SEQ ID NO 2
<211> LENGTH: 11
<212> TYPE: DNA
<213> ORGANISM: Artificial Sequence
<220> FEATURE:
<223> OTHER INFORMATION: synthetic nuclotide - Hap II

<400> SEQUENCE: 2

tacgtcatgc t                                                          11
```

DETECTION OF GENETIC OR MOLECULAR ABERRATIONS ASSOCIATED WITH CANCER

CROSS-REFERENCES TO RELATED APPLICATIONS

The present application is a divisional application of U.S. patent application Ser. No. 13/308,473, entitled "DETECTION OF GENETIC OR MOLECULAR ABERRATIONS ASSOCIATED WITH CANCER" filed Nov. 30, 2011, which claims priority from and is a non provisional application of U.S. Provisional Application No. 61/418,391, entitled "DETECTION OF GENETIC ABERRATIONS ASSOCIATED WITH CANCER" filed Nov. 30, 2010, and U.S. Provisional Application No. 61/529,877, entitled "DETECTION OF GENETIC OR MOLECULAR ABERRATIONS ASSOCIATED WITH CANCER" filed Aug. 31, 2011, the entire contents of which are herein incorporated by reference for all purposes.

This application is related to commonly owned U.S. patent application Ser. No. 12/940,992 (U.S. Publication 2011/0276277) entitled "Size-Based Genomic Analysis" by Lo et al., filed Nov. 5, 2010, and U.S. patent application Ser. No. 12/940,993 (U.S. Publication 2011/0105353) entitled "Fetal Genomic Analysis From A Maternal Biological Sample" by Lo et al., filed Nov. 5, 2010, the disclosures of which is incorporated by reference in its entirety.

BACKGROUND

Cancer is a common disease that affects many people. Often cancer is not identified until severe symptoms manifest. For common types of cancer, there are screening techniques to identify patients who may have cancer. But, such techniques are often unreliable or subject a patient to radiation. For many other types of cancers, there are no effective screening techniques.

Loss of heterozygosity (LOH) has been detected for a particular locus in the circulating DNA of patients suffering from lung, and head and neck cancers (Chen X Q, et al. Nat Med 1996; 2: 1033-5; Nawroz H, et al. Nat Med 1996; 2: 1035-7). However, such techniques have been hindered by a relative small amount of LOH that has been detectable from examining a particular locus. Even when using digital PCR, these methods still suffer from an inability to detect small amounts of LOH. Moreover, such techniques have still been limited to investigating a particular locus that is known to occur in a specific type of cancer. Thus, a screening for cancer in general has not been possible or effective.

Besides screening for an existence of cancer, current techniques are also lacking for providing a prognosis of a patient with cancer and for monitoring the effects of treatment (e.g. recovery after surgery or chemotherapy or immunotherapy or targeted therapy). Such techniques are often expensive (e.g. imaging techniques), inaccurate, ineffective, insensitive or may subject the patient to the radiation used for imaging techniques.

Accordingly, it is desirable to provide new techniques for screening, prognosticating, and monitoring a patient for cancer.

BRIEF SUMMARY

Embodiments provide systems, apparatus, and methods for determining genetic aberrations associated with cancer. Biological samples including cell-free DNA fragments are analyzed to identify imbalances in chromosomal regions, e.g., due to deletions and/or amplifications in a tumor. Using a chromosomal region with multiple loci can allow for greater efficiency and/or accuracy. Such imbalances can then be used to diagnose or screen a patient for cancer, as well as prognosticate a patient with cancer. The severity of an imbalance as well as the number of regions exhibiting an imbalance can be used. Additionally, a patient can be tested over time to track severity of each of one or more chromosomal regions and a number of chromosomal regions to enable screening and prognosticating, as well as monitoring of progress (e.g. after treatment).

According to one embodiment, a method of analyzing a biological sample of an organism for chromosomal deletions or amplifications associated with cancer is provided. The biological sample includes nucleic acid molecules originating from normal cells and potentially from cells associated with cancer. At least some of the nucleic acid molecules are cell-free in the sample. First and second haplotypes are determined for normal cells of the organism at a first chromosomal region. The first chromosomal region including a first plurality of heterozygous loci. Each of a plurality of the nucleic acid molecules in the sample have a location in a reference genome of the organism identified and have a respective allele determined. The locations and determined alleles are used to determine a first group of nucleic acid molecules from the first haplotype and a second group from the second haplotype. A computer system calculates a first value of the first group and a second value of the second group. Each value defined a property of the respective group of nucleic acid molecules (e.g. an average size or number of molecules in the group). The first value is compared to the second value to determine a classification of whether the first chromosomal region exhibits a deletion or an amplification in any cells associated with cancer.

According to another embodiment, a method of analyzing a biological sample of an organism is provided. The biological sample includes nucleic acid molecules originating from normal cells and potentially from cells associated with cancer. At least some of the nucleic acid molecules are cell-free in the sample. A plurality of non-overlapping chromosomal regions of the organism are identified. Each chromosomal region includes a plurality of loci. Each of a plurality of the nucleic acid molecules in the sample have a location in a reference genome of the organism identified. For each chromosomal region, a respective group of nucleic acid molecules are identified as being from the chromosomal region based on the identified locations. Each respective group includes at least one nucleic acid molecule located at each of the plurality of loci of the chromosomal region. A computer system calculates a respective value of the respective group, where the respective value defines a property of the nucleic acid molecules of the respective group. The respective value is compared to a reference value to determine a classification of whether the chromosomal region exhibits a deletion or an amplification. An amount of chromosomal regions classified as exhibiting a deletion or amplification is then determined.

According to another embodiment, a method is provided for determining a progress of chromosomal aberrations in an organism using biological samples including nucleic acid molecules originating from normal cells and potentially from cells associated with cancer. At least some of the nucleic acid molecules are cell-free in the biological samples. One or more non-overlapping chromosomal regions are identified for a reference genome of the organism. Each chromosomal region includes a plurality of loci. Samples taken from the organism at different times are analyzed to determine the progress. For a sample, each of a plurality of the nucleic acid molecules in the sample have a location in a reference genome of the organism identified. For each chromosomal region, a respective group of nucleic acid molecules are identified as being from the chromosomal region based on the identified locations. The respective group including at least one nucleic acid molecule located at each of the plurality of loci of the chromosomal region. A computer system calculates a respective value of the respective group of nucleic acid molecules. The respective value defines a property of the nucleic acid molecules of the respective group. The respective value is compared to a reference value to determine a classification of whether the first chromosomal region exhibits a deletion or an amplification. Then, the classifications of each of the chromosomal regions at the plurality of times are used to determine the progress of the chromosomal aberrations in the organism.

Other embodiments of the invention are directed to systems, portable consumer devices, and computer readable media associated with methods described herein.

A better understanding of the nature and advantages of the present invention may be gained with reference to the following detailed description and the accompanying drawings.

BRIEF DESCRIPTION OF THE DRAWINGS

FIG. 3 shows a table 300 illustrating different types of cancers and associated regions and their corresponding aberrations.

FIG. 15 shows a table 1500 illustrating the depth required for various numbers of segments and fractional concentration of tumor-derived fragments according to embodiments of the present invention. FIG. 15 provides an estimation of the number of molecules to be analyzed for different percentage of fractional concentration of cancer-derived DNA in a sample.

DEFINITIONS

Figure 1:
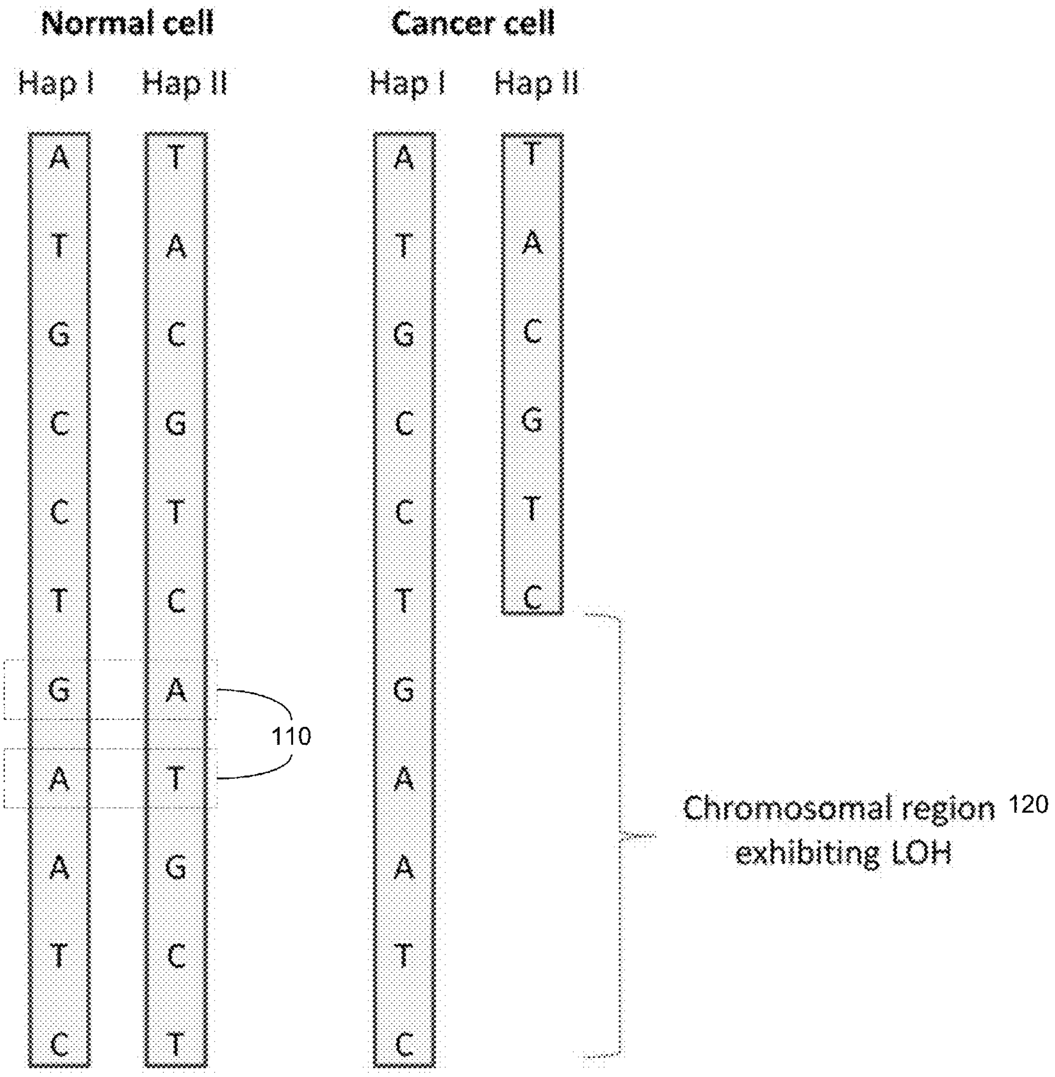
FIG. 1 illustrates a chromosomal region of a cancer cell exhibiting an aberration of a deletion. (Hap I (SEQ ID NO:1) and Hap II (SEQ ID NO:2))

The term "biological sample" as used herein refers to any sample that is taken from a subject (e.g., a human, a person with cancer, a person suspected of having cancer, or other orgnanisms) and contains one or more nucleic acid molecule(s) of interest.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), copy number variants, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid encompasses, but is not limited to: gene, cDNA, mRNA, small noncoding RNA, micro RNA (miRNA), Piwi-interacting RNA, and short hairpin RNA (shRNA) encoded by a gene or locus.

The term "gene" means the segment of DNA involved in producing a polypeptide chain or transcribed RNA product. It may include regions preceding and following the coding region (leader and trailer) as well as intervening sequences (introns) between individual coding segments (exons).

The term "clinically relevant nucleic acid sequence" or "clinically relevant chromosomal region" (or region/segment being tested) as used herein can refer to a polynucleotide sequence corresponding to a segment of a larger genomic sequence whose potential imbalance is being tested or to the larger genomic sequence itself. Examples include genomic segments that are or potentially are deleted or amplified (including simple duplication), or to a larger region that includes the subregion of the segment. In some embodiments, multiple clinically relevant nucleic acid sequences, or equivalently multiple markers of the clinically relevant nucleic acid sequence, can be used to provide data for detecting an imbalance in a region. For instance, data from five non-consecutive sequences on a chromosome can be used in an additive fashion for the determination of a possible imbalance, effectively reducing the needed sample volume to 1/5.

The term "reference nucleic acid sequence" or "reference chromosomal region" as used herein refers to a nucleic acid sequence whose quantitative profile or size distribution is used to compare against the test region. Examples of a reference nucleic acid sequence include a chromosomal region that does not include a deletion or amplification, the entire genome (e.g. via a normalization by total sequenced tag counts), a region from one or more samples known to be normal (which could be the same region for the sample being tested), or a particular haplotype of a chromosomal region. Such reference nucleic acid sequences can either exist endogenously in the sample, or added exogenously during sample processing or analysis. In some embodiments, the reference chromosomal region demonstrates a size profile that is representative of a healthy state without disease. In yet other embodiments, the reference chromosomal region demonstrates a quantitative profile that is representative of a healthy state without disease.

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

As used herein, the term "locus" or its plural form "loci" is a location or address of any length of nucleotides (or base pairs) which may have a variation across genomes.

The term "sequence imbalance" or "aberration" as used herein means any significant deviation as defined by at least one cutoff value in a quantity of the clinically relevant chromosomal region from a reference quantity. A sequence imbalance can include chromosome dosage imbalance, allelic imbalance, mutation dosage imbalance, copy number imbalance, haplotype dosage imbalance, and other similar imbalances. As an example, an allelic imbalance can occur when a tumor has one allele of a gene deleted or one allele of a gene amplified or differential amplification of the two alleles in its genome, thereby creating an imbalance at a particular locus in the sample. As another example, a patient could have an inherited mutation in a tumor suppressor gene. The patient could then go on to develop a tumor in which the non-mutated allele of the tumor suppressor gene is deleted. Thus, within the tumor, there is mutation dosage imbalance. When the tumor releases its DNA into the plasma of the patient, the tumor DNA will be mixed in with the constitutional DNA (from normal cells) of the patient in the plasma. Through the use of methods described herein, mutational dosage imbalance of this DNA mixture in the plasma can be detected.

The term "haplotype" as used herein refers to a combination of alleles at multiple loci that are transmitted together on the same chromosome or chromosomal region. A haplotype may refer to as few as one pair of loci or to a chromosomal region, or to an entire chromosome. The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of organisms typically includes multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. As used herein, the term "polymorphism" refers to any inter-individual variation in the human genome, regardless of its frequency. Examples of such variations include, but are not limited to, single nucleotide polymorphism, simple tandem repeat polymorphisms, insertion-deletion polymorphisms, mutations (which may be disease causing) and copy number variations.

The term "sequenced tag" refers to a sequence determined from all or part of a nucleic acid molecule, e.g., a DNA fragment. Often, just one end of the fragment is sequenced, e.g., about 30 bp. The sequenced tag can then be aligned to a reference genome. Alternatively, both ends of the fragment can be sequenced to generate two sequenced tags, which can provide greater accuracy in the alignment and also provide a length of the fragment.

The term "universal sequencing" refers to sequencing where adapters are added to the end of a fragment, and the primers for sequencing attached to the adapters. Thus, any fragment can be sequenced with the same primer, and thus the sequencing can be random.

The term "size distribution" refers to any one value or a set of values that represents a length, mass, weight, or other measure of the size of molecules corresponding to a particular group (e.g. fragments from a particular haplotype or from a particular chromosomal region). Various embodiments can use a variety of size distributions. In some embodiments, a size distribution relates to the rankings of the sizes (e.g., an average, median, or mean) of fragments of one chromosome relative to fragments of other chromosomes. In other embodiments, a size distribution can relate to a statistical value of the actual sizes of the fragments of a chromosome. In one implementation, a statistical value can include any average, mean, or median size of fragments of a chromosome. In another implementation, a statistical value can include a total length of fragments below a cutoff value, which may be divided by a total length of all fragments, or at least fragments below a larger cutoff value.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1). The term "cutoff" and "threshold" refer to a predetermined number used in an operation. For example, a cutoff size can refer to a size above which fragments are excluded. A threshold value may be a value above or below which a particular classification applies. Either of these terms can be used in either of these contexts.

The term "level of cancer" can refer to whether cancer exists, a stage of a cancer, a size of tumor, how many deletions or amplifications of a chromosomal region are involved (e.g. duplicated or tripled), and/or other measure of a severity of a cancer. The level of cancer could be a number or other characters. The level could be zero. The level of cancer also includes premalignant or precancerous conditions associated with deletions or amplifications.

DETAILED DESCRIPTION

Cancerous tissue (tumor) can have aberrations, such as deletion or amplification of a chromosomal region. The tumor can release DNA fragments into fluids in the body. Embodiments can identify a tumor by analyzing the DNA fragments to identify the aberrations relative to normal (expected) values for DNA in the chromosomal region.

The exact size of the deletion or amplification can vary, as well as the location. There may be times when a particular region is known to show aberration in general for cancers or for a particular type of cancer (thereby leading to a diagnosis of a particular cancer). When a particular region is not known, a systematic method for analyzing the entire genome or large parts of the genome may be employed to detect aberrant regions that may be dispersed throughout the genome and whose size (e.g. number of bases deleted or amplified) varies. The chromosomal region(s) can be tracked over time to identify changes in a severity of an aberration or a number of regions showing an aberration. This tracking can provide vital information for screening, prognosticating, and monitoring a tumor (e.g. after treatment or for detecting relapse or tumor progression).

This description first starts out with examples of chromosomal aberrations in cancer. Then, examples of ways to detect a chromosomal aberration by detecting and analyzing cell-free DNA in a biological sample is discussed. Once the methods of detecting an aberration in one chromosomal region is established, methods for detecting aberrations in many chromosomal regions are used in systematic way to screen (diagnose) and prognosticate patients is described. This description also describes methods for tracking numerical indicators obtained from tests for chromosomal aberration in one or more regions over time to provide screening, prognosticating, and monitoring of patients. Examples are then discussed.

I. EXAMPLES OF CHROMOSOMAL ABERRATIONS IN CANCER

Chromosomal aberrations are commonly detected in cancer cells. Moreover, characteristic patterns of chromosomal aberrations can be found in selected types of cancer. For example, gains of DNA in chromosome arms 1p, 1q, 7q, 15q, 16p, 17q and 20q and losses of DNA at 3p, 4q, 9p and 11q are commonly detected in hepatocellular carcinoma (HCC). Previous studies have demonstrated that such genetic aberrations could also be detected in the circulating DNA of cancer patients. For example, loss of heterozygosity (LOH) has been detected for a particular locus in the circulating DNA molecules of patients suffering from lung, and head and neck cancers (Chen X Q, et al. Nat Med 1996; 2: 1033-5; Nawroz H, et al. Nat Med 1996; 2: 1035-7). The genetic alterations detected in the plasma or serum were identical to those found in the tumor tissues. However, as tumor-derived DNA only contributes a minor fraction of total circulating cell-free DNA, the allelic imbalance caused by LOH of tumor cells is usually small. A number of investigators have developed the digital polymerase chain reaction (PCR) technology (Vogelstein B, Kinzler K W. Proc Natl Acad Sci USA. 1999; 96: 9236-41; Zhou W, et al. Nat Biotechnol 2001; 19: 78-81; Zhou W, et al. Lancet. 2002; 359: 219-25) for the accurate quantification of different alleles of a locus among the circulating DNA molecules (Chang H W, et al. J Natl Cancer Inst. 2002; 94: 1697-703). Digital PCR is much more sensitive than real-time PCR or other DNA quantification methods for the detection of a small allelic imbalance caused by the LOH at a particular locus in the tumor DNA. However, digital PCR can still have difficulties in identifying a very small allelic imbalance at a particular locus, and thus embodiments described herein analyze chromosomal regions in a collective fashion.

The technology described herein also has applications for the detection of premalignant or precancerous conditions. Examples of such conditions including cirrhosis of the liver and cervical intraepithelial neoplasia. The former condition is a premalignant condition for hepatocellular carcinoma while the latter condition is a premalignant condition for cervical carcinoma. It has been reported that such premalignant conditions already possess several of the molecular alterations in their evolution to become a malignant tumor. For example, the presence of LOH at chromosome arms 1p, 4q, 13q, 18q and concurrent losses at more than 3 loci are associated with an increased risk of HCC development in patients with liver cirrhosis (Roncalli M et al. Hepatology 2000; 31:846-50). Such premalignant lesions would also release DNA into the circulation, although likely to be at lower concentrations. The technology can allow detection of deletions or amplifications by analyzing DNA fragments in plasma and to measure the concentration (including fractional concentration) of circulating premalignant DNA in plasma. The ease with which such aberrations are detected (e.g. depth of sequencing or the number of such changes detected) and the concentrations would predict the likelihood or rapidity of progression to a full blown cancerous condition.

A. Deletion of a Chromosomal Region

FIG. 1 illustrates a chromosomal region of a cancer cell exhibiting an aberration of a deletion. The normal cell is shown with two haplotypes, Hap I and Hap II. As shown, both Hap I and Hap II have a sequence at each of a plurality of heterozygous loci 110 (also referred to as single nucleotide polymorphisms SNPs). In the cell associated with cancer, Hap II has chromosomal region 120 deleted. As examples, the cell associated with cancer can be from a tumor (e.g., a malignant tumor), from a metastatic focus of the tumor (e.g. in a regional lymph node, or in a distant organ), or from a pre-cancerous or premalignant lesion, e.g., as is mentioned above.

In chromosomal region 120 of the cancer cell in which one of the two homologous haplotypes is deleted, all the heterozygous SNPs 110 would appear as homozygous because of the loss of the other allele on the corresponding deleted homologous chromosome. Therefore, this type of chromosomal aberration is called loss of heterozygosity (LOH). In region 120, the non-deleted alleles of these SNPs would represent one of the two haplotypes which can be found in the normal tissues. In the example shown in FIG. 1, the haplotype I (Hap I) at the LOH region 120 can be determined by genotyping the tumor tissue. The other haplotype (Hap II) can be determined by comparing the apparent genotypes of the normal tissues and the cancer tissues. Hap II can be constructed by joining all the deleted alleles. That is all of the alleles in the normal cell for region 120 that do not appear in region 120 for the cancer cell are determined to be on the same haplotype, i.e. Hap I. Through this analysis, the haplotypes of patients (e.g., hepatocellular carcinoma HCC patients) can be determined for all chromosomal regions exhibiting LOH in the tumor tissue. Such a method is only useful if one has cancer cells, and only works for determining the haplotype in region 120, but does provide a good illustration of a deleted chromosomal region.

B. Amplification of a Chromosomal Region

Figure 2:
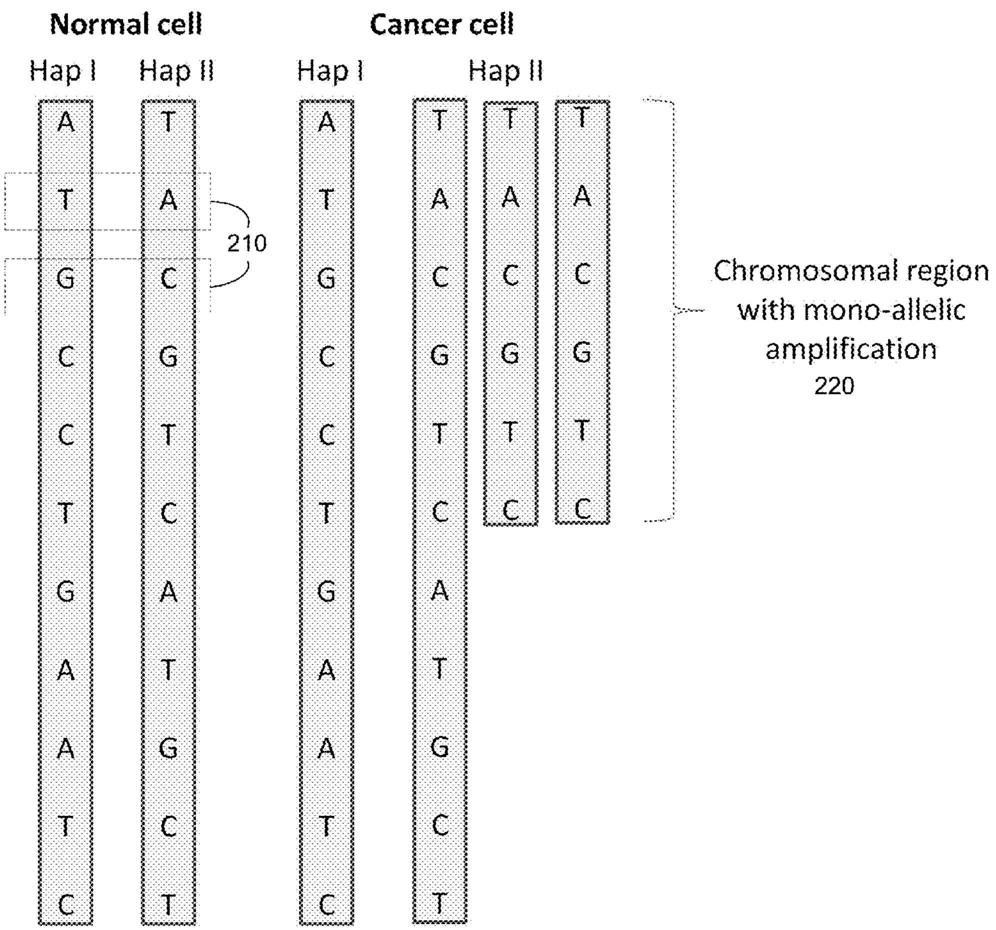
FIG. 2 illustrates a chromosomal region of a cancer cell exhibiting an aberration of an amplification. (Hap I (SEQ ID NO:1) and Hap II (SEQ ID NO:2))

FIG. 2 illustrates a chromosomal region of a cancer cell exhibiting an aberration of an amplification. The normal cell is shown with two haplotypes, Hap I and Hap II. As shown, both Hap I and Hap II have a sequence at each of a plurality of heterozygous loci 210. In the tumor cell, Hap II has chromosomal region 220 amplified two times (duplicated).

Similarly, for regions with mono-allelic amplification in the tumor tissues, the amplified alleles at the SNPs 210 can be detected by methods such as microarray analysis. One of the two haplotypes (Hap II in the example shown in FIG. 2) can be determined by joining up all the amplified alleles in chromosomal region 220. The amplified allele at a particular locus can be determined by comparing the number of each of the alleles at the locus. Then, the other haplotype (Hap I) can be determined by joining up the non-amplified alleles. Such a method is only useful if one has cancer cells, and only works for determining the haplotype in region 220, but does provide a good illustration of an amplified chromosomal region.

An amplification can result from having more than 2 chromosomes, or the repeating of a gene in one chromosome. One region could be tandemly duplicated, or a region could be a minute chromosome that contains one or more copies of the region. The amplification could also result from a gene of one chromosome being copied and inserted into a different chromosome or a different region in the same chromosome. Such insertions are a type of amplification.

II. SELECTION OF A CHROMOSOMAL REGION

As cancer tissue will contribute at least some of these cell-free DNA (and potentially cellular DNA), the genomic aberrations of the cancer tissue can be detected in the sample such as plasma and serum. A problem with detecting the aberration is that the tumour or cancer may be quite small, thereby providing relatively little DNA from the cancer cells. Thus the amount of circulating DNA with the aberration is quite small, thereby making detection very difficult. There may not be enough DNA at a single locus in the genome to detect an aberration. Methods described herein can overcome this difficulty by analyzing DNA at a chromosomal region including a plurality of loci (haplotype), thus changing a small variation at one locus into a perceptible difference when aggregated over the haplotype. Thus, analyzing a plurality of loci of a region can provide greater accuracy, and can reduce false positives and false negatives.

Also, the region of aberration may be quite small, thereby making identifying the aberration difficult. If just one locus or specific loci are used, aberrations not at those loci will be missed. Some methods, as described herein, can investigate whole regions to find an aberration within a subset of the region. When the analyzed regions span the genome, the whole genome can thus be analyzed to find aberrations of varying length and location, as is described in more detail below.

To illustrate these points, as shown above, a region can have an aberration. But, a region must be selected for analysis. The length and position of a region can alter the results, and thus affect the analysis. For example, if the first region in FIG. 1 is analyzed, no aberration would be detected. If the second region is analyzed, an aberration can be detected, e.g., using methods described herein. If a larger region including both the first and second region were analyzed, one encounters the difficulty that only part of the larger region has an aberration, which may make identifying any aberration more difficult, as well as the problem of identifying the exact location and length of the aberration. Various embodiments can address some and/or all of these difficulties. The description for selecting a region is equally applicable to methods that use haplotypes of a same chromosomal region, or that use two different chromosomal regions.

A. Selecting a Particular Chromosomal Region

In one embodiment, a particular region could be selected based on the knowledge of the cancer or the patient. For example, the region could be known to commonly exhibit aberration in many cancers or a particular cancer. The exact length and position of the region can be determined by referring to the literature regarding what is well known for the cancer type or for patients with particular risk factors. Additionally, the tumor tissues of the patient can be obtained and analyzed to identify regions of aberrations, as is described above. Now such a technique would require obtaining a cancer cell (which may not be practical for patients just being diagnosed), but such a technique can be used to identify regions for monitoring over time in the same patient (e.g., after surgery to remove cancerous tissue, or after chemotherapy or immunotherapy or targeted therapy, or for detecting tumor relapse or progression).

One could identify more than one particular region. The analysis of each one of such regions can be used independently, or the different regions can be analyzed collectively. Additionally, a region may be subdivided to provide greater accuracy in locating an aberration.

FIG. 3 shows a table 300 illustrating different types of cancers and associated regions and their corresponding aberrations. Column 310 lists the different cancer types. Embodiments described herein can be used for any type of cancer involving an aberration, and thus this list is just of examples. Column 320 shows regions (e.g., large regions, such as 7p or more specific regions of 17q25) where a gain (amplification) is associated with the particular cancer of the same row. Column 330 shows regions where losses (deletions) can be found. Column 340 lists references that discuss the association of these regions with the particular cancer.

These regions with potential chromosomal aberrations can be used as the chromosomal region(s) for analysis according to methods described herein. Examples of other genomic regions altered in cancer can be found at the database of the Cancer Genome Anatomy Project (cgap.nci.nih.gov/Chromosomes/RecurrentAberrataions) and the Atlas of Genetics and Cytogenetics in Oncology and Haematology (atlasgeneticsoncology.org Tumors/Tumorliste.html).

As one can see, the identified regions can be quite large while other may be more specific. The aberration may not include the entire region identified in the table. Thus, such clues about the type of aberrations does not pinpoint exactly where the aberration actually exists for a particular patient, but may be more used as a rough guide about large regions for analysis. Such large regions may include many subregions (which may be of equal size) that are analyzed individually as well as collectively in the larger region (details of which are described herein). Thus, embodiments may combine aspects of selecting a large region based on particulars of the cancer to be tested, but may also employ more general techniques (e.g., testing the subregions) as is described next.

B. Selecting an Arbitrary Chromosomal Region

In another embodiment, a chromosomal region being analyzed is chosen arbitrarily. For example, the genome could be separated into regions that are one megabase (Mb) in length, or other predetermined segment lengths such as 500 Kb or 2 Mb. If the regions are 1 Mb, then there are approximately 3,000 regions in the human genome, since there are about 3 billion bases in the haploid human genome. These regions can then each be analyzed, as is discussed in more detail later.

Such regions may be determined, not based on any knowledge of cancer or the patient, but based on a systematic partitioning of the genome into regions to be analyzed. In one implementation, when a chromosome does not have a length that is a multiple of the predetermined segment (e.g., not divisible by 1 million bases), the last region of a chromosome could be less than the predetermined length (e.g. less than 1 MB). In another implementation, each chromosome could be separated into regions of equal length (or approximately equal—within rounding error) based on the total length of the chromosome and the number of segments to be created (which would typically vary among the chromosomes). In such an implementation, the length of the segments of each chromosome could differ.

As mentioned above, a particular region can be identified based on a specific cancer being tested, but then the particular region can be subdivided into smaller regions (e.g. subregions of equal size that span the particular larger region). In this manner, aberrations may be pinpointed. In the discussion below, any general reference to a chromosomal region may be a region that is specifically identified, a region that is chosen arbitrarily, or a combination of both.

III. DETECTION OF ABERRATIONS IN A PARTICULAR HAPLOTYPE

This section describes methods for detecting an aberration in a single chromosomal region by analyzing a biological sample that includes cell-free DNA. In the embodiments of this section, the single chromosomal region is heterozygous (different alleles) at a plurality of loci in the region, thereby providing two haplotypes that can be distinguished by knowing the particular allele at a given locus. Thus, a given nucleic acid molecule (e.g., a fragment of cell-free DNA) can be identified as being from a particular one of the two haplotypes. For example, the fragment can be sequenced to obtain a sequence tag that aligns to the chromosomal region, and then the haplotype at a heterozygous loci to which the allele belongs can be identified. Two general types of techniques are described below for determining aberrations in a particular haplotype (Hap), specifically tag counting and size analysis.

A. Determining Haplotypes

To differentiate between the two haplotypes, the two haplotypes of a chromosomal region are first determined. For example, the two haplotypes Hap I and Hap II shown in the normal cell of FIG. 1 can be determined. In FIG. 1, the haplotypes include a first plurality of loci 110, which are heterozygous, and allow for a differentiation between the two haplotypes. This first plurality of loci span the chromosomal region being analyzed. The alleles on the different heterozygous loci (hets) can first be determined and then phased to determine the haplotypes of the patient.

The haplotype of the SNP alleles can be determined by single molecule analysis methods. Examples of such methods have been described by Fan et al (Nat Biotechnol. 2011; 29:51-7), Yang et al (Proc Natl Acad Sci USA. 2011; 108:12-7) and Kitzman et al (Nat Biotechnol. 2011 January; 29:59-63). Alternatively, the haplotypes of an individual can be determined by the analysis of the genotypes of the family members (e.g. parents, siblings, and children). Examples include the methods described by Roach et al (Am J Hum Genet. 2011; 89(3):382-97) and Lo et al (Sci Transl Med. 2010; 2:61ra91). In yet another embodiment, the haplotype of the individuals can be determined by comparing the genotyping results of the tumor tissues and the genomic DNA. The genotype of these subjects can be performed by microarray analysis, such as using t Haplotypes can also be constructed by other methods well known to those skilled in the art. Examples of such methods include those based on single molecule analysis such as digital PCR (Ding C and Cantor C R. Proc Natl Acad Sci USA 2003; 100: 7449-7453; Ruano G et al. Proc Natl Acad Sci USA 1990; 87: 6296-6300), chromosome sorting or separation (Yang H et al. Proc Natl Acad Sci USA 2011; 108: 12-17; Fan H C et al. Nat Biotechnol 2011; 29: 51-57), sperm haplotyping (Lien S et al. Curr Protoc Hum Genet 2002; Chapter 1:Unit 1.6) and imaging techniques (Xiao M et al. Hum Mutat 2007; 28: 913-921). Other methods include those based on allele-specific PCR (Michalatos-Beloin S et al. Nucleic Acids Res 1996; 24: 4841-4843; Lo Y M D et al. Nucleic Acids Res 19: 3561-3567), cloning and restriction enzyme digestion (Smirnova A S et al. Immunogenetics 2007; 59:93-8), etc. Yet other methods are based on the distribution and linkage disequilibrium structure of haplotype blocks in the population which allow the subject's haplotype to be inferred from statistical assessments (Clark A G. Mol Biol Evol 1990; 7:111-22; 10:13-9; Salem R M et al. Hum Genomics 2005; 2:39-66).

Another method of determining the haplotype of the region of LOH is by genotyping the normal tissues and the tumoral tissues of the subject if the tumoral tissues are available. In the presence of LOH, tumoral tissues with a very high fractional concentration of tumor cells would show an apparent homozygosity for all the SNP loci within the region showing LOH. The genotypes of these SNP loci would comprise one haplotype (Hap I of the LOH region in FIG. 1). On the other hand, the normal tissues would indicate that the subject is heterozygous for the SNP loci within the region of LOH. The alleles that are present in the normal tissues but not the tumoral tissues would comprise the other haplotype (Hap II of the LOH region in FIG. 1).

B. Relative Haplotype Dosage (RHDO) Analysis

As mentioned above, chromosomal aberrations with amplification or deletion of one of the haplotypes of a chromosome region would lead to an imbalance of the dosage of the two haplotypes in the chromosome region in the tumor tissues. In the plasma of a person with a tumoral growth, a fraction of the circulating DNA is derived from the tumor cells. Due to the presence of tumor-derived DNA in the plasma of cancer patients, such imbalance would also be present in their plasma. The imbalance in the dosage of the two haplotypes can be detected through counting the number of molecules coming from each haplotype.

For the chromosomal regions in which LOH is observed in the tumor tissues (e.g. region 120 of FIG. 1), Hap I would be over-represented among the circulating DNA molecules (fragments) when compared with Hap II because of the lack of contribution of Hap II from the tumor tissues. For the chromosomal regions in which the copy number amplification is observed in the tumor tissues, Hap II would be over-represented when compared with Hap I for the regions affected by mono-allelic amplification of Hap II because of the release of an additional dose of Hap II from the tumor tissues. To determine an over or under representation, certain DNA fragments in a sample are determined to be from Hap I or Hap II, which can be done by a variety of methods, e.g. by performing universal sequencing and aligning or using digital PCR and sequence-specific probes.

After sequencing of a plurality of DNA fragments from the plasma (or other biological sample) of the cancer patients to generate sequenced tags, the sequenced tags corresponding to the alleles on the two haplotypes can be identified and counted. The numbers of sequenced tags corresponding to each of the two haplotypes can then be compared to determine if the two haplotypes are equally represented in the plasma. In one embodiment, sequential probability ratio testing (SPRT) can be used to determine if the representations of the two haplotypes in plasma are significantly different. A statistically significant difference suggests the presence of a chromosomal aberration at the analyzed chromosomal region. In addition, the quantitative difference of the two haplotypes in plasma can be used for the estimation of the fractional concentration of tumor-derived DNA in the plasma, as is described below.

The diagnostic approaches for determining an identity of a DNA fragment (e.g. its location in the human genome) described in this application are not limited to using massively parallel sequencing as the detection platform. These diagnostic approaches can also be applied to, for example but not limited to, microfluidics digital PCR systems (e.g. Fluidigm digital array system, microdroplet digital PCR system (e.g. those from RainDance and QuantaLife), the BEAM-ing system (i.e. beads, emulsion PCR, amplification and magnetics) (Diehl et al. Proc Natl Acad Sci USA 2005; 102: 16368-16373), real-time PCR, mass spectrometry based systems (e.g. the SequenomMassArray system) and multiplex ligation-dependent probe amplification (MLPA) analysis.

Normal Regions

Figure 4:
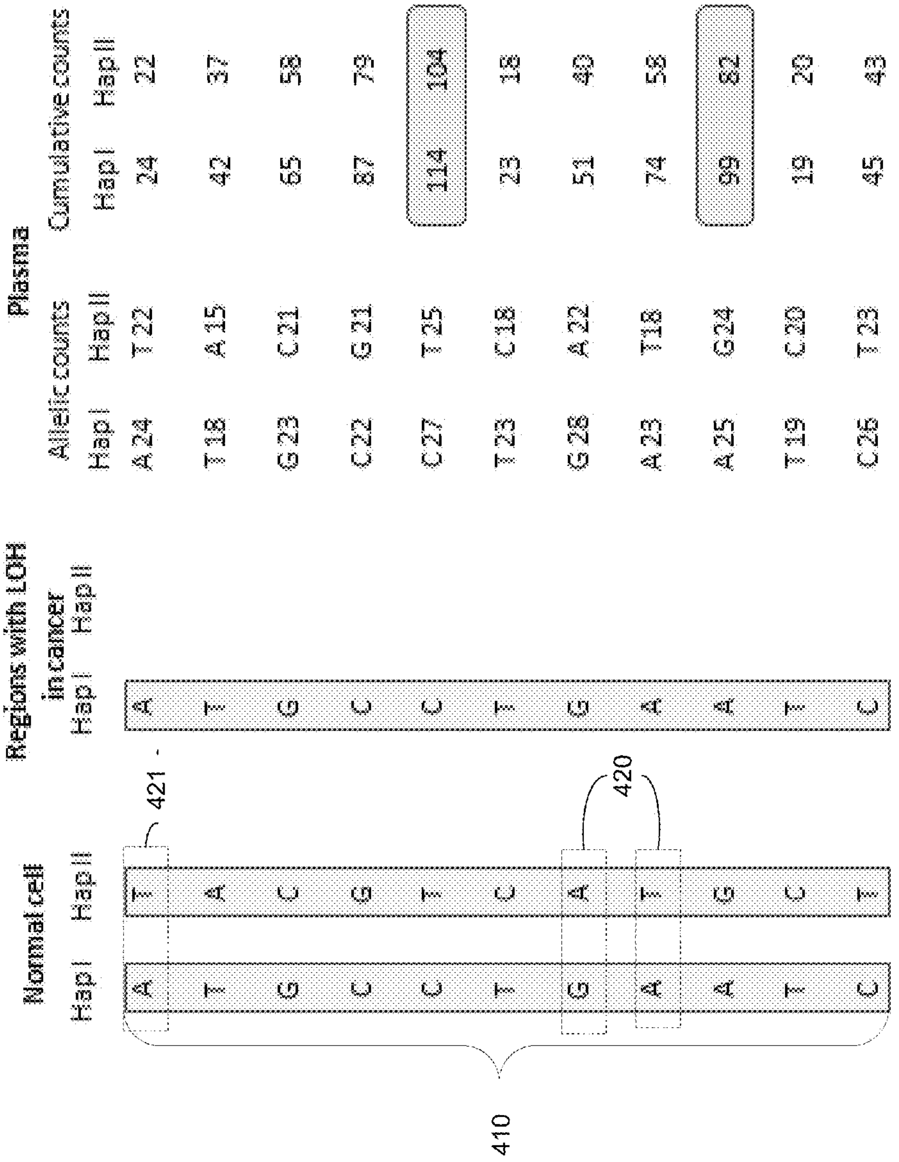
FIG. 4 illustrates chromosomal regions within a cancer cell that do not exhibit an aberration along with measurements made in plasma according to embodiments of the present invention. (Hap I (SEQ ID NO:1) and Hap II (SEQ ID NO:2))

FIG. 4 illustrates chromosomal regions within a cancer cell that do not exhibit an aberration along with measurements made in plasma according to embodiments of the present invention. The chromosomal region 410 may be selected by any method, e.g., based on a specific cancer to be tested or based on a general screening that uses predetermined segments that span large sections of the genome. To differentiate between the two haplotypes, the two haplotypes are first determined. FIG. 4 shows two haplotypes (Hap I and Hap II) of a normal cell for chromosomal region 410. The haplotypes include a first plurality of loci 420. This first plurality of loci 420 span the chromosomal region 410 being analyzed. As shown, these loci are heterozygous in the normal cell. The two haplotypes for a cancer cell are also shown. In the cancer cell, no regions are deleted or amplified.

FIG. 4 also shows the number of allelic counts on each haplotype for each of the loci 420. A cumulative total is also provided for certain subregions of chromosomal region 410. The number of allelic counts corresponds to the number of DNA fragments that correspond to the particular haplotype at each the particular locus. For example, a DNA fragment that includes the first loci 421 and has the allele A would get counted toward Hap I. And, a DNA fragment with allele T would get counted toward Hap II. The determination of where a fragment aligns (i.e. whether it includes a particular locus) and what allele it contains can be determined in various ways, as is mentioned herein. A ratio of the counts on the two haplotypes may be used to determine whether a statistically significant different exists. This ratio is called an odds ratio, herein. A difference between the two values may also be used; the difference may be normalized by a total number of fragments. The ratio and difference (and functions thereof) are examples of parameters that are compared to thresholds to determine classifications of whether an aberration exists.

The RHDO analysis can make use of all alleles on the same haplotype (e.g. cumulative counts) for determining if there is any imbalance of the two haplotypes in the plasma, e.g., as can be done in maternal plasma as described in the Lo patent application Ser. Nos. 12/940,992 and 12/940,993, referred to above. This method can significantly increase the number of DNA molecules used for determining if there is any imbalance and, hence, results in better statistical power for differentiating an imbalance due to the presence of cancer from stochastic distribution of allelic counts in the absence of cancer or a pre-malignant condition. In contrast to analyzing multiple SNP loci separately, the RHDO approach can make use of the relative position of the alleles on the two chromosomes (haplotype information) such that the alleles located on the same chromosome can be analyzed together. In the absence of the haplotype information, the allele counts of different SNP loci cannot be added together to statistically determine if a haplotype is over- or under-represented in plasma. The quantification of the allelic counts can be performed by, but not limited to, massively parallel sequencing (e.g. using the Illumina sequencing by synthesis system, the sequencing by ligation technology (SOLiD) by Life Technologies, the Ion Torrent sequencing system by Ion Torrent and Life Technologies, nanopore sequencing (nanoporetech.com), and the 454 sequencing technology (Roche), digital PCR (e.g. by microfluidics digital PCR (for example Fluidigm (fluidigm.com)) or the BEAMing (beads, emulsion PCR, amplification, magnetics (inostics.com)) or droplet PCR (e.g. by QuantaLife (quantalife.com) and RainDance (raindancetechnologies.com)) and real-time PCR. In other implementation of the technology, enriched target sequencing using in-solution capture (e.g. using the Agilent SureSelect system, the Illumina TruSeq Custom Enrichment Kit (illumina.com/applications/sequencing/targeted_resequencing.ilmn), or by the MyGenostics GenCap Custom Enrichment system (mygenostics.com/)) or array-based capture (e.g. using the Roche NimbleGen system) can be used.

In the example shown in FIG. 4, a slight allelic imbalance is observed for the first two SNP loci (24 vs 26 for the first SNP and 18 vs 20 for the second SNP). However, number of allelic counts is not statistically sufficient to determine if a real allelic imbalance is present. Thus, the counts of alleles on the same haplotype are added together until the cumulative allelic counts for the two haplotypes are sufficient to conclude statistically that no allelic imbalance between the two haplotypes is present for chromosomal region 410 (the fifth SNP for this example). After a statistically significant classification is arrived, the cumulative count is reset (at the sixth SNP for this example). The cumulative count is then determined until the cumulative allelic counts for the two haplotypes are again sufficient to conclude statistically that no allelic imbalance between the two haplotypes for that particular subregion of region 410. A total cumulative count could be used for the entire region as well, but the previous method can allow different subregions to be tested, which provides for greater precision (i.e. a subregion) in determining a location of an aberration, as opposed to the entire region 410. Examples of statistical tests for determining whether a real allelic imbalance is present include, but not limited to, the sequential probability ratio testing (Zhou W, et al. Nat Biotechnol 2001; 19: 78-81; Zhou W, et al. Lancet. 2002; 359: 219-25), the t-test, and the chi-square test.

Detecting Deletions

Figure 5:
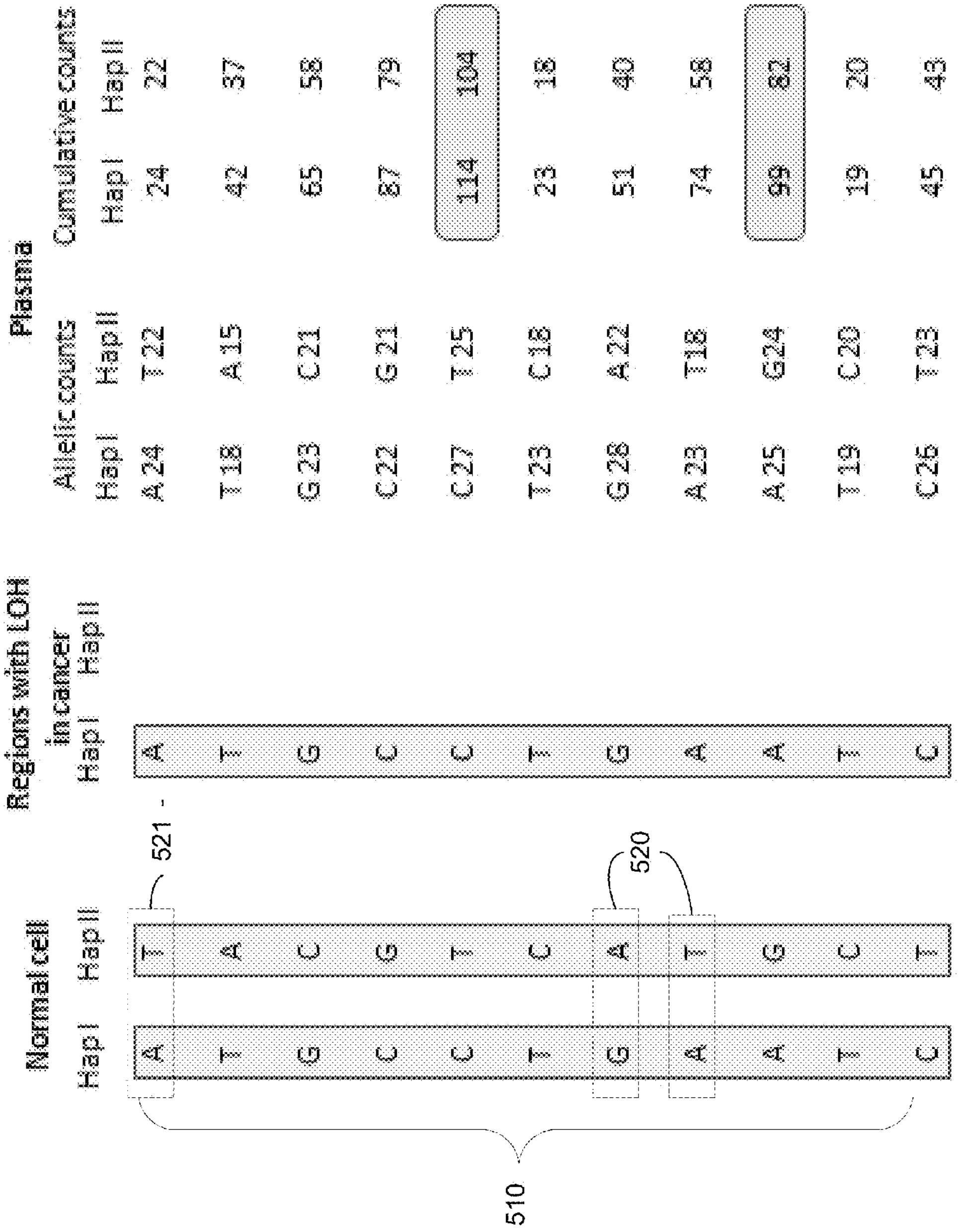
FIG. 5 illustrates the deletion of chromosomal region 510 within a cancer cell along with measurements made in plasma to determine the deleted region according to embodiments of the present invention. (Hap I (SEQ ID NO:1) and Hap II (SEQ ID NO:2))

FIG. 5 illustrates the deletion of chromosomal region 510 within a cancer cell along with measurements made in plasma to determine the deleted region according to embodiments of the present invention. FIG. 5 shows two haplotypes (Hap I and Hap II) of a normal cell for chromosomal region 510. The haplotypes include a first plurality of heterozygous loci 520 that span the chromosomal region 510 being analyzed. The two haplotypes for a cancer cell are also shown. In the cancer cell, region 510 is deleted for Hap II. As with FIG. 4, FIG. 5 also shows the number of allelic counts for each of the loci 520. A cumulative total is also kept for certain subregions within chromosomal region 510.

As tumor tissues typically contain a mixture of tumor cells and non-tumor cells, the LOH may be manifested by skewing of the ratio of the amounts of the two alleles at loci within the region 510. In such a situation, the deleted haplotype Hap II in region 510 can be determined by the combination of loci 520 which show a relative reduction in the amounts of DNA fragments, when compared with the corresponding loci on the normal tissues. The haplotype with fragments that appear more often is Hap I, which is retained in the tumor cells. In certain embodiments, it might be desirable to perform a procedure that would enrich the proportion of tumor cells in the tumor sample, so as to allow the deleted and retained haplotypes to be determined more readily. One example of such a procedure is microdissection (either manually or by laser capture techniques).

Theoretically, each of the alleles on Hap I would be over-represented in the circulating DNA for the chromosomal region exhibiting LOH in the tumor tissues and the degree of allelic imbalance would be dependent on the fractional concentration of tumor DNA in the plasma. However, at the same time, the relative abundance of the two alleles in any circulating DNA sample would also be governed by the Poisson distribution. A statistical analysis can be performed to determine if an observed allelic imbalance is due to the presence of LOH in cancer tissues or due to chance. The power of detecting real allelic imbalance associated with LOH in cancer is dependent on the number of circulating DNA molecules being analyzed and the fractional concentration of tumoral DNA. A higher fractional concentration of tumoral DNA and a larger number of molecules analyzed would give rise to higher sensitivity and specificity for detecting real allelic imbalance.

In the example shown in FIG. 5, a slight allelic imbalance is observed for the first two SNP loci (24 vs 22 for the first SNP and 18 vs 15 for the second SNP). However, number of allelic counts is not statistically sufficient to determine if a real allelic imbalance is present. Thus, the counts of alleles on the same haplotype are added together until the cumulative allelic counts for the two haplotypes are sufficient to conclude statistically that an allelic imbalance between the two haplotypes is present in region 510 (the fifth SNP for this example). In some embodiments, only an imbalance is known, and the specific type (deletion of amplification) is not determined. The cumulative count is then determined until the cumulative allelic counts for the two haplotypes are again sufficient to conclude statistically that an allelic imbalance between the two haplotypes for that particular subregion of region 510. A total cumulative count could be used for the entire region as well, as which may be done in any method described herein.

Detecting Amplification of a Chromosomal Region

Figure 6:
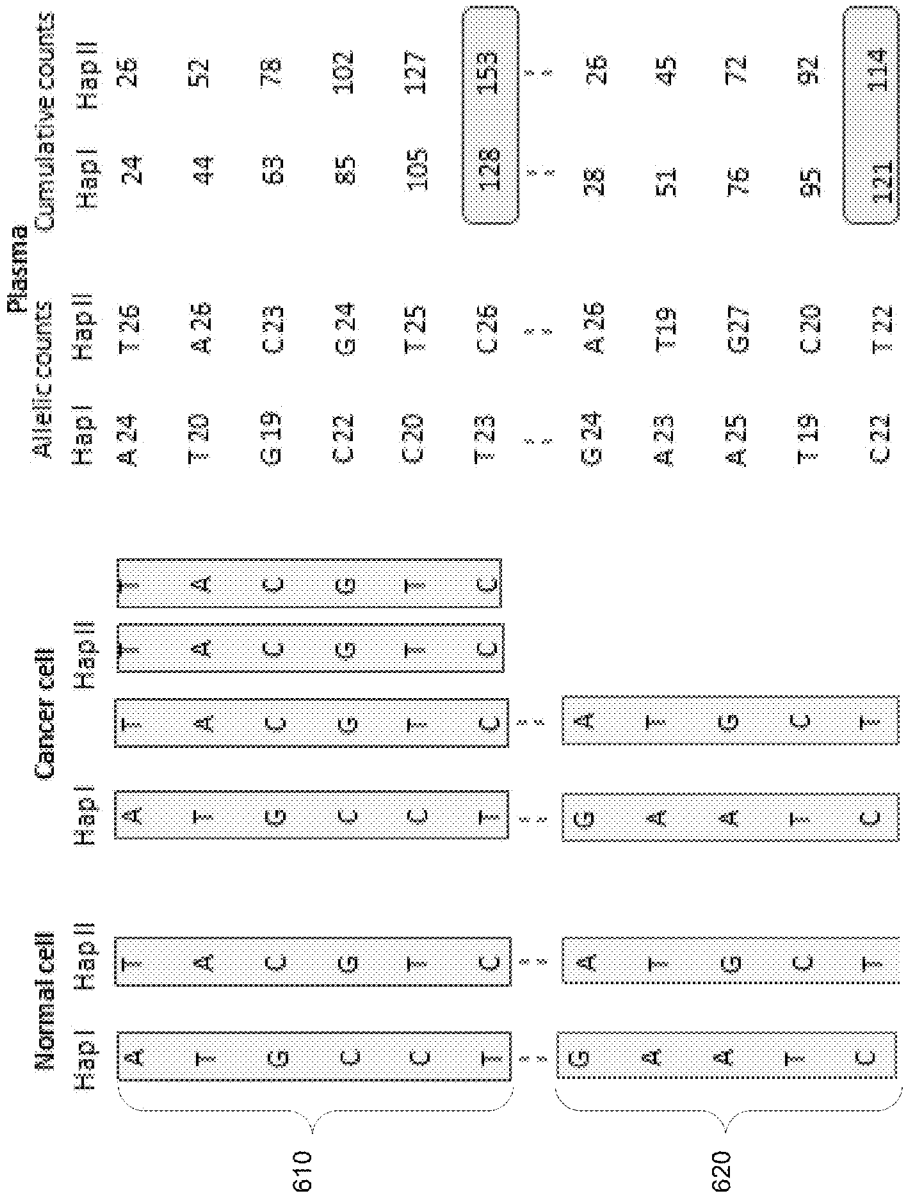
FIG. 6 illustrates the amplification of chromosomal region 610 within a cancer cell along with measurements made in plasma to determine the amplified region according to embodiments of the present invention. (Hap I (SEQ ID NO:1) and Hap II (SEQ ID NO:2))

FIG. 6 illustrates the amplification of chromosomal region 610 within a cancer cell along with measurements made in plasma to determine the amplified region according to embodiments of the present invention. In addition to LOH, amplification of chromosomal regions is also frequently observed in cancer tissues. In the example shown in FIG. 6, Hap II in chromosomal region 610 is amplified to three copies in the cancer cell. As shown, region 610 includes only six heterozygous loci as opposed to the longer regions shown in previous figures. The amplification is detected as being statistically significant in the sixth loci, where the over-representation is determined to be statistically significant. In some embodiments, only an imbalance is known, and the specific type (deletion or amplification) is not determined. In other embodiments, a cancer cell may be obtained and analyzed. Such analysis can provide information about whether the imbalance is due to a deletion (cancer cell is homozygous for deleted region) or an amplification (cancer cell is heterozygous for amplified region). In other implementations, whether a deletion or amplification exists can be determined using the methods of section IV to analyze the entire region (i.e. not the haplotypes individually). If the region is over-represented, then the aberration is an amplification; and if the region is under-represented, then aberration is a deletion. Region 620 is also analyzed and the cumulative counts confirm that no imbalance exists.

SPRT Analysis for the Plasma RHDO Analysis

For any chromosomal regions that have heterozygous loci, RHDO analysis can be used to determine if there is any dosage imbalance of the two haplotypes in the plasma. In these regions, the presence of haplotype dosage imbalance in plasma is suggestive of the presence of tumor-derived DNA in the plasma sample. In one embodiment, SPRT analysis can be used to determine if the difference in the number of sequenced reads for Hap I and Hap II is statistically significant. In this example of SPRT analysis, we first determine the number of sequenced reads coming from each of the two haplotypes. Then we can determine a parameter (e.g. a fraction) that represents the proportional amount of sequenced reads contributed by the potentially over-represented haplotype (e.g. a fraction of the number of reads for one haplotype divided by the number of reads for the other haplotype). The potentially over-represented haplotype would be the non-deleted haplotype in the scenario of LOH and the amplified haplotype in the scenario of mono-allelic amplification of a chromosomal region. Then, this fraction would be compared with two threshold values (the upper and lower thresholds) which are constructed based on the null hypothesis, i.e. the absence of haplotype dosage imbalance, and the alternative hypothesis, i.e. the presence of haplotype dosage imbalance. If the fraction is greater than the upper threshold, it indicates the presence of a statistically significant imbalance of the two haplotypes in plasma. If the fraction is below the lower threshold, it indicates that no statistically significant imbalance of the two haplotypes is present. If the fraction is between the upper and lower thresholds, it indicates that there is not sufficient statistical power to make a conclusion. A sequential increase in the number of heterozygous loci for the region being analyzed may be performed until a successful SPRT classification can be made.

The equations for calculating the upper and lower boundaries of the SPRT are: Upper threshold=[(ln 8)/N−ln δ]/ln γ; Lower threshold=[(ln 1/8)/N−ln δ]/ln γ, where $$\delta = (1-\theta_1)/(1-\theta_2)$$

and $$\gamma = \frac{\theta_1(1-\theta_2)}{\theta_2(1-\theta_1)},$$

$\theta_1$ is the expected fraction of sequenced tags from the potentially over-represented haplotype when allelic imbalance is present in plasma, $\theta_2$ is the expected fraction of any of the two haplotypes when allelic imbalance is not present, i.e. 0.5, N is the total number of sequenced tags for Hap I and Hap II, ln is a mathematical symbol representing the natural logarithm, i.e. $\log_e$). $\theta_1$ would be dependent on the fractional concentration of tumor-derived DNA (F) that one expects (or knows) to be present in the plasma sample.

In the scenario of LOH, $\theta_1=1/(2-F)$. In the scenario of mono-allelic amplification, $\theta_1=(1+zF)/(2+zF)$, where z represents the number of the extra copy of the chromosomal region that is amplified in the tumor. For example, if one chromosome is duplicated, there would be one extra copy of the particular chromosome. Then, z is equal to 1.

Figure 7:
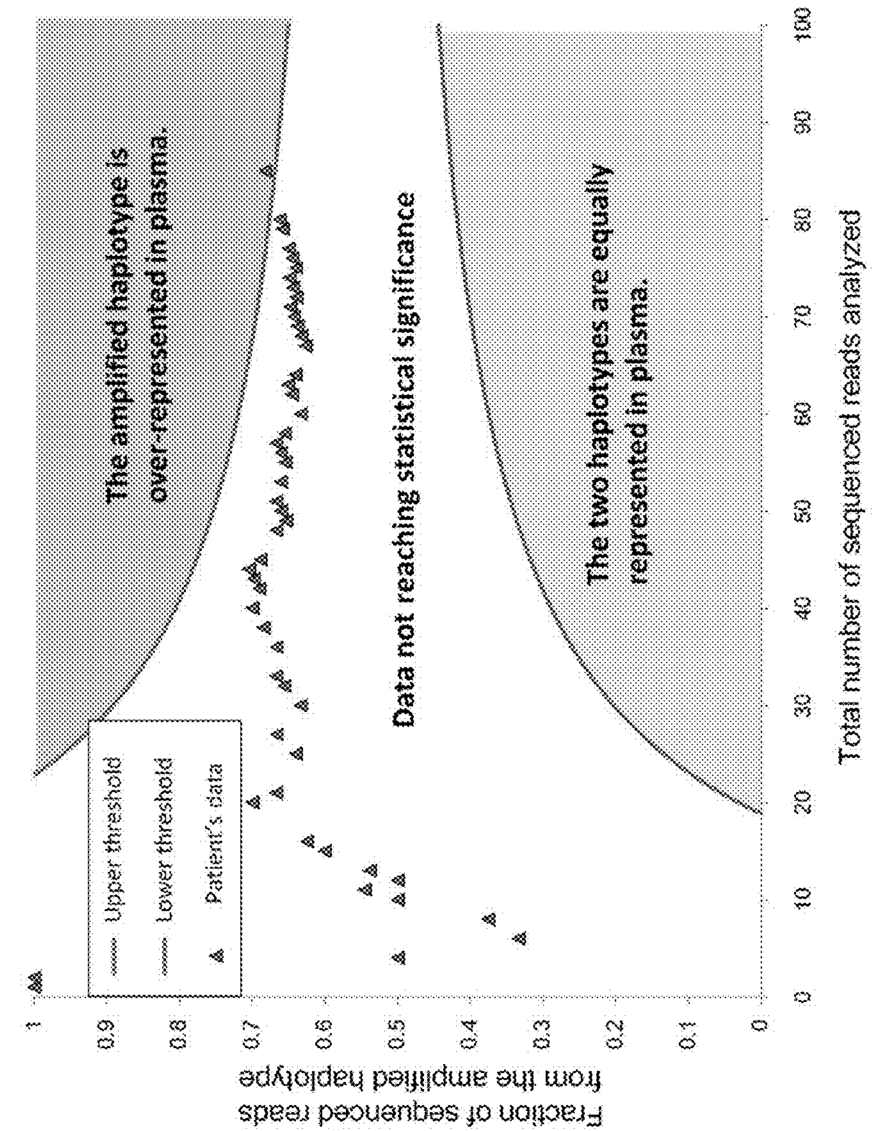
FIG. 7 shows an RHDO analysis of the plasma DNA of an hepatocellular carcinoma (HCC) patient for a segment located at chromosome 1p which showed mono-allelic amplification in the tumor tissue according to embodiments of the present invention.

FIG. 7 shows an RHDO analysis of the plasma DNA of the HCC patient for a segment located at chromosome 1p which showed mono-allelic amplification in the tumor tissue according to embodiments of the present invention. The green triangles represent the patient's data. The total number of sequenced reads increased with the increasing number of SNPs being analyzed. The fraction of the total sequenced reads from the amplified haplotype in the tumor varied with the increasing number of the total sequenced reads analyzed and eventually reached a value higher than the upper threshold. This indicates that a significant haplotype dosage imbalance and, hence, supports the presence of this cancer-associated chromosomal aberration in plasma.

RHDO analysis using SPRT was performed for all chromosomal regions of the HCC patient showing amplifications and deletions in the tumor tissue. The results are as follows for 922 segments known to have LOH and 105 segments known to have amplification. For LOH, 922 segments were classified with SPRT, and 921 of the segments were correctly identified as having haplotype dosage imbalance in plasma, to provide an accuracy of 99.99%. For mono-allelic amplification, 105 segments were classified with SPRT, and 105 of the segments were correctly identified as having haplotype dosage imbalance in plasma, to provide an accuracy of 100%.

C. Relative Haplotype Size Analysis

As an alternative to counting dosage of the fragments aligned to the two haplotypes, the size of the fragments for the respective haplotypes can be used. For example, for a particular chromosomal region, the size of the DNA fragments from one haplotype can be compared to the size of the DNA fragments of the other haplotype. One can analyze the size distribution of DNA fragments that correspond to any of the alleles at heterozygous loci of a first haplotype of the region, and compare it to the size distribution of DNA fragments that correspond to any of the alleles at the heterozygous loci of the second haplotype. A statistically significant difference in the size distribution can be used to identify an aberration, in a similar manner that the number of counts can.

It has been reported that the size distribution of the total (i.e. tumoral plus non-tumoral) plasma DNA is increased in cancer patients (Wang B G, et al. Cancer Res. 2003; 63: 3966-8). However, if one is specifically studying the tumor-derived DNA (instead of the total (i.e. tumor plus non-tumor) amount of DNA), then it has been observed that the size distribution of tumor-derived DNA molecules is shorter than that of molecules derived from non-tumor cells (Diehl et al. Proc Natl Acad Sci USA. 2005; 102:16368-73). Therefore, the size distribution of circulating DNA can be used for determining if cancer-associated chromosomal aberrations are present. The principle of the size analysis is shown in FIG. 8.

Figure 8:
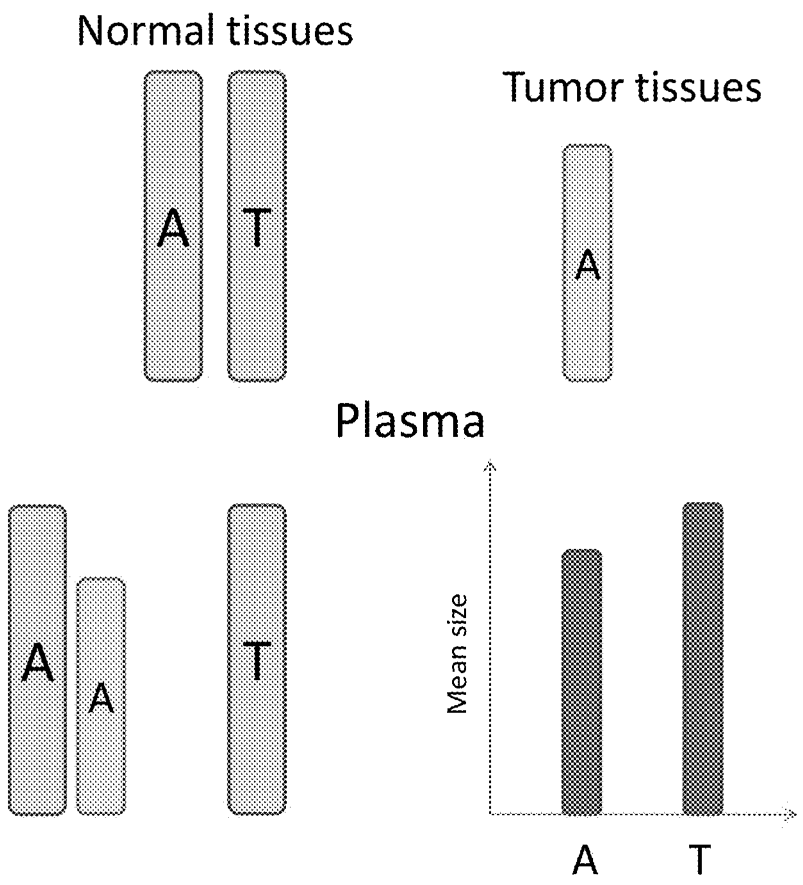
FIG. 8 shows the change in size distribution of fragments for two haplotypes of a chromosomal region when a tumor containing a deletion is present according to embodiments of the present invention.

FIG. 8 shows the change in size distribution of fragments for two haplotypes of a chromosomal region when a tumor containing a deletion is present according to embodiments of the present invention. As illustrated in FIG. 8, the T allele is deleted in the tumor tissues. As a result, the tumor tissues would only release short molecules of the A allele into the plasma. The tumor-derived short DNA molecules would lead to the overall shortening of the size distribution for the A allele in the plasma, hence, resulting in a shorter size distribution of the A allele compared with the T allele in the plasma. As discussed in the previous sections, all the alleles located on the same haplotype can be analyzed together. In other words, the size distribution for DNA molecules carrying alleles located on one haplotype can be compared with that for DNA molecules carrying alleles on the other haplotype. The deleted haplotype in the tumor tissues would show a longer size distribution in plasma.

Figure 9:
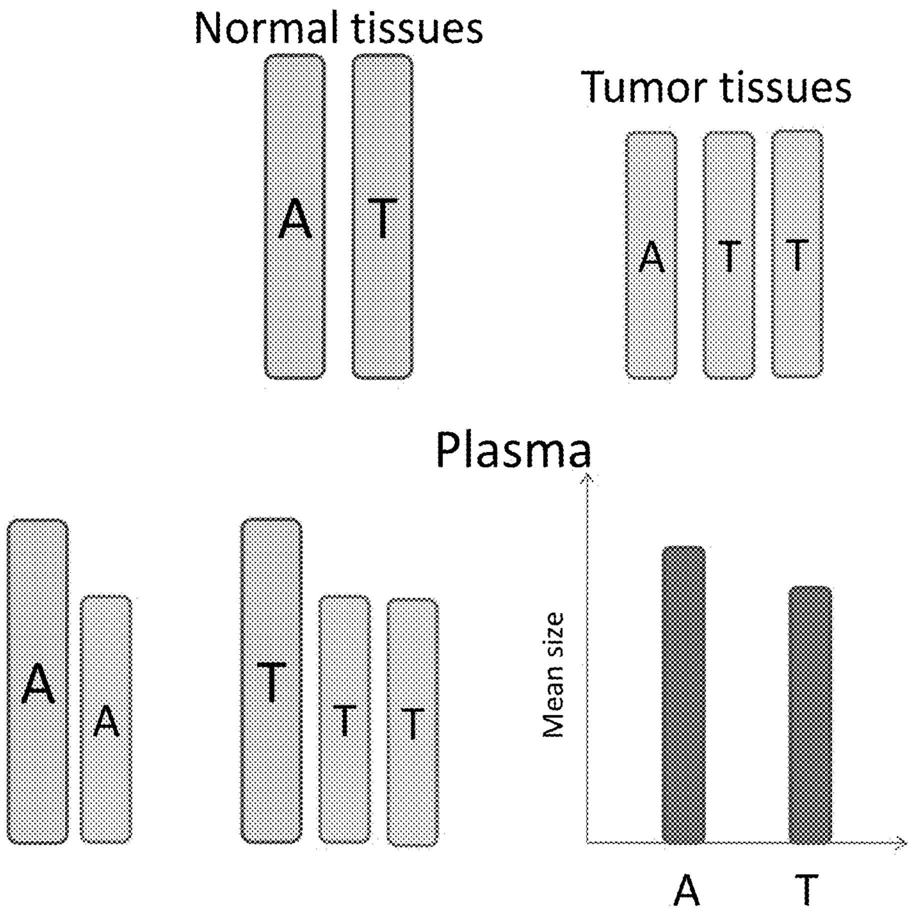
FIG. 9 shows the change in size distribution of fragments for two haplotypes of a chromosomal region when a tumor containing an amplification is present according to embodiments of the present invention.

Size analysis can also be applied for detecting amplification of chromosomal regions associated with cancer. FIG. 9 shows the change in size distribution of fragments for two haplotypes of a chromosomal region when a tumor containing an amplification is present according to embodiments of the present invention. In the example shown in FIG. 9, the chromosomal region carrying the allele T is duplicated in the tumor. As a result, increased amount of short DNA molecules carrying the T allele would be released in the plasma, hence, resulting in an overall shortening of the size distribution of the T allele compared with the size distribution of the A allele. The size analysis can be applied collectively to all the alleles located on the same haplotype. In other words, the size distribution for the haplotype amplified in the tumor tissues would be shorter than the size distribution for the haplotype not amplified in the tumor.

Detection of the Shortening of the Size Distribution of Circulating DNA

The size of the DNA fragments arising from the two haplotypes, namely Hap I and Hap II, can be determined by, but not limited to, paired-end massively parallel sequencing. After sequencing the ends of a DNA fragment, the sequenced reads (tags) can be aligned to the reference human genome. The size of the sequenced DNA molecules can be inferred from the coordinates of the outermost nucleotide at each end. The sequenced tags of the molecule can be used to determine if the sequenced DNA fragment arises from Hap I or Hap II. For example, one of the sequenced tags may include a heterozygous locus in the chromosomal region being analyzed.

Therefore, for each sequenced molecule, we can determine both the size and whether it arises from Hap I or Hap II. Based on the size of the fragments aligned to each haplotype, a computer system can calculate the size distribution profiles (e.g. an average fragment size) for both Hap I and Hap II. The size distributions of DNA fragments from Hap I and Hap II can be compared using appropriate statistical analysis to determine when the size distributions are sufficiently different to identify an aberration. Apart from paired-end massively parallel sequencing, other methods can be used for determining the size of the DNA fragments, including but not limited to, sequencing whole DNA fragments, mass spectrometry, and optical methods for observing and comparing the lengths of the observed DNA molecules to a standard.

Next, we introduce two example methods for detecting the shortening of circulating DNA associated with genetic aberrations of tumors. These two methods aim to provide a quantitative measurement of the difference in size distribution for two populations of DNA fragments. The two populations of DNA fragments refer to the DNA molecules corresponding to Hap I and Hap II.

Difference in the Fraction of Short DNA Fragments

In one implementation, a fraction of short DNA fragments is used. One sets a cutoff size (w) to define the short DNA molecules. The cutoff size can be varied and be chosen to fit different diagnostic purposes. A computer system can determine the number of molecules that are equal to or shorter than the size cutoff. The fraction of DNA fragments (Q) can then be calculated by dividing the number of short DNA by the total number of DNA fragments. The value of Q would be affected by the size distribution of the population of DNA molecules. A shorter overall size distribution signifies that a higher proportion of the DNA molecules would be short fragments, thus, giving a higher value of Q.

The difference in the fraction of short DNA fragments between Hap I and Hap II can then be used. The difference in the size distribution of DNA fragments from Hap I and Hap II can be reflected by the difference in the fraction of short fragments for Hap I and Hap II ($\Delta Q$). $\Delta Q = Q_{HapI} - Q_{HapII}$, where $Q_{HapI}$ is the fraction of short fragments for Hap I DNA fragments; and $Q_{HapII}$ is the fraction of short fragments for Hap II DNA fragments. $Q_{HapI}$ and $Q_{HapII}$ are examples of a statistical value of the two groups of the size distributions of fragments from each of the haplotypes.

As illustrated in the previous section, when Hap II is deleted in the tumor tissues, the size distribution for Hap I DNA fragments would be shorter than that for Hap II DNA fragments. As a result, a positive value of $\Delta Q$ would be observed. The positive value of $\Delta Q$ can be compared to a threshold value to determine if $\Delta Q$ is large enough for a deletion to be considered as existing. An amplification of Hap I would also show a positive value of $\Delta Q$. When there is a duplication of Hap II in the tumor tissues, the size distribution for Hap II DNA fragments would be shorter than that for Hap I DNA fragments. Hence, the value of $\Delta Q$ would become negative. In the absence of chromosomal aberration, the size distribution for Hap I and Hap II DNA fragments in plasma/serum would be similar. Hence, the value of $\Delta Q$ would be approximately zero.

The $\Delta Q$ of a patient can be compared with normal individuals to determine if the value is normal. In addition or alternatively, the $\Delta Q$ value of a patient can be compared with values obtained from patients with similar cancers to determine if the value is abnormal. Such comparison can involve comparison(s) to threshold values as described herein. In the context of disease monitoring, the value $\Delta Q$ can be monitored serially over time. The change in the value of $\Delta Q$ may indicate the increased fractional concentration of tumoral DNA in plasma/serum. In selected implementation of this technology, the fractional concentration of tumoral DNA can be correlated with tumor stage, prognostication and progression of the disease. Such implementations using measurements at different times is discussed in more detail later.

Difference in the Fraction of Total Length Contributed by Short DNA Fragments

In this implementation, the fraction of total length contributed by short DNA fragments is used. A computer system can determine the total length of a group of DNA fragments in a sample (e.g. the fragments from a particular haplotype of a given region or just from the given region). A cutoff size (w) below which the DNA fragments are defined as "short fragments" can be chosen. The cutoff size can be varied and be chosen to fit different diagnostic purposes. Then, a computer system can determine the total length of the short DNA fragments by summing up the length of the random selection of DNA fragments that are equal to or shorter than the cutoff size. The fraction of total length contributed by short DNA fragments can then be calculated as follows: $F=\Sigma^{w}length/\Sigma^{N}length$, where $\Sigma^{w}$ length represents sum of the lengths of DNA fragments with length equal to or less than w(bp); and $\Sigma^{N}$ length represents the sum of the length of DNA fragments equal to or less than a predetermined length N. In one embodiment, N is 600 bases. However, other size limits, e.g. 150 bases, 180 bases, 200 bases, 250 bases, 300 bases, 400 bases, 500 bases and 700 bases, can be used for calculating the "total length".

A value of 600 bases or below may be chosen because the Illumina Genome Analyzer system is not effective in amplifying and sequencing DNA fragments longer than 600 bases. In addition, limiting the analysis to DNA fragments of shorter than 600 bases can also avoid biases arising from structural variations of the genome. In the presence of structural variations, for example rearrangements (Kidd J M et al, Nature 2008; 453:56-64), the size of the DNA fragment can be overestimated when the size is estimated bioinformatically by mapping the ends of the DNA fragment to the reference genome. In addition, >99.9% of all the DNA fragments successfully sequenced and mapped to the reference genome are less than 600 bases and, thus, including all fragments equal to and shorter than 600 bases would provide a representative estimation of the size distribution of the DNA fragments in the sample.

Accordingly, the difference in the fractions of total length contributed by short DNA fragments between Hap I and Hap II can be used. The perturbation in the size distribution between Hap I and Hap II DNA fragments can be reflected by the difference in their F values. Here we define $F_{Hap\ I}$ and $F_{Hap\ II}$ as the fractions of total length contributed by short DNA fragments for Hap I and Hap II, respectively. The difference in the fractions of total length contributed by short DNA fragments between Hap I and Hap II (ΔF) can be calculated as: $\Delta F=F_{Hap\ I}-F_{Hap\ II}$. $F_{HapI}$ and $F_{HapII}$ are examples of a statistical value of the two groups of the size distributions of fragments from each of the haplotypes.

Similar to embodiments illustrated in the previous section, the deletion of Hap II in the tumor tissues would lead to the apparent shortening of the size distribution for Hap I DNA fragments when compared with Hap II DNA fragments. This would lead to a positive value of ΔF. When Hap II is duplicated, a negative ΔF value would be observed. In the absence of chromosomal aberration, the value of ΔF would be approximately zero.

The ΔF of a patient can be compared with normal individuals to determine if the value is normal. The ΔF of a patient can be compared with values obtained from patients with similar cancers to determine if the value is abnormal. Such comparison can involve comparison(s) to threshold values as described herein. In the context of disease monitoring, the value ΔQ can be monitored serially. The change in the value of ΔF may indicate the increased fractional concentration of tumoral DNA in plasma/serum.

D. General Method

Figure 10:
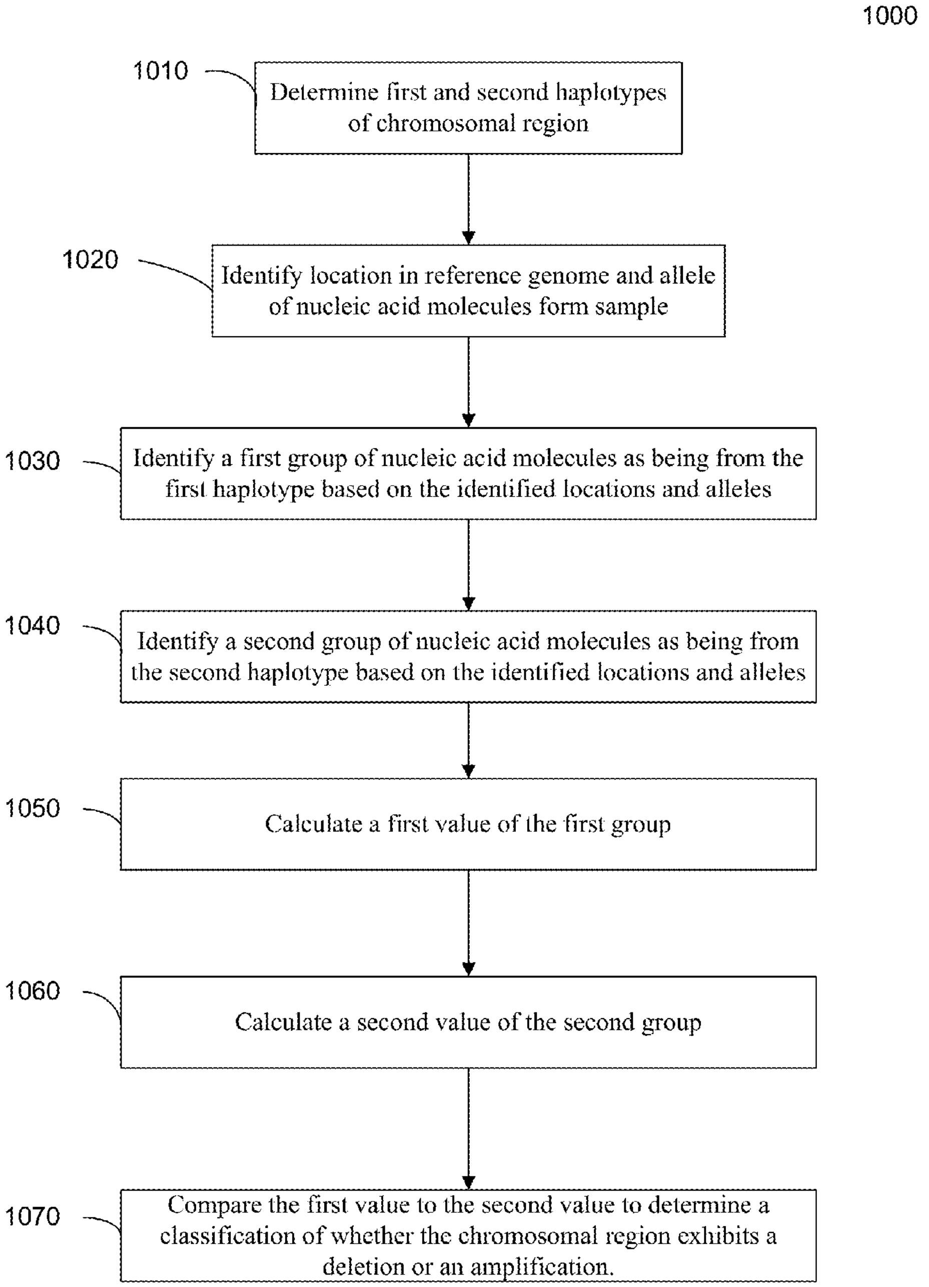
FIG. 10 is a flowchart illustrating a method of analyzing the haplotypes of a biological sample of an organism to determine whether a chromosomal region exhibits a deletion or an amplification according to embodiments of the present invention.

FIG. 10 is a flowchart illustrating a method of analyzing the haplotypes of a biological sample of an organism to determine whether a chromosomal region exhibits a deletion or an amplification according to embodiments of the present invention. The biological sample includes nucleic acid molecules (also called fragments) originating from normal cells and potentially from cells associated with cancer. These molecules may be cell-free in the sample. The organism can be of any type that has more than one copy of a chromosome, i.e., at least diploid organisms, but can include higher polyploid organisms.

In one embodiment of this and any other method described herein, the biological sample includes cell-free DNA fragments. Although the analysis of plasma DNA has been used to illustrate the different methods described in this application, these methods can also be applied to detect tumor-associated chromosomal aberrations in samples containing a mixture of normal and tumor-derived DNA. The other sample types include saliva, tears, pleural fluid, ascitic fluid, bile, urine, serum, pancreatic juice, stool and cervical smear samples In step 1010, first and second haplotypes are determined for normal cells of the organism at a first chromosomal region. The haplotypes can be determined by any suitable method, such as those mentioned herein. The chromosomal region may be selected via any method, e.g., methods described herein. The first chromosomal region includes a first plurality of loci (e.g., loci 420 of region 410) that are heterozygous. The heterozygous loci (hets) may be far apart from each other, e.g., the loci can be 500 or 1000 bases (or more) apart from another locus of the first plurality of loci. Other hets may exist in the first chromosomal region, but not be used.

In step 1020, a plurality of nucleic acid molecules in the biological sample are characterized regarding location and allele of each molecule. For instance, a location of a nucleic acid molecule in a reference genome of the organism can be identified. This locating can be performed in various ways, including performing a sequencing of a molecule (e.g. via universal sequencing), to obtain one or two (paired-end) sequenced tags of the molecule and then aligning the sequenced tag(s) to the reference genome. Such alignment can be performed using such as tools as basic local alignment search tool (BLAST). The location can be identified as a number in an arm of a chromosome. The allele at one of the heterozygous loci (hets) can be used to determine which haplotype a fragment is from.

In step 1030, a first group of nucleic acid molecules are identified as being from the first haplotype based on the identified locations and determined alleles. For example, a fragment including loci 421 of FIG. 4 having allele A would be identified as being from Hap I. The first group can span the first chromosomal region by including at least one nucleic acid molecule located at each of the first plurality of loci.

In step 1040, a second group of nucleic acid molecules are identified as being from the second haplotype based on the identified locations and determined alleles. For example, a fragment including loci 421 of FIG. 4 having allele T would be identified as being from Hap II. The second group includes at least one nucleic acid molecule located at each of the first plurality of loci.

In step 1050, a computer system calculates a first value of the first group of nucleic acid molecules. The first value defining a property of the nucleic acid molecules of the first group. Examples of the first value include a tag count of the number of molecules in the first group and a size distribution of the molecules in the first group.

In step 1060, the computer system calculates a second value of the second group of nucleic acid molecules. The second value defining a property of the nucleic acid molecules of the second group.

In step 1070, the first value is compared to the second value to determine a classification of whether the first chromosomal region exhibits a deletion or an amplification. A classification of a deletion or amplification existing can provide information about the organism having cells associated with cancer. Examples of a comparison include taking a difference or ratio of the two values and comparing the result to one or more threshold values, as is described herein. For example, a ratio can be compared to the threshold values in an SPRT analysis. Example classifications can include positive (i.e. amplification or deletion detected), negative, and unclassified, as well as varying degrees of positive and negative (e.g., using integer numbers between 1 and 10, or real number between 0 and 1). The amplification can include simple duplication. Such a method can detecting the presence of cancer-associated nucleic acids, which include tumor DNA and DNA from preneoplastic lesions, i.e. precurors of cancer.

E. Depth

The depth of analysis refers to the amount of molecules that need to be analyzed to provide a classification or other determination within a specified accuracy. In one embodiment, the depth may be calculated based on a known aberration, and then a measurement and analysis with that depth may be performed. In another embodiment, the analysis may continue until a classification is made, and the depth at which the classification is made can be used to determine a level of cancer (e.g., a stage of the cancer or a size of a tumor). The following provides examples of some calculations involving depth.

A deviation can refer to any difference or ratio as described herein. As example, the deviation can be between the first and second value or of a parameter from a threshold or the tumor concentration, as described herein. If a deviation doubles, then the number of fragments that need to be measured decreases by ¼. More generally, if the deviation increases by a factor of N, the number of fragments that need to be measured is $1/N^2$. As a corollary, if the deviation decreases by 1/N, then the number of fragments to be tested increases by $N^2$. N can be a real number or an integer.

Suppose a case where the tumor DNA is 10% of the sample (e.g. plasma), and assume that a statistically significant difference is seen from sequencing 10 million fragments. Then say for example, an enrichment procedure is performed so there is now 20% of tumoral DNA in the sample, then the number of fragments needed would be 2,500,000 fragments. In this manner, the depth can be correlated to the percentage of tumor DNA in the sample.

The amount of amplification will also affect the depth. For a region that has twice the amount of copies in that region (e.g. 4 as opposed to the normal 2), suppose X number of fragments are required to be analyzed. If a region has 4 times the amount of normal copies, then this region will require X/4 amount of fragments.

F. Thresholds

The amount of a deviation of a parameter (e.g. difference or ratio of values for each haplotype) from normal values can be used to provide a diagnosis, as is described above. For example, the deviation may be the difference of the average size of the fragments from one haplotype of a region to the average size of the fragments from the other haplotype. If the deviation is above a certain amount (e.g., threshold as determined from normal samples and/or regions), then a deletion or amplification is identified. But, the extent above the threshold can be informative, which can lead to the use of multiple thresholds, each corresponding to a different level of cancer. For example, a higher deviation from normal can provide what stage the cancer is at (e.g. stage 4 would have a higher degree of imbalance than stage 3). A higher deviation can also be the result of the tumor being large and thus releasing many fragments, and/or that the region is amplified many times.

In addition to providing different levels of cancer, varying thresholds can also allow for efficient detection of regions with aberration or of specific regions. For example, one can set high thresholds to look mainly for amplifications of three times and higher, which would give a greater imbalance than deletions of one haplotype. Deletions of two copies of region can also be detected. Also, a lower threshold can be used to identify regions that might have an aberration, and then these regions can be analyzed further to confirm whether an aberration does exist and the location. For example, a binary search (or a search of higher order, such as an octree) can be performed, with lower levels in the hierarchy using higher thresholds.

Figure 11:
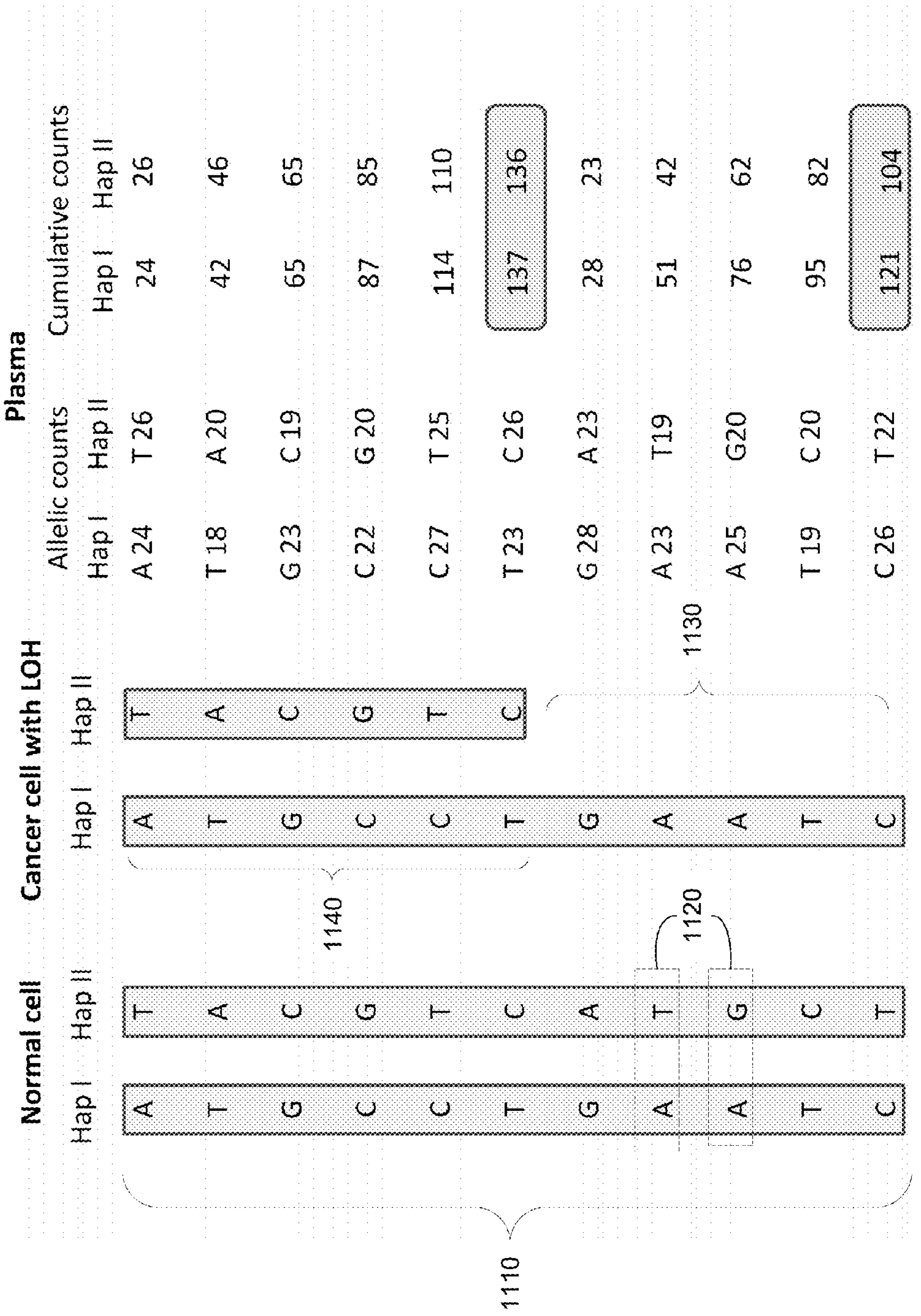
FIG. 11 shows a region 1110 with a subregion 1130 being deleted in cancer cells along with measurements made in plasma to determine the deleted region according to embodiments of the present invention. (Hap I (SEQ ID NO:1) and Hap II (SEQ ID NO:2))

FIG. 11 shows a region 1110 with a subregion 1130 being deleted in cancer cells along with measurements made in plasma to determine the deleted region according to embodiments of the present invention. The chromosomal region 1110 may be selected by any method mentioned herein, such as by splitting up a genome into equal sized segments. FIG. 11 also shows the number of allelic counts for each of the loci 1120. A cumulative total is also kept for region 1140 (normal region) and region 1130 (deleted region), respectively.

If region 1110 is chosen for analysis, the number cumulative counts are 258 for Hap I and 240 for Hap II providing a difference of 18 over eleven loci. Such a difference is smaller as a percentage of the total number of counts, than just if the deleted subregion 1130 were analyzed. This makes sense as about half of region 1110 is normal, whereas all of subregion 1130 is deleted in the cancer cell. Thus, an aberration in region 1110 could be missed depending on the threshold used.

To allow for detection of deletions of subregions, embodiments can use a lower threshold for relatively large regions (for this example region 1110 is assumed to be relatively large compared to the size of deleted regions to be identified). A lower threshold would identify more regions, which could include some false positives, but it would reduce the false negatives. Now, the false positives could be removed through further analysis, which can also pinpoint the aberration.

Once a region has been flagged for further analysis, the region can be divided into subregions for further analysis. In FIG. 11, one can split the eleven loci in half (e.g. using a binary tree) to provide subregions 1140 of six loci and subregion 1130 with five loci. These regions could be analyzed with a same threshold value or a more stringent threshold value. In this example, subregion 1140 would then be identified as being normal and subregion 1130 identified as including a deletion or amplification. In this manner, larger regions can be dismissed as having no aberration, and time can be spent further analyzing suspected regions (regions above a lower threshold) to identify subregions that show an aberration with high confidence (e.g. using a higher threshold). Although RHDO was used here, size techniques are equally applicable.

The size of the regions for the first level of search (and size of subregions of lower levels in the tree) can be chosen based on the size of aberrations to be detected. Cancers have been found to show ten regions with aberrations of 10 MB length. Patients have also had 100 MB regions exhibiting aberration. Later stages of cancer may have longer sections of aberration.

G. Refinement of Location of Aberration within a Region

In the last section, division of a region into subregions based on a tree search was discussed. Here, we discuss other methods for analyzing subregions, and to pinpoint the aberration within a region.

Figure 12:
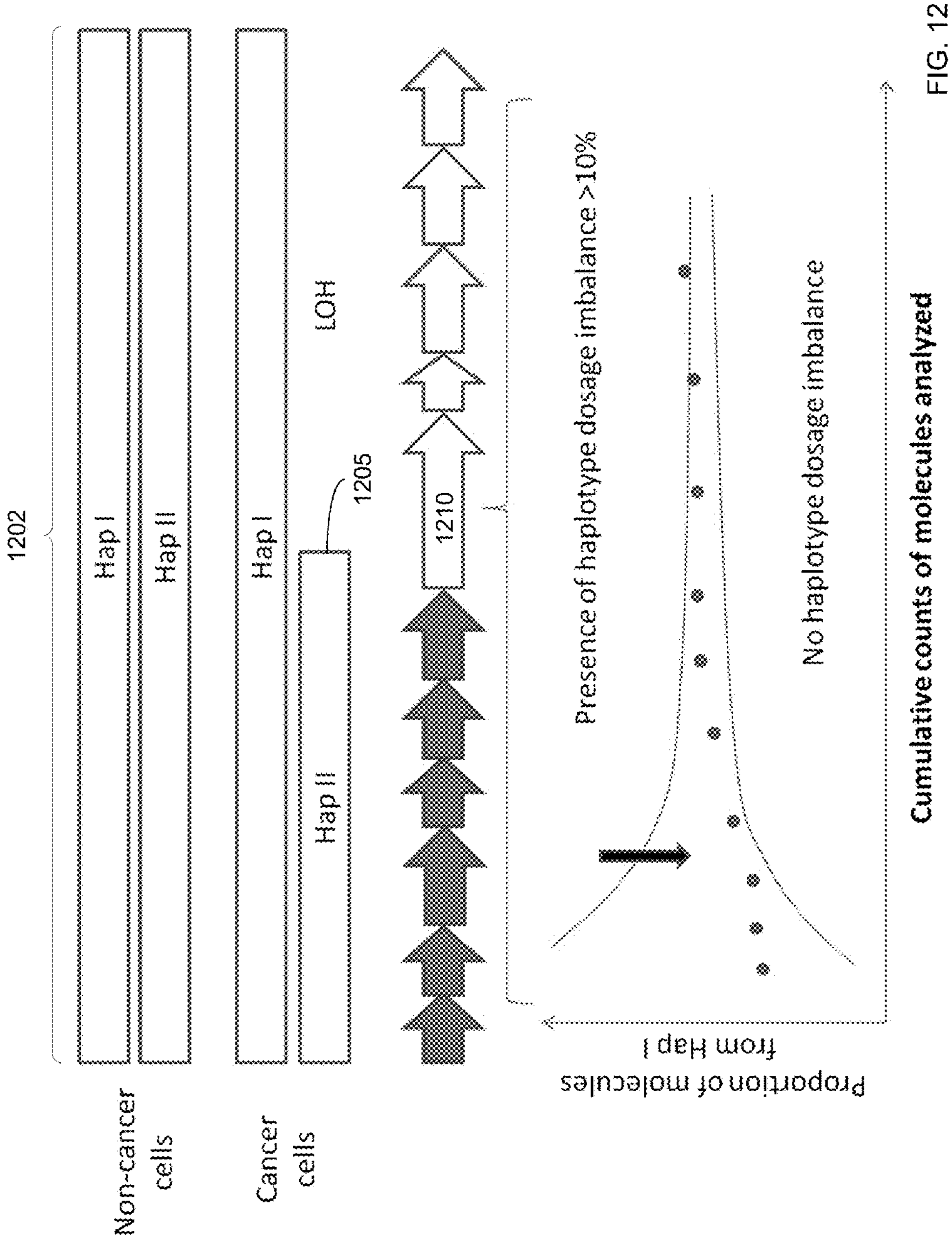
FIG. 12 shows how the location of the aberrations can be mapped using RHDO analysis according to embodiments of the present invention.

FIG. 12 shows how the location of the aberrations can be mapped using RHDO analysis according to embodiments of the present invention. The chromosomal region is shown horizontally, with the haplotypes of the non-cancer cells labeled Hap I and Hap II. The deleted region of Hap II in the cancer cells is labeled as LOH.

As shown, RHDO analysis is started from the left side to the right side of the hypothetical chromosome region 1202. Each of the arrows represents a RHDO classification segment. Each segment can be considered its own region, specifically a subregion with a subset of the hets of the larger region. The size of a RHDO classification segment is dependent on the number of loci (and positions of the loci) before a classification can be determined. The number of loci included in each RHDO segment is dependent on the number of molecules analyzed for each segment, the desired accuracy (e.g. the odds ratio in SPRT analysis), and the fractional concentration of tumor-derived DNA in the sample. A classification would be made when the number of molecules is adequate to determine that a statistically significant difference is present between the two haplotypes as in the example illustrated in FIG. 4 and FIG. 5.

Each of the solid horizontal arrows represents a RHDO classification segment showing that haplotype dosage imbalance is absent in the DNA sample. Within the region without a LOH in the tumor, six RHDO classifications are made and each indicates the absence of haplotype dosage imbalance. The next RHDO classification segment 1210 crosses the junction 1205 between the regions with and without LOH. In the lower part of FIG. 12, the SPRT curve for RHDO segment 1210 is shown. The black vertical arrow indicates the junction between the regions with and without LOH. With the accumulation of increasing data from the region with LOH, the RHDO classification of this segment indicates the presence of haplotype dosage imbalance.

Each of the white horizontal arrows represents a RHDO classification segment that indicates the presence of haplotype dosage imbalance. The subsequent four RHDO on the right side also indicate the presence of haplotype dosage imbalance in the DNA sample. The location of the junction between regions with and without LOH can be deduced to be within the first RHDO segment that show a change in the RHDO classification, namely from the presence to absence of haplotype dosage imbalance or vice versa.

Figure 13:
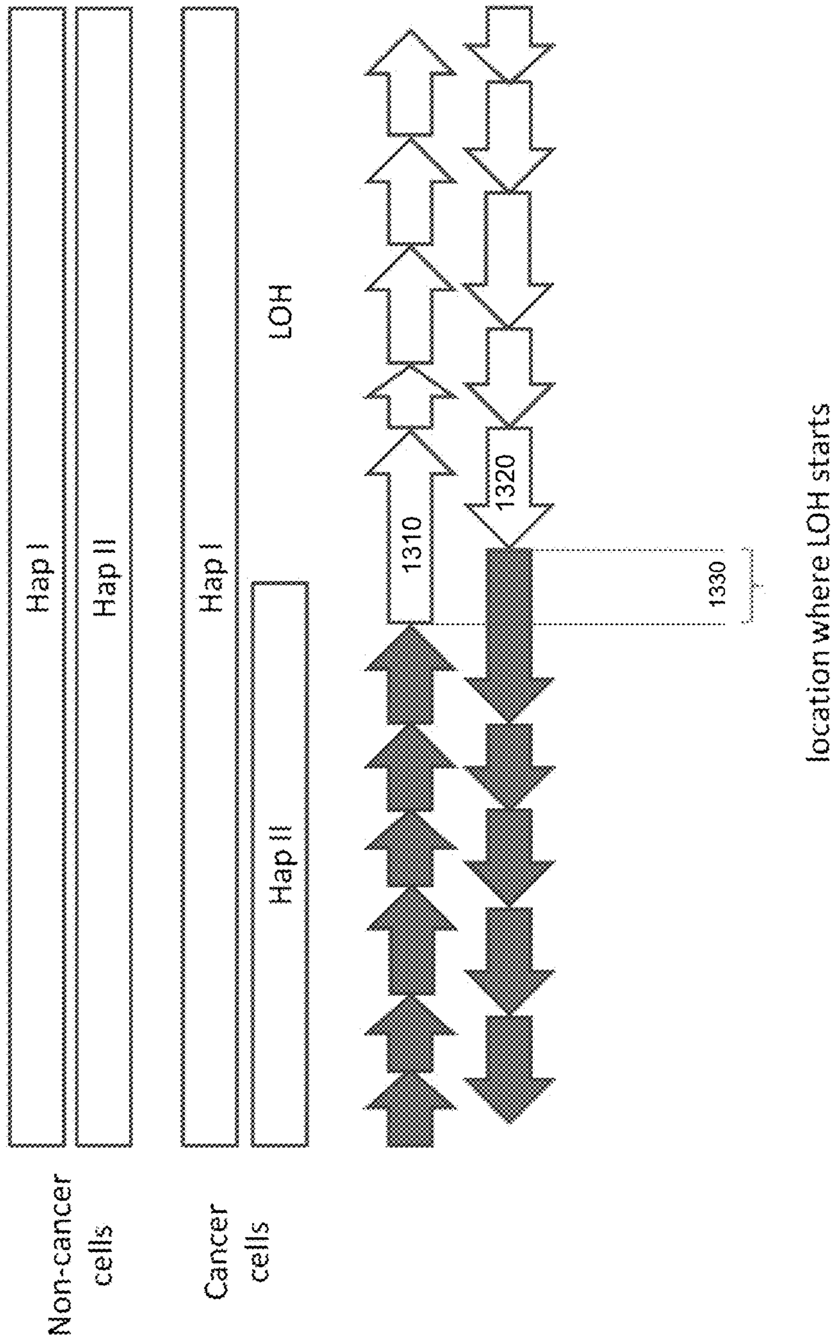
FIG. 13 shows an RHDO classification started from another direction according to embodiments of the present invention.

FIG. 13 shows a RHDO classification started from another direction according to embodiments of the present invention. In FIG. 13, RHDO classifications from both directions are shown. From the RHDO analysis starting from the left side, the junction between the regions with and without LOH can be deduced to be within the first RHDO segment 1310 showing the presence of haplotype dosage imbalance. From the RHDO analysis starting from the right side, the junction can be deduced to be within the first RHDO segment 1320 that indicates the absence of haplotype dosage imbalance. Combining the information from the RHDO analysis conducted in the two directions, the location 1330 of the junction between the regions with and without LOH can be deduced.

IV. NON-SPECIFIC HAPLOTYPE DETECTION OF ABERRATIONS

The RHDO method relies on using heterozygous loci. Now, the chromosomes of a diploid organism will have some differences, resulting in two haplotypes, but the number of heterozygous loci can vary. Some individuals may have relatively few heterozygous loci. The embodiment described in this section can also be used for loci that are homozygous by comparing two regions and not two haplotypes of the same region. Thus, more data points may be obtained, although some drawbacks may exist from the comparison to two different chromosomal regions.

In a relative chromosomal region dosage method, the number of fragments from one chromosomal region (e.g., as determined by counting the sequenced tags aligned to that region) is compared to an expected value (which may be from a reference chromosome region or from the same region in another sample that is known to be healthy). In this manner, a fragment would be counted for a chromosomal region regardless of which haplotype the sequenced tag is from. Thus, sequenced tags that contain no hets could still be used. To perform the comparison, an embodiment can normalize the tag count before the comparison. Each region is defined by at least two loci (which are separated from each other), and fragments at these loci can be used to obtain a collective value about the region.

A normalized value for the sequenced reads (tags) for a particular region can be calculated by dividing the number of sequenced reads aligning to that region by the total number of sequenced reads alignable to the whole genome. This normalized tag count allows results from one sample to be compared to the results of another sample. For example, the normalized value can be the proportion (e.g., percentage or fraction) of sequenced reads expected to be from the particular region, as is stated above. But, many other normalizations are possible, as would be apparent to one skilled in the art. For example, one can normalize by dividing the number of counts for one region by the number of counts for a reference region (in the case above, the reference region is just the whole genome). This normalized tag count can then be compared against a threshold value, which may be determined from one or more reference samples not exhibiting cancer.

The normalized tag count of the tested case would then be compared with the normalized tag count of one or more reference subjects, e.g. those without cancer. In one embodiment, the comparison is made by calculating the z-score of the case for the particular chromosomal region. The z-score is calculated using the following equation: z-score=(normalized tag count of the case−mean)/S.D., where "mean" is the mean normalized tag count aligning to the particular chromosomal region for the reference samples; and S.D. is the standard deviation of the number of normalized tag count aligning to the particular region for the reference samples.

Hence, the z-score is the number of standard deviation that the normalized tag count of a chromosomal region for the tested case is away from the mean normalized tag count for the same chromosomal region of the one or more reference subjects.

In the situation when the tested organism has a cancer, the chromosomal regions that are amplified in the tumor tissues would be over-represented in the plasma DNA. This would result in a positive value of the z-score. On the other hand, chromosomal regions that are deleted in the tumor tissues would be under-represented in the plasma DNA. This would result in a negative value of the z-score. The magnitude of the z-score is determined by several factors.

One factor is the fractional concentration of tumor-derived DNA in the biological sample (e.g. plasma). The higher the fractional concentration of tumor-derived DNA in the sample (e.g. plasma), the larger the difference between the normalized tag count of the tested case and the reference cases would be. Hence, a larger magnitude of the z-score would result.

Another factor is the variation of the normalized tag count in the one or more reference cases. With the same degree of the over-representation of the chromosomal region in the biological sample (e.g. plasma) of the tested case, a smaller variation (i.e. a smaller standard deviation) of the normalized tag count in the reference group would result in a higher z-score. Similarly, with the same degree of under-representation of the chromosomal region in the biological sample (e.g. plasma) of the tested case, a smaller standard deviation of the normalized tag count in the reference group would result in a more negative z-score.

Another factor is the magnitude of chromosomal aberration in the tumor tissues. The magnitude of chromosomal aberration refers to the copy number changes for the particular chromosomal region (either gain or loss). The higher the copy number changes in the tumor tissues, the degree of over- or under-representation of the particular chromosomal region in the plasma DNA would be higher. For example, the loss of both copies of the chromosome would result in greater under-representation of the chromosomal region in the plasma DNA than the loss of one of the two copies of the chromosome and, hence, resulted in a more negative z-score. Typically, there are multiple chromosomal aberrations in cancers. The chromosomal aberrations in each cancer can further vary by its nature (i.e. amplification or deletion), its degree (single or multiple copy gain or loss) and its extent (size of the aberration in terms of chromosomal length).

The precision of measuring the normalized tag count is affected by the number of molecules analyzed. We expect that 15,000, 60,000 and 240,000 molecules would need to be analyzed to detect chromosomal aberrations with one copy change (either gain or loss) when the fractional concentration is approximately 12.5%, 6.3% and 3.2% respectively. Further details of the tag counting for detection of cancer for different chromosomal regions is described in U.S. Patent Publication No. 2009/0029377 entitled "Diagnosing Fetal Chromosomal Aneuploidy Using Massively Parallel Genomic Sequencing" by Lo et al., the entire contents of which are herein incorporated by reference for all purposes.

Embodiments can also use size analysis, instead of the tag counting method. Size analysis may also be used, instead of a normalized tag count. The size analysis can use various parameters, as mentioned herein, and in U.S. patent application Ser. No. 12/940,992. For example, the Q or F values from above may be used. Such size values do not need a normalization by counts from other regions as these values do not scale with the number of reads. Techniques of the haplotype-specific methods can be used for the non-specific methods as well. For example, techniques involving the depth and refinement of a region may be used. In some embodiments, a GC bias for a particular region can be taken into account when comparing two regions. Since the RHDO method uses the same region, such a correction is not needed.

V. MULTIPLE REGIONS

Although certain cancers can typically present with aberrations in particular chromosomal regions, such cancers do not always present in only the same regions. For example, additional chromosomal regions could show aberrations, and the location of such additional regions may be unknown. Furthermore, when screening patients to identify early stages of cancer, one may want to identify a broad range of cancers, which could show aberrations present throughout the genome. To address these situations, embodiments can analyze a plurality of regions in a systematic fashion to determine which regions show aberrations. The number of aberrations and their location (e.g. whether they are contiguous) can be used, for example, to confirm aberrations, determine a stage of the cancer, provide a diagnosis of cancer (e.g. if the number is greater than a threshold value), and provide a prognosis based on the number and location of various regions exhibiting an aberration.

Accordingly, embodiments can identify whether an organism has cancer based on the number of regions that show an aberration. Thus, one can test a plurality of regions (e.g., 3000) to identify a number of regions that exhibit an aberration. The regions may cover the entire genome or just parts of the genome, e.g., non-repeat region.

Figure 14:
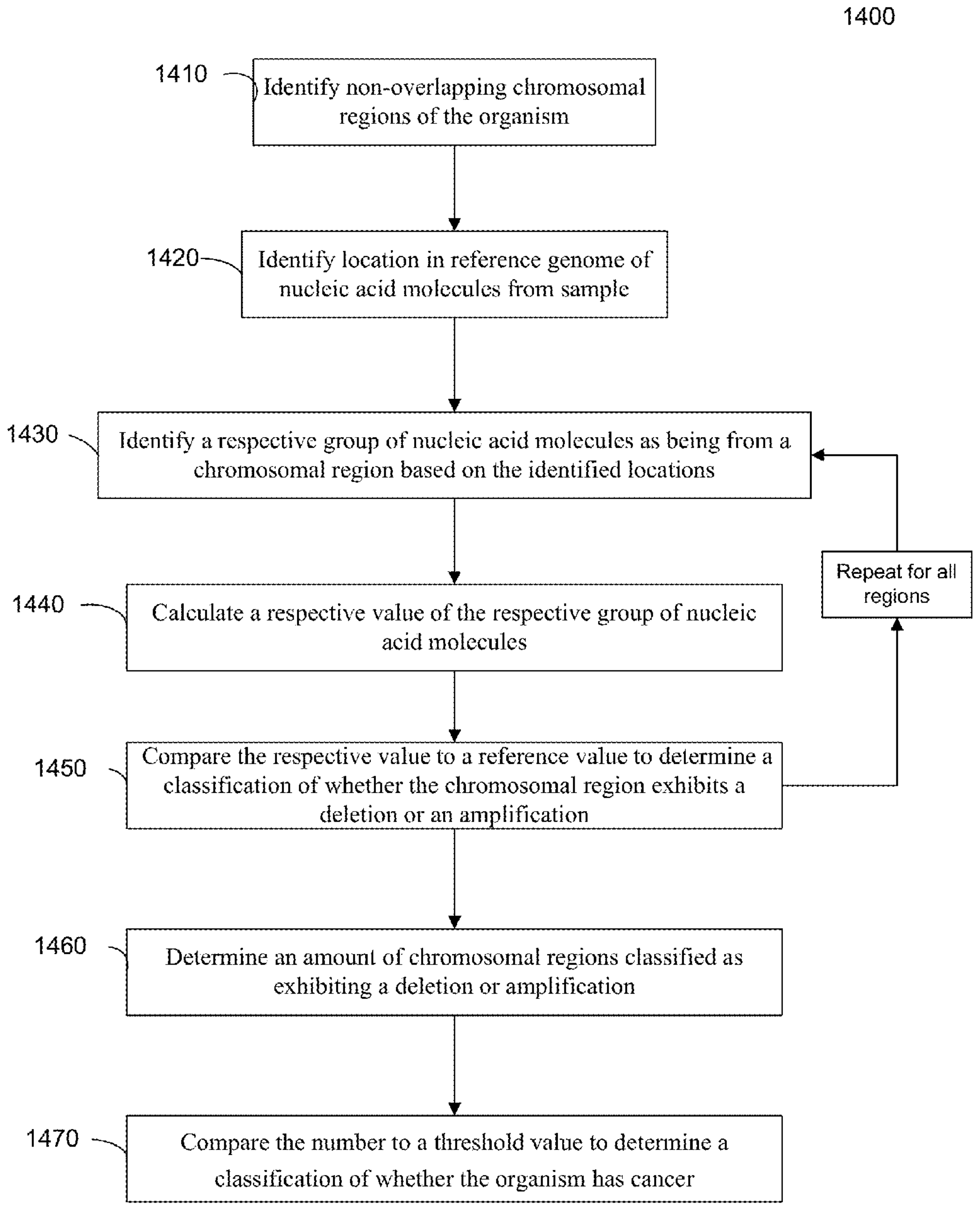
FIG. 14 is a flowchart of a method 1400 for analyzing a biological sample of an organism using a plurality of chromosomal regions according to embodiments of the present invention.

FIG. 14 is a flowchart of a method 1400 for analyzing a biological sample of an organism using a plurality of chromosomal regions according to embodiments of the present invention. The biological sample includes nucleic acid molecules (also called fragments).

In step 1410, a plurality of non-overlapping chromosomal regions of the organism are identified. Each chromosomal region includes a plurality of loci. As mentioned above, a region can be 1 Mb in size, or some other equal-size. The entire genome can then include about 3,000 regions, each of predetermined size and location. Also, as mentioned above, such predetermined regions can vary to accommodate a length of a particular chromosome or a specified number of regions to be used, and any other criteria mentioned herein. If regions have different lengths, such lengths can be used to normalize results, e.g., as described herein.

In step 1420, a location of the nucleic acid molecule in a reference genome of the organism is identified for each of a plurality of nucleic acid molecules. The location may be determined in any of the ways mentioned herein, e.g., by sequencing the fragments to obtain sequenced tags and aligning the sequenced tags to the reference genome. A particular haplotype of a molecule can also be determined for the haplotype-specific methods.

Steps 1430-1450 are performed for each of the chromosomal regions. In step 1430, a respective group of nucleic acid molecules is identified as being from the chromosomal region based on the identified locations. The respective group includes at least one nucleic acid molecule located at each of the plurality of loci of the chromosomal region. In one embodiment, the group can be fragments that align to a particular haplotype of the chromosomal region, e.g., as in the RHDO method above. In another embodiment, the group can be of any fragment that aligns to the chromosomal region, as in the methods described in section IV.

In step 1440, a computer system calculates a respective value of the respective group of nucleic acid molecules. The respective value defines a property of the nucleic acid molecules of the respective group. The respective value can be any of the values mentioned herein. For example, the value can be the number of fragments in the group or a statistical value of a size distribution of the fragments in the group. The respective value can also be a normalized value, e.g., a tag count of the region divided the total number of tag counts for the sample or the number of tag counts for a reference region. The respective value can also be a difference or ratio from another value (e.g., in RHDO), thereby providing the property of a difference for the region.

In step 1450, the respective value is compared to a reference value to determine a classification of whether the first chromosomal region exhibits a deletion or an amplification. This reference value can be any threshold or reference value described herein. For example, the reference value could be a threshold value determined for normal samples. For RHDO, the respective value could be the difference or ratio of tag counts for the two haplotypes, and the reference value can be a threshold for determining that a statistically significant deviation exists. As another example, the reference value could be the tag count or size value for another haplotype or region, and the comparison can include taking a difference or ratio (or function of such) and then determining if the difference or ratio is greater than a threshold value.

The reference value can vary based on the results of other regions. For example, if neighboring regions also show a deviation (although small compared to one threshold, e.g., a z-score of 3), then a lower threshold can be used. For example, if three consecutive regions are all above a first threshold, then cancer may be more likely. Thus, this first threshold may be lower than another threshold that is required to identify cancer from non-consecutive regions. Having three regions (or more than three) having even a small deviation can have a low enough probability of a chance effect that the sensitivity and specificity can be preserved.

In step 1460, an amount of chromosomal regions classified as exhibiting a deletion or amplification is determined. The chromosomal regions that are counted can have restrictions. For example, only regions that are contiguous with at least one other region may be counted (or contiguous regions can be required to be of a certain size, e.g., 4 or more regions). For embodiments where the regions are not equal, the number can also account for the respective lengths (e.g., the number could be a total length of the aberrant regions).

In step 1470, the amount is compared to an amount threshold value to determine a classification of the sample. As examples, the classification can be whether the organism has cancer, a stage of the cancer, and a prognosis of the cancer. In one embodiment, all aberrant regions are counted and a single threshold value is used regardless of where the regions appear. In another embodiment, a threshold value can vary based on the locations and size of the regions that are counted. For example, the amount of regions on a particular chromosome or arm of a chromosome may be compared to a threshold for that particular chromosome (or arm). Multiple thresholds may be used. For instance, the amount of aberrant regions on a particular chromosome (or arm) must be greater than a first threshold value, and the total amount of aberrant regions in the genome must be greater than a second threshold value.

This threshold value for the amount of regions can also depend on how strong the imbalance is for the regions counted. For example, the amount of regions that are used as the threshold for determining a classification of cancer can depend on the specificity and sensitivity (aberrant threshold) used to detect an aberration in each region. For example, if the aberrant threshold is low (e.g. z-score of 2), then the amount threshold may be selected to be high (e.g., 150). But, if the aberrant threshold is high (e.g., a z-score of 3), then the amount threshold may be lower (e.g., 50). The amount of regions showing an aberration can also be a weighted value, e.g., one region that shows a high imbalance can be weighted higher than a region that just shows a little imbalance (i.e. there are more classifications than just positive and negative for the aberration).

Accordingly, the amount (which may include number and/or size) of chromosomal regions showing significant over- or under-representation of a normalized tag count (or other respective value for the property of the group) can be used for reflecting the severity of disease. The amount of chromosomal regions with an aberrant normalized tag count can be determined by two factors, namely the number (or size) of chromosomal aberrations in the tumor tissues and the fractional concentration of tumor-derived DNA in the biological sample (e.g. plasma). More advanced cancers tend to exhibit more (and larger) chromosomal aberrations. Hence, more cancer-associated chromosomal aberrations would potentially be detectable in the sample (e.g. plasma). In patients with more advanced cancer, the higher tumor load would lead to a higher fractional concentration of tumor-derived DNA in the plasma. As a result, the tumor-associated chromosomal aberrations would be more easily detected in the plasma sample.

In the context of cancer screening or detection, the amount of chromosomal regions exhibiting over- or under-representation of normalized tag count (or other value) can be used to determine the possibility of the tested subject of having cancer. Using a cutoff of ±2 (i.e. z-score>2 or <−2), approximately 5% of the tested regions would be expected to give a z-score significantly deviating from the mean of the control subjects due to chance alone. When the whole genome is divided into 1 Mb segments, there would be approximately 3,000 segments for the whole genome. Thus, approximately 150 segments would be expected to have a z-score of >2 or <−2.

Thus, a cutoff (threshold) value of 150 for the number of segments with z-score >2 or <−2 can be used to determine if a cancer is present. Other cutoff values for the number of segments with aberration z-score (e.g., 100, 125, 175, 200, 250 and 300) can be chosen to fit the diagnostic purpose. A lower cutoff value, e.g. 100, would result in a more sensitive test but lower specificity and a higher cutoff value would be more specific but less sensitive. The number of false-positive classifications can be reduced by increasing the cutoff values of the z-score. For example, if the cutoff value is increased to 3, then only 0.3% of the segments would be falsely positive. In this situation, more than 3 segments with aberrant z-score can be used to indicate the presence of cancer. Other cutoff values can also be chosen, e.g. 1, 2, 4, 5, 10, 20 and 30, to fit different diagnostic purposes. However, the sensitivity of detecting the cancer-associated chromosomal aberrations would decrease with increasing the number of aberrant segments required for making a diagnosis.

One possible approach for improving the sensitivity without sacrificing the specificity is to take into account the result of the adjacent chromosomal segment. In one embodiment, the cutoff for the z-score remains to be >2 and <−2.

However, a chromosomal region would be classified as potentially aberrant only when two consecutive segments would show the same type of aberrations, e.g. both segments have a z-score of >2. If the deviation of normalized tag count is a random error, the probability of having two consecutive segments being falsely positive in the same direction would be 0.125% (5%×5%/2). On the other hand, if a chromosomal aberration encompasses two consecutive segments, the lower cutoff value would make the detection of the over- or under-representation of the segments in the plasma sample more sensitive. As the deviation of the normalized tag count (or other value) from the mean of the control subjects is not due to random error, the consecutive classification requirement would not have significant adverse effect on the sensitivity. In other embodiments, the z-score of neighboring segments can be added together using a higher cutoff value. For example, the z-scores of three consecutive segments can be summed and a cutoff value of 5 can be used. This concept can be extended to more than three consecutive segments.

The combination of amount and aberrant thresholds can also depend on the purpose of the analysis, and any prior knowledge of the organism (or lack thereof). For example, if screening a normal healthy population for cancer, then one would typically use high specificity, potentially in both the amount of regions (i.e. high threshold for the number of regions) and an aberrant threshold for when a region is identified as having an aberration. But, in a patient with higher risk (e.g. a patient complaining of a lump or family history, smoker, HPV virus, hepatitis virus, or other viruses) then the thresholds could be lower in order to have more sensitivity (less false negatives).

In one embodiment, if one uses a 1-Mb resolution and a lower detection limit of 6.3% of tumor-derived DNA for detecting a chromosomal aberration, the number of molecules in each 1-Mb segment would need to be 60,000. This would be translated to approximately 180 million (60,000 reads/Mb×3,000 Mb) alignable reads for the whole genome.

FIG. 15 shows a table 1500 illustrating the depth required for various numbers of segments and fractional concentration of tumor-derived fragments according to embodiments of the present invention. Column 1510 provides the concentration of fragments from tumor cells for the sample. The higher the concentration, the easier to detect the aberration, so less number of molecules are required to be analyzed. Column 1520 provides the estimated number of molecules required per segment, which may be calculated via the method described in the section above on depth.

A smaller segment size would give a higher resolution for detecting smaller chromosomal aberrations. However, this would increase the requirement of the number of molecules to be analyzed in total. A larger segment size would reduce the number of molecules required for the analysis in the expense of resolution. Therefore, only larger aberrations can be detected. In one implementation, larger regions could be used, segments showing an aberration could be subdivided and these subregions analyzed to obtain better resolution (e.g., as is described above). Column 1530 provides the size of each segment. The smaller the value, the more regions are used. Column 1540 shows the number of molecules to be analyzed for the whole genome. Accordingly, if one has an estimate (or minimum concentration to detect), the number of molecules to analyze can be determined.

VI. PROGRESS OVER TIME

As a tumor progresses, the amount of tumor fragments will increase, since the tumor will release more DNA fragments (e.g., due to the growth of the tumor, more necrosis, or higher vascularity). The more DNA fragments from the tumor tissues into the plasma will increase the degree of imbalance in the plasma (e.g., the difference in the tag counts between the two haplotypes in RHDO will increase). Additionally, since the number of tumor fragments increases, the number of regions where aberration exists can more easily be detected. For example, the amount of tumor DNA for a region may be so small that the aberration cannot be detected since a statistically significant difference cannot be established because not enough fragments are analyzed when a tumor is small and is releasing a small amount of cancer DNA fragments. More fragments could be analyzed even when a tumor is small, but that may require a large sample (e.g. a lot of plasma).

The tracking of the progress of a cancer can use the amount of aberration in one or more regions (e.g., by imbalance or required depth) or the amount (number and/or size) of chromosomal regions exhibiting an aberration. In one example, if the amount of aberration of one region (or several regions) increases faster than the aberrations of other regions, then that region(s) can be used as a preferred marker to monitor the cancer. This increase could be the result of the tumor being large and thus releasing many fragments, and/or that the region is amplified many times. One can also monitor the aberration value (e.g. the amount of aberration or the number of regions showing aberrations, or a combination thereof) after surgery to confirm that the tumor has been properly removed.

In various implementations of the technology, the determination of the fractional concentration of tumoral DNA is used for the staging, prognostication, or monitoring the progress of the cancer. The measured progress can provide information as to the current stage of the cancer and how fast the cancer is growing or spreading. The "stage" of a cancer is related to all or some of the following: the size of the tumor, the histological appearance, the presence/absence of lymph node involvement, and the presence/absence of distant metastases. The "prognostication" of cancer involves estimating the chance of disease progression and/or the chance of survival from the cancer. It can also involve an estimation of the time in which the patient would be free of clinical progression, or the duration of survival. The "monitoring" of cancer would involve checking to see if the cancer has progressed (e.g. has increased in size, has increased involvement of the lymph nodes, or has spread to distant organs, i.e. metastases). Monitoring can also involve the checking if the tumor has been controlled by a treatment. For example, if treatment is effective, then one could see a reduction in the size of a tumor, the regression of the metastases or lymph node involvement, an improvement in the general well-being of the patient (e.g. increase in body weight).

A. Determination of the Fractional Concentration of Cancer DNA

One way of tracking an amount of increase in aberration for one or more regions is to determine the fractional concentration of cancer DNA for the regions(s). The change in the fractional concentration of cancer DNA can then be used to track the tumor over time. This tracking can be used to diagnose, e.g., a first measurement can provide the background level (which may correspond to a person's general level of aberration) and later measurements can see changes, which would suggest a tumor growing (thus cancer). The changes in the fractional concentration of cancer DNA can also be used to prognosticate how well a treatment is doing. In other implementations of the technology, an increase in the fractional concentration of tumoral DNA in plasma would indicate a worse prognosis or an increase in the tumor load with the patient.

The fractional concentration of cancer DNA can be determined in various ways. For example, the difference in tag counts from one haplotype compared to another (or one region compared to another). Another method is the depth (i.e. the number of fragments analyzed) before a statistically significant difference is seen. For the earlier example, the difference in the haplotype dosage can be used for determining the fractional concentration of the tumor-derived DNA in the biological sample (e.g. plasma) by analyzing the chromosomal regions with loss of heterozygozity.

It has been shown that the amount of tumor-derived DNA is positively correlated with the tumor load in cancer patients (Lo et al. Cancer Res. 1999; 59:5452-5. and Chan et al. Clin Chem. 2005; 51:2192-5). Therefore, the serial monitoring of the fractional concentration of tumor-derived DNA in the biological samples (e.g. plasma samples) by RHDO analysis can be used to monitor the disease progression of the patient. For example, the monitoring of the fractional concentration of the tumor-derived DNA in serially collected samples (e.g. plasma) after treatment can be used for determining a success of the treatment.

Figure 16:
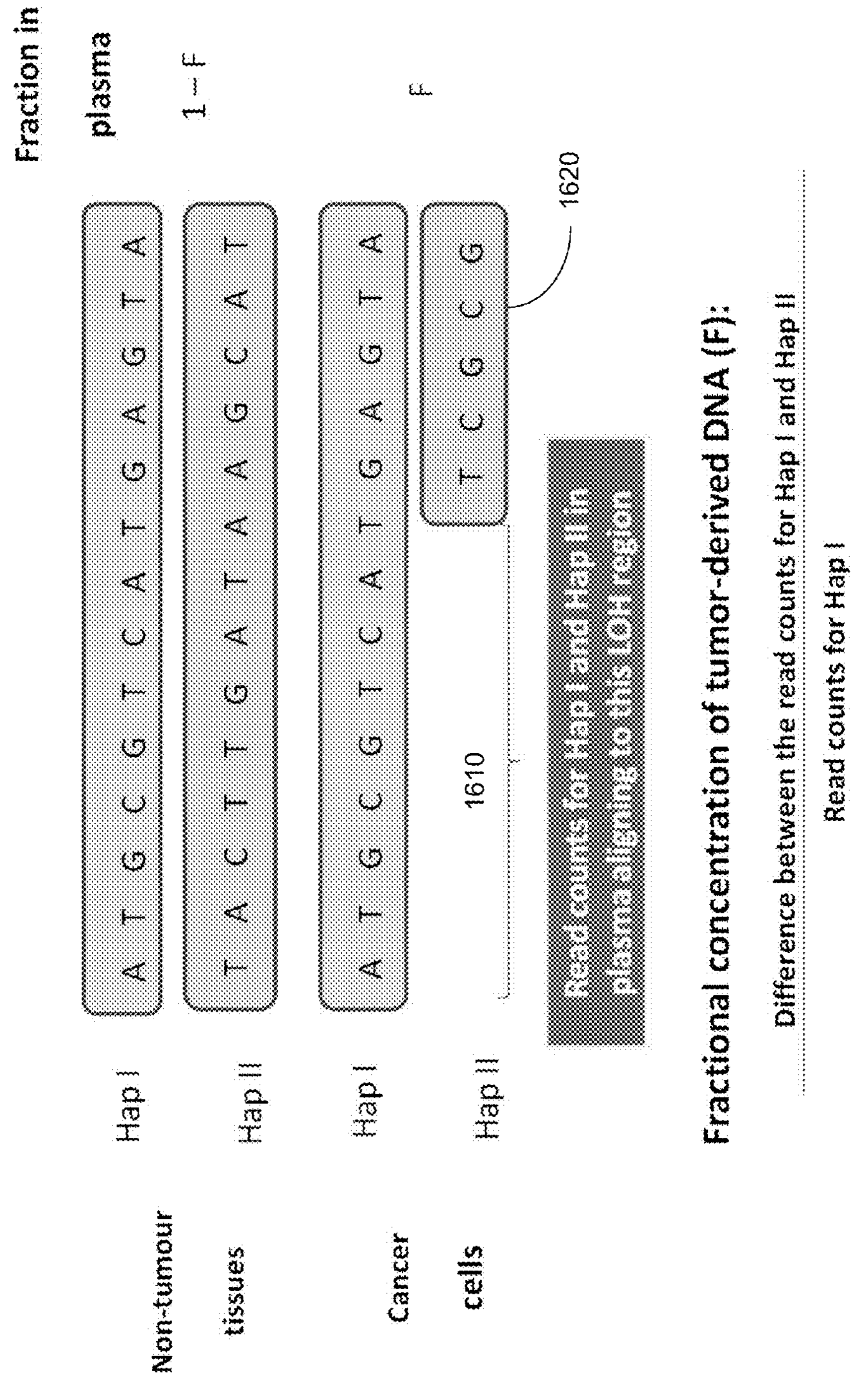
FIG. 16 shows a principle of measuring the fractional concentration of tumor-derived DNA in plasma by relative haplotype dosage (RHDO) analysis according to embodiments of the present invention. Hap I (SEQ ID NO:1) and Hap II (SEQ ID NO:2) represents the two haplotypes in the non-tumor tissues according to embodiments of the present invention.

FIG. 16 shows a principle of measuring the fractional concentration of tumor-derived DNA in plasma by RHDO analysis according to embodiments of the present invention. An imbalance is determined between two haplotypes and the degree of imbalance can be used for determining the fractional concentration of tumoral DNA in the sample.

Hap I and Hap II represents the two haplotypes in the non-tumor tissues. Hap II is partially deleted in the tumor tissues in subregion 1610. Therefore, the Hap II-associated fragments corresponding to the deleted region 1610 that are detected in plasma are contributed by the non-tumor tissues. On the other hand, region 1610 in Hap I is present in both tumor and non-tumor tissues. Therefore the difference between the read counts of Hap I and Hap II would represent the amount of tumor-derived DNA in plasma.

The fractional concentration of tumor-derived DNA (F) can be calculated from the number of sequenced reads (tags) from the deleted and non-deleted chromosomes for the chromosomal regions affected by LOH using the following formula: $F=(N_{HapI}-N_{HapII})\ N_{HapI}\times 100\%$, where $N_{HapI}$ is the number of sequenced reads corresponding to alleles on Hap I for the heterozygous SNPs located in the chromosomal regions affected by LOH; and $N_{HapII}$ is the number of sequenced reads corresponding to alleles on Hap II for the heterozygous SNPs located in the chromosomal region 1610 affected by LOH.

The above formula is equivalent to defining p as the cumulative tag counts for heterozygous loci located on the chromosome region not including a deletion (Hap I) and q as the cumulative tag counts for the chromosomal region including a deletion (Hap II) 1610, with the fractional concentration of tumoral DNA in the sample (F) calculated as $F=1-q/p$. For the example illustrated in FIG. 11, the fractional concentration of tumoral DNA is 14% (1−104/121).

The fractional concentration of tumor-derived DNA in the plasma samples of an HCC patient was collected before and after tumor resection. Before tumor resection, $N_{HapI}$ for a first haplotype of a given chromosomal region was 30,443, and for $N_{HapII}$ for a second haplotype of the chromosomal region was 16,221, which gives an F of 46.7%. After tumor resection, $N_{HapI}$ was 31,534, and for $N_{HapII}$ was 31,089, which gives an F of 1.4%. This monitoring shows that the tumor resection was successful.

The degree of the change in the circulating DNA size profile can also be used for determining the fractional concentration. In one implementation, the exact size distribution of plasma DNA derived from both tumor and non-tumor tissues can be determined, and then the measured size distribution falling between the two known distributions can provide the fractional concentration (e.g. using a linear model between the two statistical values of the size distributions of the tumor and non-tumor tissues). Alternatively, a serial monitoring of size changes can be used. In one aspect, the change in size distribution is determined as being proportional to the fractional concentration of tumoral DNA in plasma.

The difference between different regions can also be used in a similar manner, i.e., the non-specific haplotype detection methods described above. In tag counting methods, several parameters can be used for the monitoring of disease progression. For example, the magnitude of the z-score for regions exhibiting chromosomal aberrations can be used to reflect the fractional concentration of tumor-derived DNA in a biological sample (e.g. plasma). The degree of over- or under-representation of a particular region is proportional to the fractional concentration of tumor-derived DNA in the sample and the extent or number of copy number change in the tumor tissues. The magnitude of the z-score is a measurement of the degree of over- or under-representation of the particular chromosomal region in the sample compared to the control subjects. Therefore, the magnitude of the z-score can reflect the fractional concentration of tumor DNA in the sample and, hence, the tumor load of the patient.

B. Tracking Number of Regions

As mentioned above, the number of regions exhibiting chromosomal aberration can be used to screen for cancer, and it can be used to monitor and prognosticate as well. As examples, the monitoring can be used to determine a current stage of the cancer, if cancer has reappeared, and if treatment has worked. As a tumor progresses, the genomic makeup of the tumor will degrade more. To identify this continued degradation, the methods of tracking a number of region (e.g., predefined regions of 1 Mb) can be used to identify the progression of a tumor. Tumors at more advanced stages of cancer would then have more regions that exhibit an aberration.

C. Method

Figure 17:
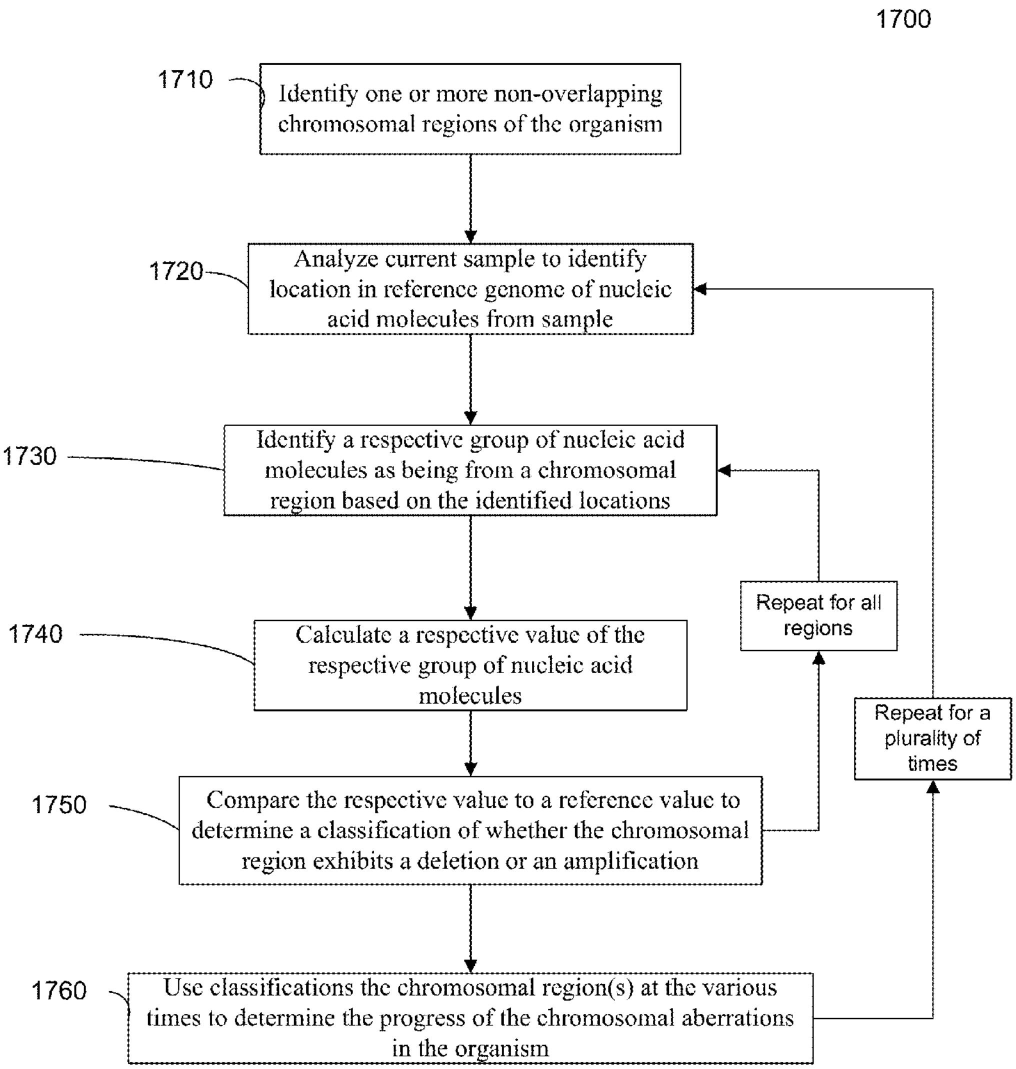
FIG. 17 is a flowchart illustrating a method of determining a progress of chromosomal aberrations in an organism using biological samples including nucleic acid molecules according to embodiments of the present invention.

FIG. 17 is a flowchart illustrating a method of determining a progress of chromosomal aberrations in an organism using biological samples including nucleic acid molecules according to embodiments of the present invention. In one embodiment, at least some of the nucleic acid molecules are cell-free. As examples, the chromosomal aberrations may be from malignant tumors or premalignant lesions. Also, an increase in aberrations could be due to the organism having more and more cells containing chromosomal aberrations over time, or due to the organism having a proportion of cells that contain an increasing amount of aberrations per cell. As an example of a decrease, treatment (e.g. surgery or chemotherapy) can cause the removal or reduction of cells associated with cancer.

In step 1710, one or more non-overlapping chromosomal regions of the organism are identified. Each chromosomal region including a plurality of loci. The regions can be identified by any suitable method, e.g., those described herein.

Steps 1720-1750 are performed for each of a plurality of times. Each time corresponds to a different time when a sample was obtained from the organism. The current sample is the sample being analyzed for a given time period. For example, a sample may be taken every month for 6 months, and the analysis can be made soon after the sample was obtained. Alternatively, the analysis can be made after several measurements are taken over a san of several time periods.

In step 1720, a current biological sample of the organism is analyzed to identify a location of the nucleic acid molecule in a reference genome of the organism. The location may be determined in any of the ways mentioned herein, e.g., by sequencing the fragments to obtain sequenced tags and aligning the sequenced tags to the reference genome. A particular haplotype of a molecule can also be determined for the haplotype-specific methods.

Steps 1730-1750 are performed for each of the one or more chromosomal regions. When a plurality of regions are used, embodiments from section V may be used. In step 1730, a respective group of nucleic acid molecules is identified as being from the chromosomal region based on the identified locations. The respective group includes at least one nucleic acid molecule located at each of the plurality of loci of the chromosomal region. In one embodiment, the group can be fragments that align to a particular haplotype of the chromosomal region, e.g., as in the RHDO method above. In another embodiment, the group can be of any fragment that aligns to the chromosomal region, as in the methods described in section IV.

In step 1740, a computer system calculates a respective value of the respective group of nucleic acid molecules. The respective value defines a property of the nucleic acid molecules of the respective group. The respective value can be any of the values mentioned herein. For example, the value can be the number of fragments in the group or a statistical value of a size distribution of the fragments in the group. The respective value can also be a normalized value, e.g., a tag count of the region divided the total number of tag counts for the sample or the number of tag counts for a reference region. The respective value can also be a difference or ratio from another value (e.g., in RHDO), thereby providing the property of a difference for the region.

In step 1750, the respective value is compared to a reference value to determine a classification of whether the first chromosomal region exhibits a deletion or an amplification. This reference value can be any threshold or reference value described herein. For example, the reference value could be a threshold value determined for normal samples. For RHDO, the respective value could be the difference or ratio of tag counts for the two haplotypes, and the reference value can be a threshold for determining that a statistically significant deviation exists. As another example, the reference value could be the tag count or size value for another haplotype or region, and the comparison can include taking a difference or ratio (or function of such) and then determining if the difference or ratio is greater than a threshold value. The reference value can be determined according to any suitable method and criteria, e.g., as described herein.

In step 1760, the classifications of each of the chromosomal regions at the plurality of times are used to determine the progress of the chromosomal aberrations in the organism. The progress can be used to determine whether the organism has cancer, a stage of the cancer, and a prognosis of the cancer. Each of these determination can involve a cancer classification, as is described herein.

This cancer classification can be performed in various ways. For example, an amount of aberrant regions can be counted and compared to a threshold. The classification for the regions can be a numerical value (e.g., a tumor concentration, with the respective and reference values being values for difference haplotypes or different regions) and the change in the concentration can be determined. The change in concentration can be compared to a threshold to determine that a significant increase has occurred, thereby signaling the existence of a tumor.

VII. EXAMPLES

A. RHDO Using SPRT

In this section, we show an example of using relative haplotype dosage (RHDO) analysis using SPRT for a hepatocellular carcinoma (HCC) patient. In the tumor tissue of this patient, deletion of one of the two chromosome 4 was observed. This results in a loss of heterozygozity for the SNPs on chromosome 4. For the haplotyping of this patient, the genomic DNA for the patient, his wife and his son was analyzed and the genotypes of the three individuals were determined. The constitutional haplotypes of the patient was then derived from their genotypes. Massively parallel sequencing was performed and the sequenced reads with SNP alleles corresponding to the two haplotypes of chromosome 4 were identified and counted.

The equations and principles of RHDO and SPRT has been described above. In one embodiment, the RHDO analysis would be programmed to detect, for example 10% of difference in the haplotype dosages in the DNA sample which is corresponding to the presence of 10% of tumor-derived DNA when one of the two haplotypes is amplified or deleted. In other embodiments, the sensitivity of RHDO analysis can be set to detect 2%, 5%, 15%, 20%, 25%, 30%, 40% and 50%, etc, of tumor-derived DNA in the DNA sample. The sensitivity of the RHDO analysis can be adjusted in the parameter for the calculation of the upper and lower threshold of the SPRT classification curves. The adjustable parameters can be the desired level of detection limit (e.g. what percentage of tumor concentration should be detectable, which affects the number of molecule analyzed) and the threshold for the classification, e.g., using an odds ratio (ratio of tag counts for one haplotype relative to the tag counts for other haplotype).

Figure 18A:
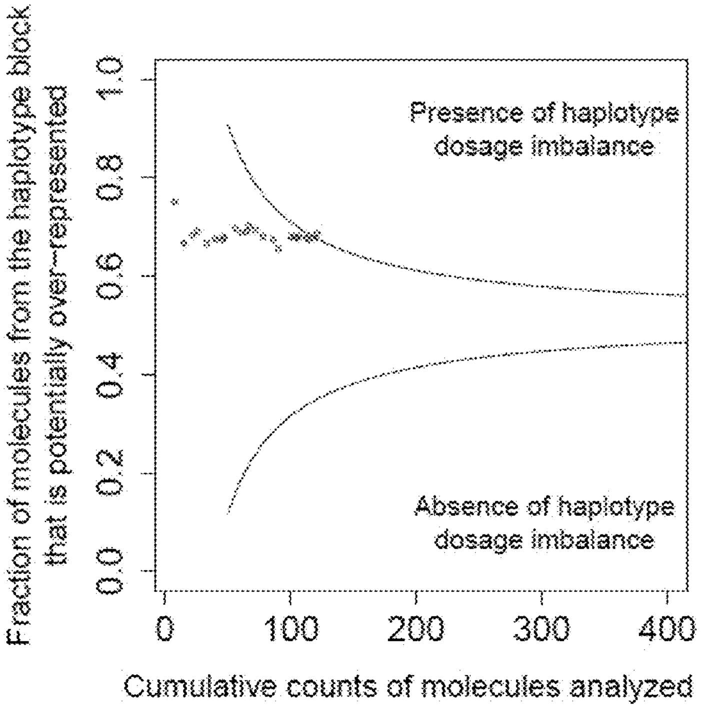
FIG. 18A shows an SPRT curve for RHDO analysis for a segment on the q arm of chromosome 4 for a patient with cancer. The dots represent the ratio the cumulative counts after respective heterozygous loci.

In this RHDO analysis, the null hypothesis is that the two haplotypes for chromosome 4 are present in the same dosage. The alternative hypothesis is that the dosages of the two haplotypes differ by more than 10% in the biological sample (e.g. plasma). The numbers of sequenced reads with SNP alleles corresponding to the two haplotypes were compared statistically against the two hypotheses as the data from different SNPs accumulate. A SPRT classification is made when the accumulated data are sufficient to determine if the two haplotype dosages are present in equal amount or differ by at least 10% statistically. A typical SPRT classification block on the q arm of chromosome 4 is shown in FIG. 18A. The threshold of 10% is used here for illustration purpose only. Other degrees of difference (e.g 0.1%, 1%, 2%, 5%, 15% or 20%) can also be detected. In general, the lower the degree of difference that one would like to detect, the more DNA molecules one would need to analyze. Conversely, the larger the degree of difference that one would like to detect, the smaller the number of DNA molecules that one would need to analyze and yet to achieve a statistically significant result. For this analysis, an odds ratio is used for SPRT, but other parameters such as a z-score or a p-value may be used.

Figure 18B:
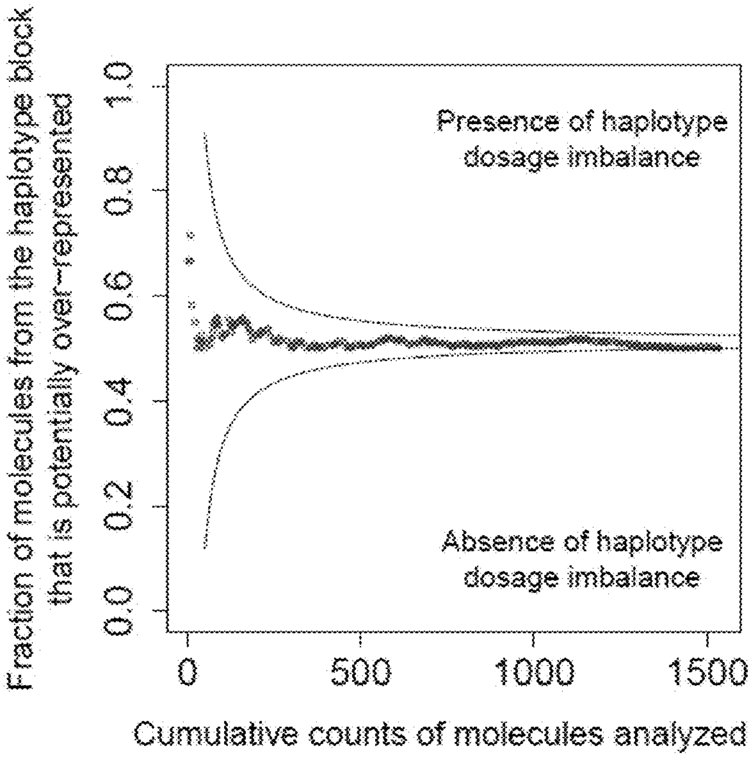
FIG. 18B shows an SPRT curve for RHDO analysis for a segment on the q arm of chromosome 4 for the patient after treatment.

In this plasma sample of the HCC patient taken at the time of diagnosis, there were 76 and 148 successful RHDO classifications for the p and q arms of chromosome 4, respectively. All the RHDO classifications indicate that there was haplotype dosage imbalance in the plasma sample taken at the time of diagnosis. As a comparison, the plasma sample of the patient taken after surgical resection of the tumor was also analyzed, as shown in FIG. 18B. For the post-treatment samples, there were 4 and 9 successful RHDO classifications for the p and q arms of chromosome 4, respectively. All the four RHDO classifications indicate that there was no observable haplotype dosage imbalance of >10% in the plasma sample. Among the 9 RHDO classifications for chromosome 4q, 7 indicate the absence of haplotype dosage imbalance and 2 indicate that imbalance is present. The number of RHDO blocks showing dosage imbalance of >10% has significantly reduced after the tumor resection indicating that the size of the chromosomal region showing dosage imbalance of >10% is significantly smaller in the post-treatment sample than in the pre-treatment sample. These results suggest that the fractional concentration of tumor DNA in the plasma has reduced after the surgical resection of the tumor.

When compared with the non-haplotype specific methods, RHDO analysis could provide a more precise estimation of the fractional concentration of the tumoral DNA and is particularly useful for the monitoring of disease progression. Thus, one would expect that cases with a disease progression would exhibit an increase in the fractional concentration of tumoral DNA in plasma; while cases with stable disease or those in which the tumor has regressed or reduced in size would have a reduction in the fractional concentration of tumoral DNA in plasma.

B. Targeted Analysis

In selected embodiments, the universal sequencing of DNA fragments can be performed following a target enrichment approach. Such an approach is herein also referred to as enriched target sequencing. One embodiment of such an approach is the prior selection of fragments using an in-solution capture system (e.g. the Agilent SureSelect system, the Illumina TruSeq Custom Enrichment Kit (illumina.com/applications/sequencing/targeted_resequencing.ilmn), or by the MyGenostics GenCap Custom Enrichment system (mygenostics.com/)) or a microarray-based capture system (e.g. the Roche NimbleGene system). Although some other regions can be captured, certain regions are preferentially captured. Such methods can allow such regions to be analyzed at more depth (e.g., more fragments can be sequenced or analyzed with digital PCR), and/or at lower cost. The greater depth can increase the sensitivity in the region. Other enrichment methods can be performed based on size of fragments and methylation patterns.

Accordingly, an alternative to analyzing the DNA sample in a genomewide fashion is to target the regions of interest for detecting the common chromosomal aberrations. The targeted approach can potentially improve the cost-effectiveness of this approach because the analytical process would mainly focus on the regions that chromosomal aberrations are potentially present or regions with changes that would be particularly characteristic for a particular tumor type, or those with changes that would be particularly clinically important. Examples of the latter include changes that would occur early on in the oncogenesis of a particular cancer type (e.g. the presence of amplifications of 1q and 8q, and deletion of 8q are early chromosomal changes in HCC—van Malenstein et al. Eur J Cancer 2011; 47:1789-97); or changes that are associated with good or bad prognosis (e.g, gains at 6q and 17q, and loss at 6p and 9p are observed during tumor progression, and the presence of LOH at 18q, 8p and 17p are associated with poorer survival in colorectal cancer patients—Westra et al. Clin Colorectal Cancer 2004; 4:252-9); or which are predictive of treatment response (e.g. the presence of gains at the 7p is predictive of the response to tyrosin kinase inhibitors in patients with epidermal growth factor receptor mutations—Yuan et al. J ClinOncol 2011; 29:3435-42). Other examples of genomic regions altered in cancer can be found in a number of online database (e.g. the Cancer Genome Anatomy Project database (cgap.nci.nih.gov/Chromosomes/RecurrentAberrataions) and the Atlas of Genetics and Cytogenetics in Oncology and Haematology (atlasgeneticsoncology.org//Tumors/Tumorliste.html). In contrast, in non-targeted genomewide approach, regions that chromosomal aberrations are unlikely to occur would be analyzed to the same degree as regions with potential aberrations.

We have applied the target-enrichment strategy to analyze the plasma samples from 3 HCC patients and 4 healthy control subjects. The target enrichment was performed using the SureSelect capture system from Agilent (Gnirke et al. Nat. Biotechnol 2009.27:182-9). The SureSelect system was chosen as an example of a possible target enrichment technology. Other solution phase (the IlluminaTruSeq Custom Enrichment system) or solid phase (e.g. the Roche-Nimblegen system) target capture systems and amplicon-based target enrichment systems (e.g. QuantaLifesystem and RainDance system) can also be used. The capturing probes are designed to be located on chromosomal regions that commonly and uncommonly show aberrations in HCC. After target capturing, each DNA sample was then sequenced by one lane of a flow cell on an IlluminaGAIIx analyzer. The regions that amplification and deletion uncommonly occur are used as reference to compare with the regions in which amplifications and deletions are more commonly present.

Figure 19:
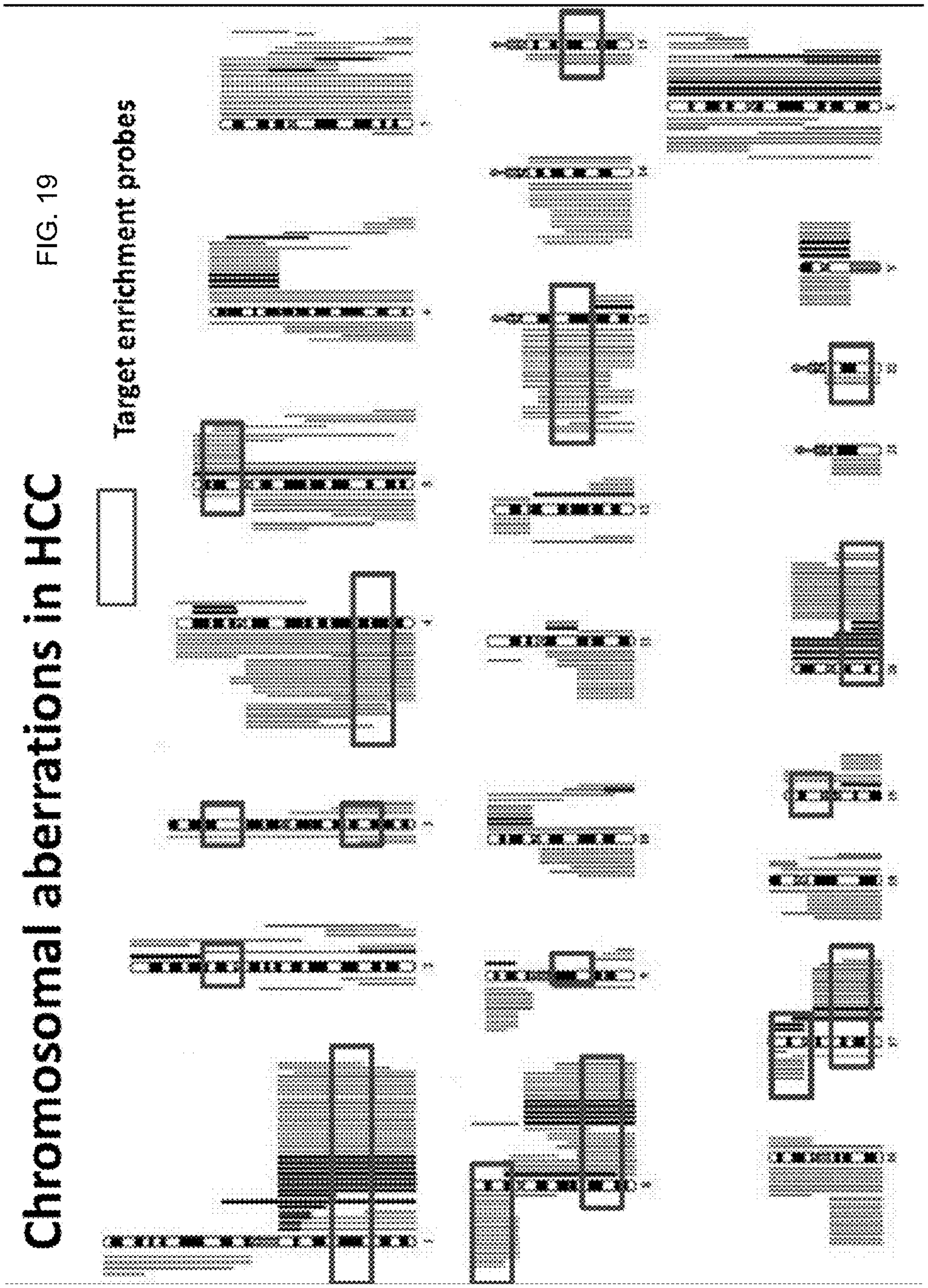
FIG. 19 shows common chromosomal aberrations found in HCC.

In FIG. 19, common chromosomal aberrations found in HCC are shown (figure is adapted from Wong et al (Am J Pathol 1999; 154:37-43). The lines on the right side of the chromosome ideogram represent chromosomal gains and lines on the left side represent chromosomal loss of individual patient samples. Thick lines represent high-level gains. The rectangles represent the locations of the target capturing probes.

Targeted Tag Counting Analysis

For the detection of chromosomal aberrations, we first calculated the normalized tag counts for regions with potential aberrations and the reference regions. The normalized tag count was then corrected for GC content of the region as previously described by Chen et al (PLoS One 2011; 6:e21791). In the current example, the p-arm of chromosome 8 was chosen as the region of potential aberration and the q-arm of chromosome 9 was chosen as the reference region. The tumor tissues of the three HCC patients were analyzed using the AffymetrixSNP 6.0 array for chromosomal aberrations. The changes in chromosome dosage for 8p and 9q in the tumor tissues are shown below for the 3 patients. Patient HCC 013 had a loss for 8p and no change for 9q. Patient HCC 027 had a gain for 8p and no change for 9q. Patient HCC 023 had a loss for 8p and no change for 9q.

Figure 20A:
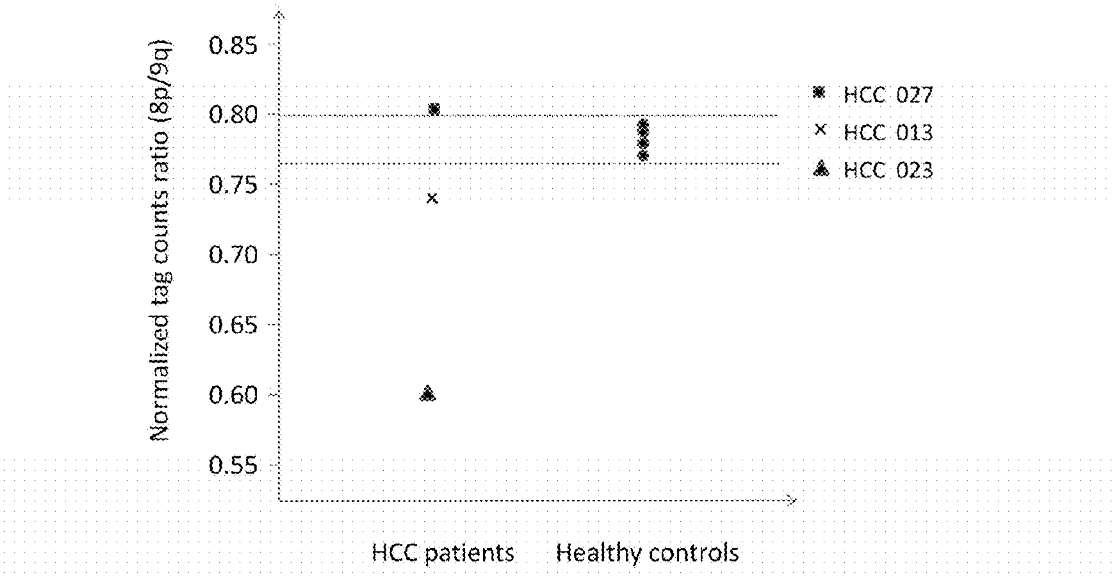
FIG. 20A shows the results normalized tag counts ratio for the HCC and healthy patients using targeted analysis.

The ratio of the normalized tag count between chr 8p and 9q was then calculated for the three HCC patients and four healthy control subjects using a targeted analysis. FIG. 20A shows the results normalized tag counts ratio for the HCC and healthy patients. For cases HCC 013 and HCC023, a reduced normalized tag count ratio between 8p and 9q was observed. This is consistent with the finding of the loss of chromosome 8p in the tumor tissues. For case HCC 027, an increased ratio is observed and is consistent with the gain in chromosome 8p in the tumor tissues of this case. The dotted lines represent the region with two standard deviations of mean value of the four normal cases.

Targeted Size Analysis

In previous sections, we describe the principle of detecting cancer-associated alterations by determining the size profile of plasma DNA fragments in cancer patients. Size alterations can also be detected with the target-enrichment approach. For the three HCC cases (HCC 013, HCC 027 and HCC023), the size of each sequenced DNA fragment was determined after aligning the sequenced reads to the reference human genome. The size of the sequenced DNA fragments was deduced from the coordinates of the outermost nucleotides of both ends. In other embodiments, the whole DNA fragment will be sequenced and the fragment size can then be determined directly from the sequenced length. The size distribution of DNA fragments aligning to chromosome 8p was compared to the size distribution of DNA fragments aligning to chromosome 9q. For the detection of the difference in the size distributions of the two populations of DNA, the proportion of DNA fragments shorter than 150 bp was first determined for each of the population in the current example. In other embodiments, other size cutoff values, e.g. 80 bp, 110 bp, 100 bp, 110 bp, 120 bp, 130 bp, 140 bp, 160 bp and 170 bp can be used. Then the ΔQ values were determined as the difference of the two proportions. $\Delta Q=Q_{8p}-Q_{9q}$, where $Q_{8p}$ is the proportion of DNA fragments aligning to chromosome 8p that are shorter than 150 bp; and $Q_{9q}$ is the proportion of DNA fragments aligning to chromosome 9q that are shorter than 150 bp.

As a shorter size distribution of DNA fragments would give a higher value of proportion of DNA shorter than the cutoff value (i.e. 150 bp in the current example), a higher (more positive) value of ΔF would represent a shorter distribution of the DNA fragments aligning to chromosome 8p relative to those aligning to chromosome 9q. On the contrary, a smaller (or more negative) result would indicate a longer size distribution of the DNA fragment aligning to chromosome 8p relative to those aligning to chromosome 9q.

Figure 20B:
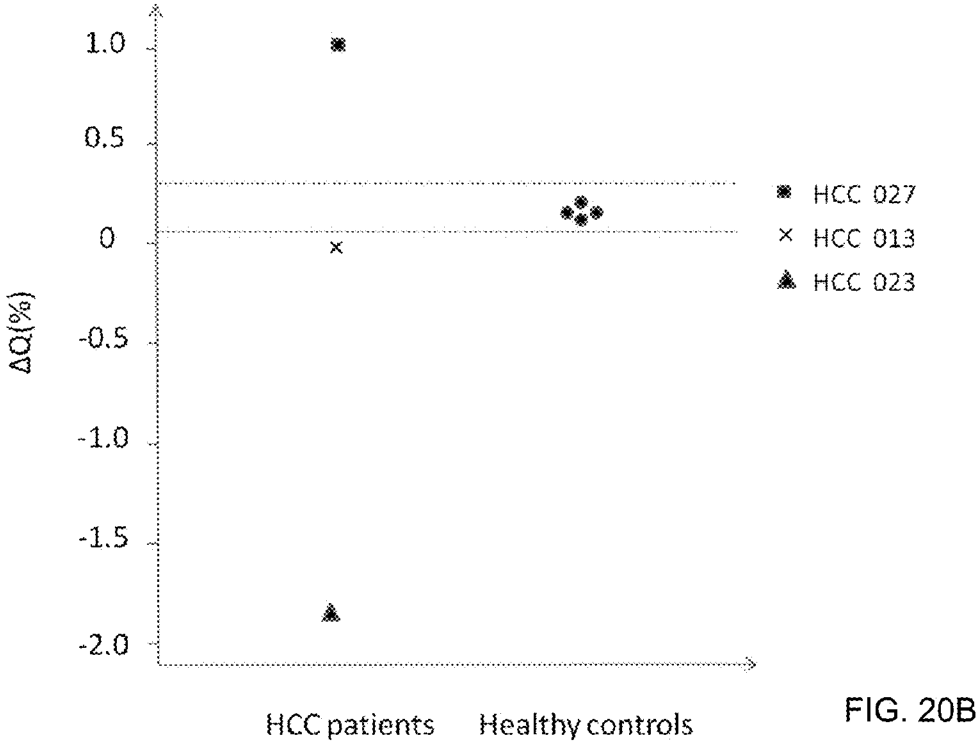
FIG. 20B shows the results of a size analysis after target enrichment and massively parallel sequencing for the 3 HCC patients and 4 healthy control subjects.

FIG. 20B shows the results of a size analysis after target enrichment and massively parallel sequencing for the 3 HCC patients and 4 healthy control subjects. Positive values of ΔQ in the four healthy control subjects indicate a slightly shorter size distribution of DNA fragments aligning to the chromosome 8p compared with those aligning to chromosome 9q. The dotted lines represent the interval of ΔQ within two standard deviations from the mean for the four control subjects. The ΔQ values of cases HCC 013 and HCC 023 were more than two standard deviations below the mean value of the control subjects. These two cases had deletion of chromosome 8p in the tumor tissues. The deletion of 8p in the tumor would result in reduced contribution of tumor-derived DNA to the plasma for this chromosomal region. As the tumor derived DNA in the circulation are shorter than the DNA derived from non-tumor tissues, this would lead to an apparently longer size distribution for plasma DNA fragments aligning to chromosome 8p. This is consistent with a lower (more negative) value of ΔQ in these two cases. In contrast, the amplification of 8p in case HCC 027 would lead to an apparently shorter distribution for DNA fragments aligning to this region. Thus, a higher proportion of plasma DNA fragments aligning to 8p would be considered short. This is consistent with the observation that the ΔQ value of HCC 027 is more positive than the healthy control subjects.

C. Multiple Regions for Detection of Tumor-Derived Chromosomal Aberrations

Chromosomal aberrations, including deletion and amplification of certain chromosomal regions, are commonly detected in tumor tissues. Characteristic patterns of chromosomal aberrations are observed in different types of cancers. Here, we use several examples to illustrate the different approaches for detecting these cancer-associated chromosomal aberrations in the plasma of cancer patients. Our approach is also useful for the screening of cancer and the monitoring of disease progression and response to treatment. Samples from one HCC patient and two nasopharyngeal (NPC) patients were analyzed. For the HCC patient, venous blood samples were collected before and after surgical resection of the tumor. For the two NPC patients, venous blood samples were collected at the time of diagnosis. Additionally, the plasma samples of one chronic hepatitis B carrier and one subject with detectable Epstein-Barr virus DNA in the plasma were analyzed. These two subjects did not have any cancer.

A detection of tumor-derived chromosomal aberrations was performed with microarray analysis. Specifically, the DNA extracted from the blood cells and the tumor sample of the HCC patient were analyzed using the Affymetrix SNP6.0 microarray system. The genotypes of the blood cells and the tumor tissues were determined using the Affymetrix Genotyping Console v4.0. Chromosomal aberrations, including gains and deletions, were determined using the Birdseed v2 algorithm based on the intensities of the different alleles of the SNPs and the copy number variation (CNV) probes on the microarray.

Count-Based Analysis

To perform sequenced tag counting analysis in plasma, ten milliliters of venous blood were collected from each of the subjects. For each blood sample, plasma was isolated after centrifugation of the sample. DNA was extracted from 4-6 mL of plasma using the QIAmp blood mini Kit (Qiagen). Plasma DNA library was constructed as previously described (Lo Y M D. Sci Transl Med 2010, 2:61ra91), and then subjected to massively parallel sequencing using the Illumina Genome Analyzer platform. Paired-end sequencing of the plasma DNA molecules was performed. Each molecule was sequenced at each of the two ends for 50 bp, thus totaling 100 bp per molecule. The two ends of each sequence were aligned to the non-repeat-masked human genome (Hg18 NCBI.36 downloaded from UCSC genome.ucsc.edu) using the SOAP2 program (soap.genomics.org.cn/) (Li R et al. Bioinformatics 2009, 25:1966-7).

The genome was then divided into multiple 1-megabase (1-Mb) segments and the number of sequenced reads aligning to each 1-Mb segment was determined. The tag count of each bin was then corrected with an algorithm based on locally weighted scatterplot smoothing (LOESS) regression according to the GC content of each bin (Chen E et al. PLoS One 2011, 6:e21791). This correction aims to minimize the quantitative bias related to sequencing which arises because of the difference in GC content between different genomic segments. The above-mentioned division into 1-Mb segments is used for illustration purpose. Other segment sizes, e.g. 2 Mb, 10 Mb, 25 Mb, or 50 Mb, etc, can also be used. It is also possible to select the segment size based on the genomic characteristics of a particular tumor in a particular patient and a particular type of tumor in general. Furthermore, if the sequencing process can be shown to have a low GC bias, for example, for single molecule sequencing techniques, such as the Helicos system (www.helicosbio.com) or the Pacific Biosciences Single Molecular Real-Time system (www.pacificbiosciences.com), the GC correction step can be omitted.

In a previous study, we have sequenced 57 plasma samples from subjects without cancer. These plasma sequencing results were used for determining the reference range of tag counts for each 1-Mb segment. For each 1-Mb segment, the mean and standard deviation of tag counts of the 57 individuals were determined. Then, the results of the study subjects were expressed as a z-score as calculated using the following equation: z-score=(no. of sequenced tag of the case−mean)/S.D, where “mean” is the mean number of sequenced tags aligning to the particular 1-Mb segment for the reference samples; and S.D. is the standard deviation of the number of sequenced tags aligning to the particular 1-Mb segment for the reference samples.

Figure 21:
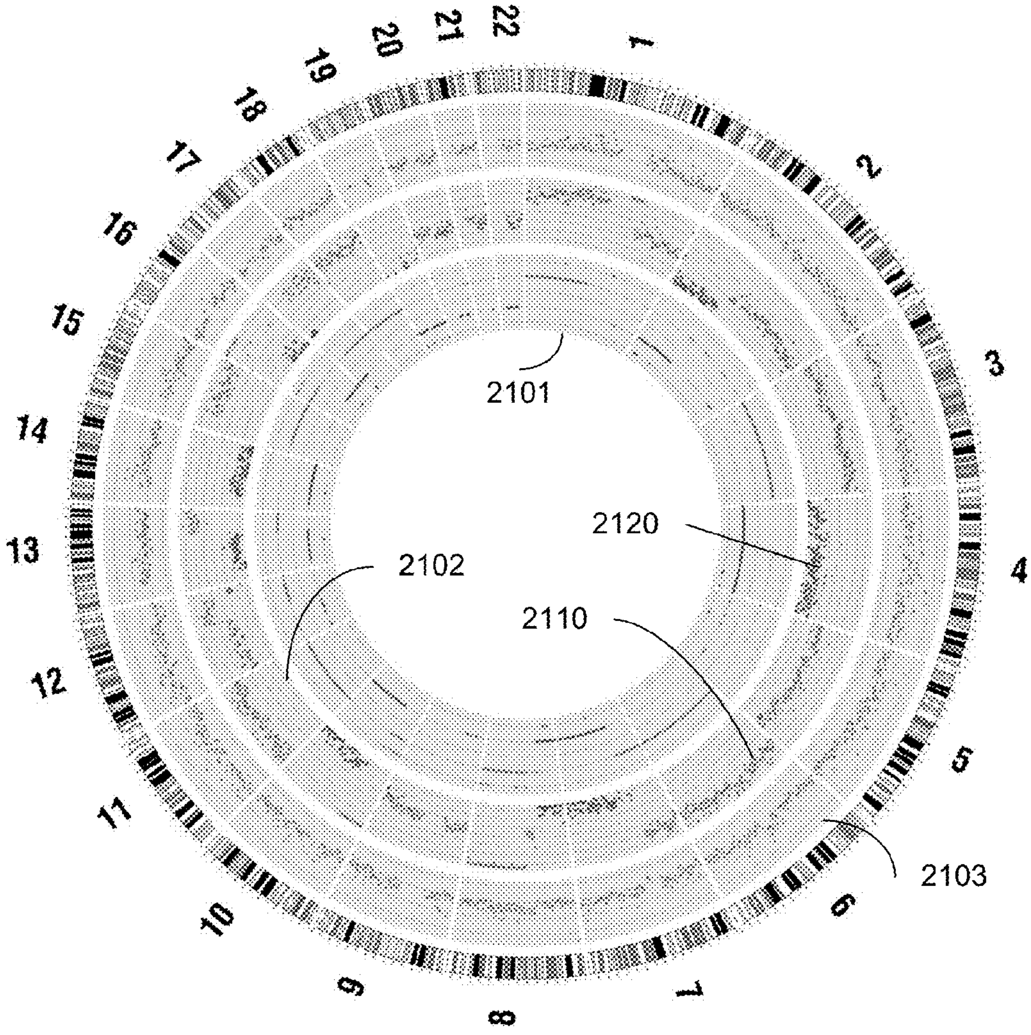
FIG. 21 shows Circos plots of a HCC patient depicting data from sequenced tag counting of plasma DNA according to embodiments of the present invention.

FIGS. 21-24 show the results of the sequenced tag counting analysis of the four study subjects. The 1-MB segments are shown at the edge of the plots. Human chromosome numbers and ideograms (outermost ring) are oriented pter-qter in a clockwise direction (centromeres are shown in yellow). In FIG. 21, the inner ring 2101 shows regions of aberration (deletion or amplification) as determined from analyzing the tumor. Inner ring 2101 is shown with five scales. The scale is from −2 (most inner line) to +2 (most outer line). The value of −2 represents the loss of both chromosome copies for the corresponding region. The value of −1 represents the loss of one of the two chromosome copy. The value of 0 represents no chromosome gain or loss. The value of +1 represents the gain of one chromosome copy and +2 represents the gain of two chromosome copies.

The middle ring 2102 shows results from the analysis of plasma. As one can see, the results mirror the inner ring. Middle ring 2102 is more lines of scale, but the progression is the same. The outer ring 2103 shows data points from analyzing plasma after treatment, and these data points are grey (confirming no over/under representation—no aberration).

Chromosomal regions with over-representation of sequenced tags in plasma (z-score of >3) are represented by green dots 2110. Regions with under-representation of sequenced tags in plasma (z-score of <−3) are represented by red dots 2120. Regions with no significant chromosomal aberration detected in plasma (z-score between −3 and 3) are represented by grey dots. The over/under representation is normalized by the total number of counts. With amplification before sequencing, the normalization may take into account GC bias.

FIG. 21 shows Circos plots of an HCC patient depicting data from sequenced tag counting of plasma DNA according to embodiments of the present invention. Tracks from inside to outside: chromosomal aberrations of the tumor tissue detected by microarray analysis (red and green color represent deletion and amplification, respectively); z-score analysis for a plasma sample obtained before surgical resection of tumor, and at 1 month after the resection. Before tumor resection, the chromosomal aberrations detected in the plasma correlate well with those identified in the tumor tissue by the microarray analysis. After tumor resection, most cancer-associated chromosomal aberrations disappeared in the plasma. These data reflect the value of such an approach for monitoring the disease progress and therapeutic efficacy.

Figure 22:
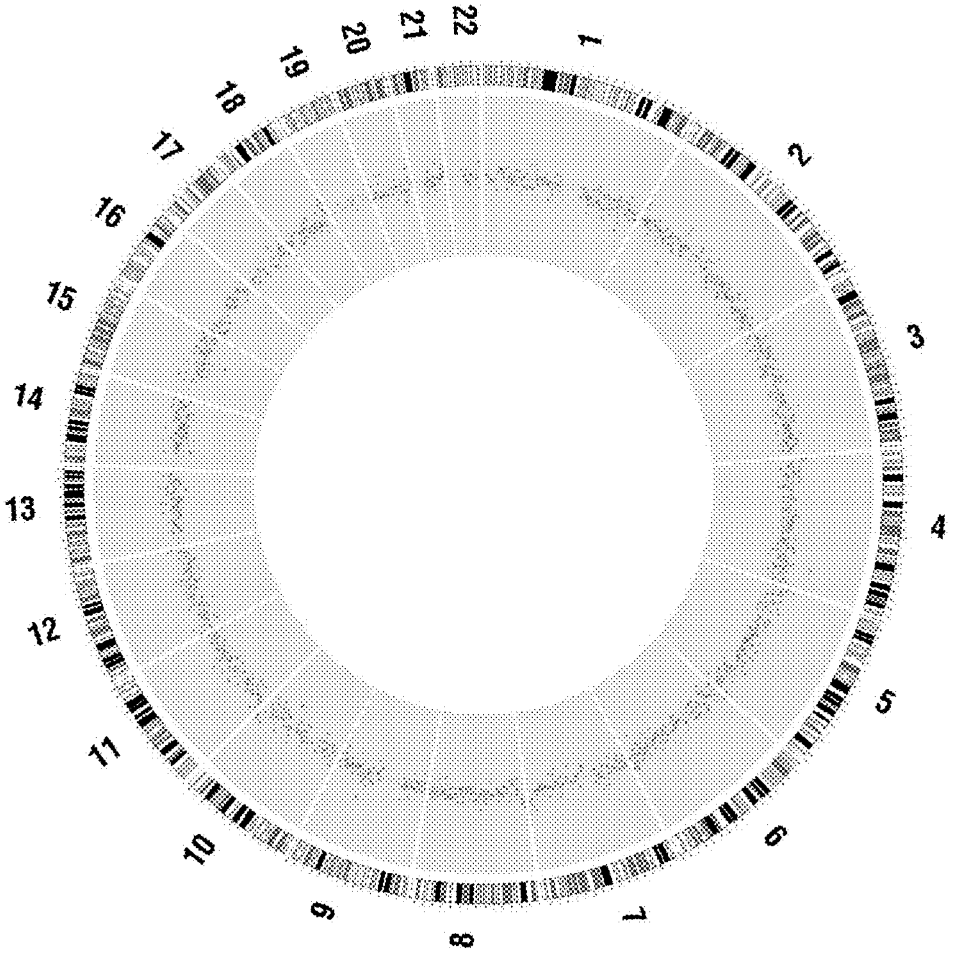
FIG. 22 shows a sequenced tag counting analysis for the plasma sample of a chronic hepatitis B virus (HBV) carrier without HCC according to embodiments of the present invention.

FIG. 22 shows a sequenced tag counting analysis for the plasma sample of a chronic HBV carrier without HCC according to embodiments of the present invention. In contrast to the HCC patient (FIG. 21), cancer-associated chromosomal aberrations were not detected in the plasma of this patient. These data reflect the value of the approach for cancer screening, diagnosis, and monitoring.

Figure 23:
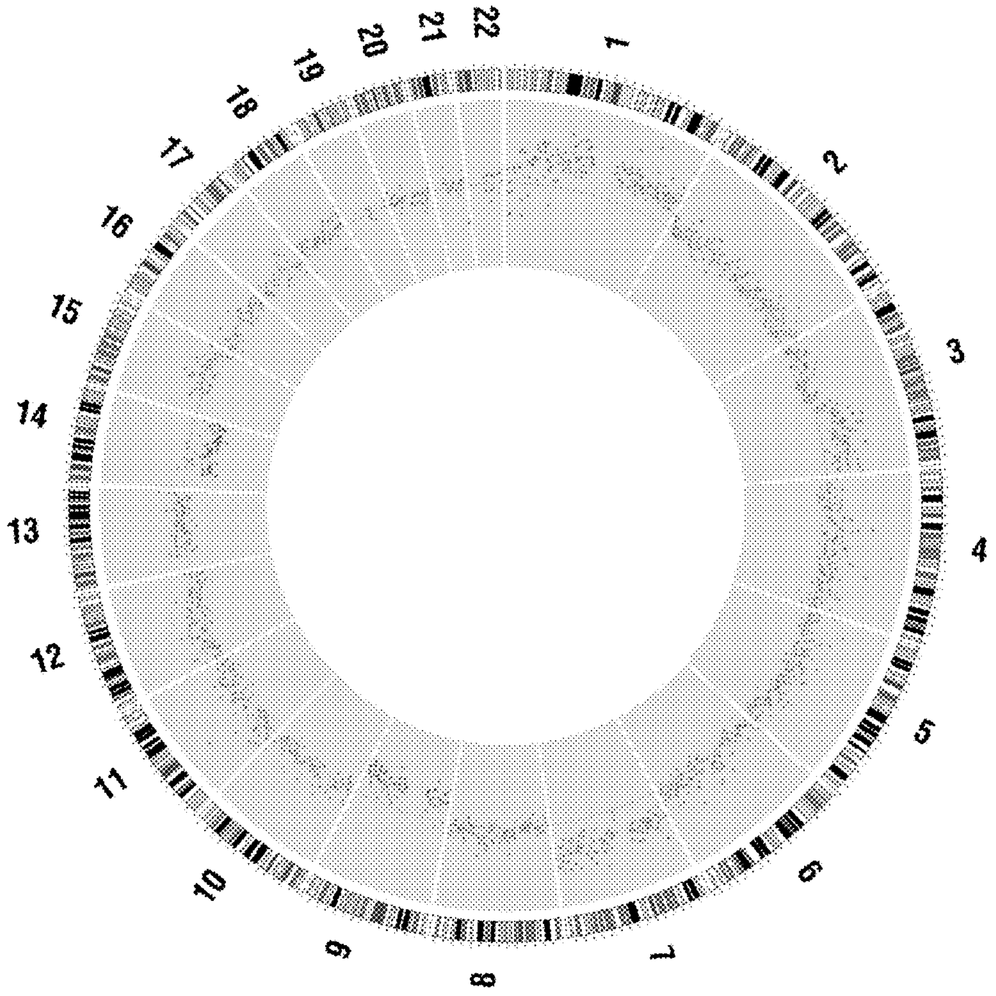
FIG. 23 shows a sequenced tag counting analysis for the plasma sample of a patient with stage 3 nasopharyngeal carcinoma (NPC) according to embodiments of the present invention.

FIG. 23 shows a sequenced tag counting analysis for the plasma sample of a patient with stage 3 NPC according to embodiments of the present invention. Chromosomal aberrations were detected in the plasma sample taken before treatment. Specifically, significant aberrations were identified in chromosomes 1, 3, 7, 9, and 14.

Figure 24:
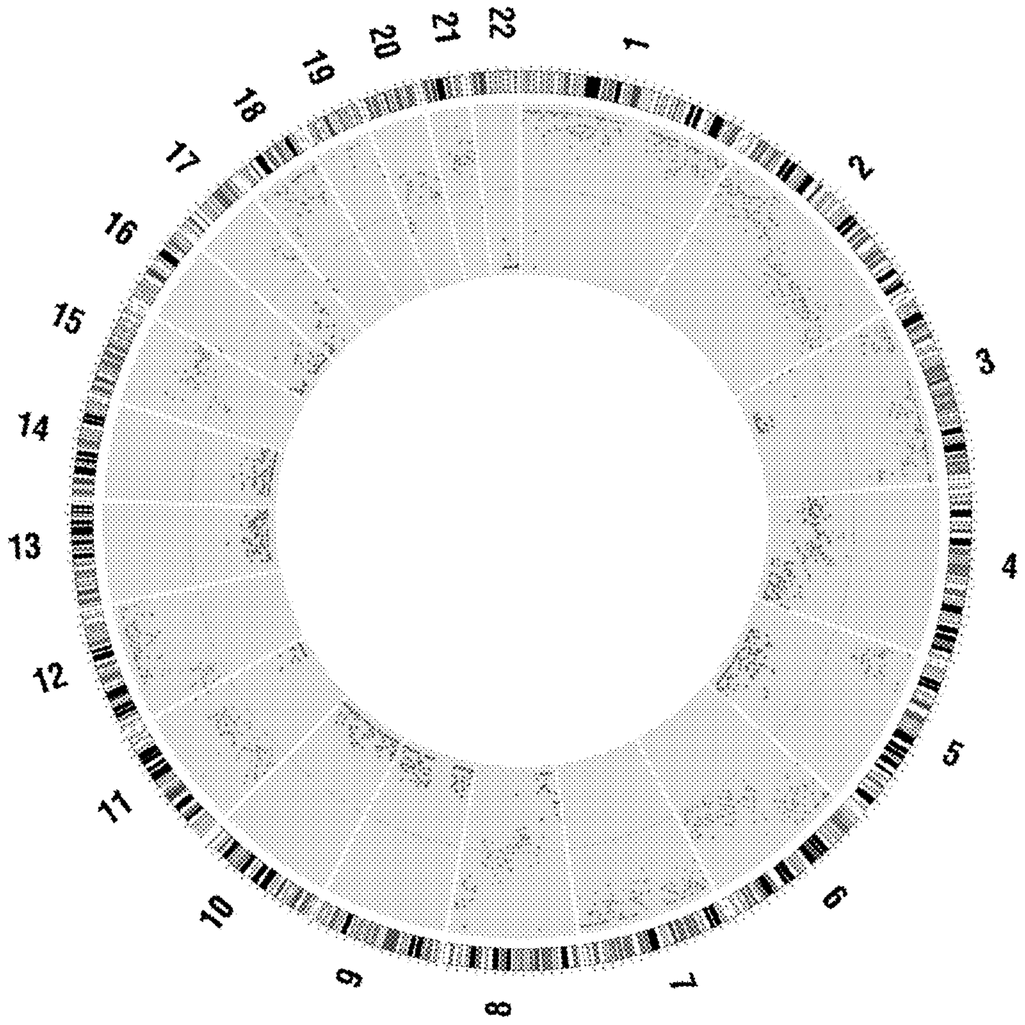
FIG. 24 shows a sequenced tag counting analysis for the plasma sample of a patient with stage 4 NPC according to embodiments of the present invention.

FIG. 24 shows a sequenced tag counting analysis for the plasma sample of a patient with stage 4 NPC according to embodiments of the present invention. Chromosomal aberrations were detected in the plasma sample taken before treatment. When compared with the patient with Stage 3 disease (FIG. 23), more chromosomal aberrations were detected. The sequenced tag counts also deviated more from the mean of the controls, i.e. the z-score deviates more from zero (either positively or negatively). The increased number of chromosomal aberrations and higher degree of deviation of the sequenced tag counts compared with controls are reflecting the more profound degree of genomic alterations in the more advanced stage of disease and hence reflect the value of such an approach for staging, prognostication and monitoring of the cancer.

Size-Based Analysis

In previous studies, it has been shown that the size distribution of DNA derived from tumor tissues is shorter than the size distribution of those derived from non-tumor tissues (Diehl F et al. Proc Natl Acad Sci USA 2005, 102(45):16368-73). In the previous sections, we have outlined the approach for detecting the plasma haplotype imbalance by size analysis of plasma DNA. Here, we used the sequencing data of the HCC patient to further illustrate this approach.

For illustration purpose, we identified two regions for size analysis. In one region (chromosome 1 (chr1); coordinates: 159,935,347 to 167,219,158), duplication of one of the two homologous chromosomes was detected in the tumor tissue. In the other region (chromosome 10 (chr10); coordinates: 100,137,050 to 101,907,356), deletion of one of the two homologous chromosome (i.e. LOH) was detected in the tumor tissue. In addition to determining which haplotype a sequenced fragment came from, the size of the sequenced fragment was also determined bioinformatically using the coordinates of the outermost nucleotides of the sequenced fragment in the reference genome. Then, the size distributions of fragments from each of the two haplotypes were determined.

For the LOH region of Chr10, one haplotype was deleted in the tumor tissue (the deleted haplotype). Therefore, all plasma DNA fragments aligning to this deleted haplotype were derived from the non-cancer tissues. On the other hand, the fragments aligning to the haplotype that was not deleted in the tumor tissues (the non-deleted haplotype) can be derived from the tumor or the non-tumor tissues. As the size distribution of the tumor-derived DNA is shorter, we would expect a shorter size distribution for fragments from the non-deleted haplotype when compared with those from the deleted haplotype. The difference in the two size distributions can be determined by plotting the cumulative frequencies of fragments against the size of DNA fragments. The population of DNA with the shorter size distribution would have more abundant short DNA and hence a more rapid increase in the cumulative frequency at the short end of the size spectrum.

Figure 25:
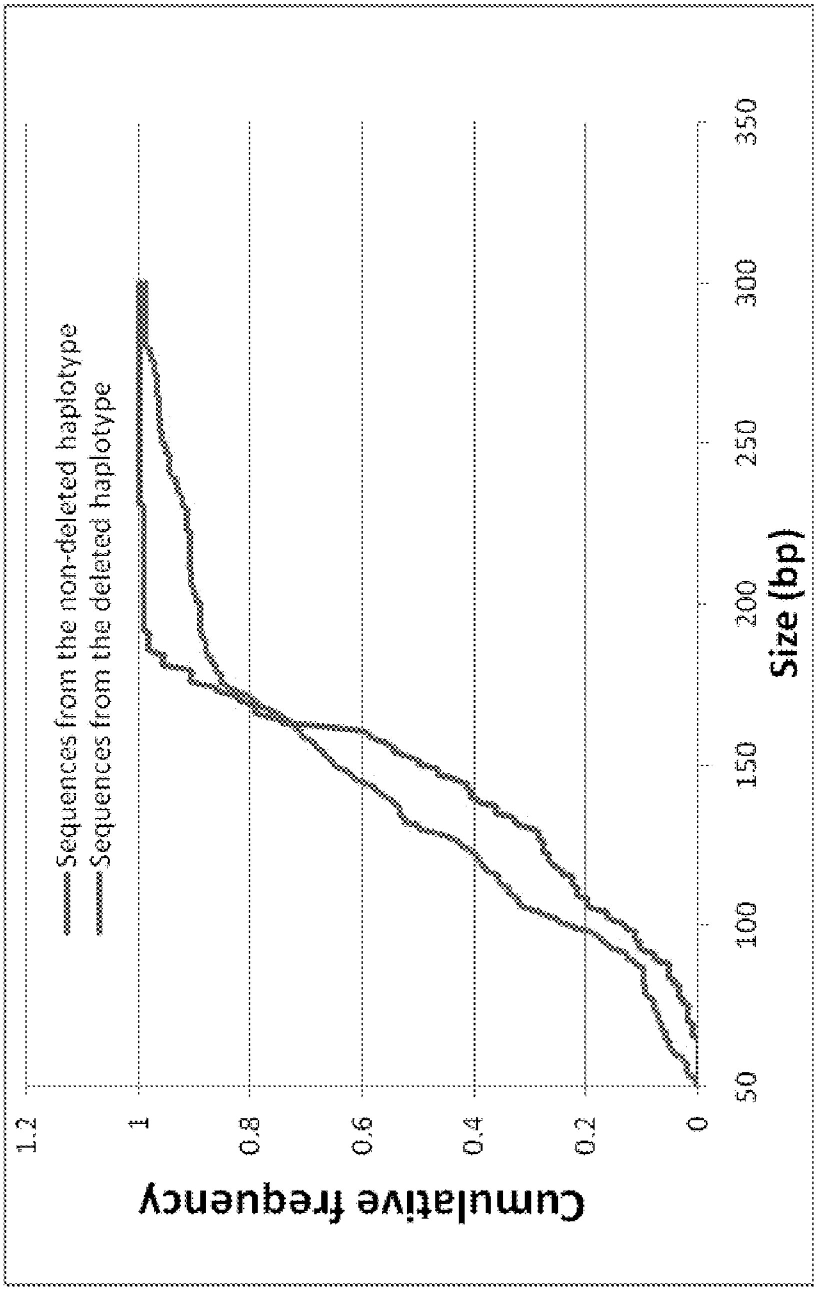
FIG. 25 shows a plot of cumulative frequency of plasma DNA against size for a region exhibiting loss of heterozygosity (LOH) in the tumor tissue according to embodiments of the present invention.

FIG. 25 shows a plot of cumulative frequency of plasma DNA against size for a region exhibiting LOH in the tumor tissue according to embodiments of the present invention. The X-axis is the size of a fragment in base pairs. The Y-axis is the percentage of fragments have a size below the value on the X-axis. The sequences from the non-deleted haplotype had more rapid increase and higher cumulative frequency below the size of 170 bp when compared with the sequences from the deleted haplotype. This indicates that short DNA fragments from the non-deleted haplotype were more abundant. This is consistent with the prediction above because of the contribution of the short tumor-derived DNA from the non-deleted haplotype.

In one embodiment, the difference in size distribution can be quantified by the difference in the cumulative frequencies of the two populations of DNA molecules. We define ΔQ as the difference of the cumulative frequencies of the two populations. $\Delta Q = Q_{non\text{-}deleted} - Q_{deleted}$, where $Q_{non\text{-}deleted}$ represents the cumulative frequency for sequenced DNA fragments coming from the non-deleted haplotype; and $Q_{deleted}$ represents the cumulative frequency for sequenced DNA fragments coming from the deleted haplotype.

Figure 26:
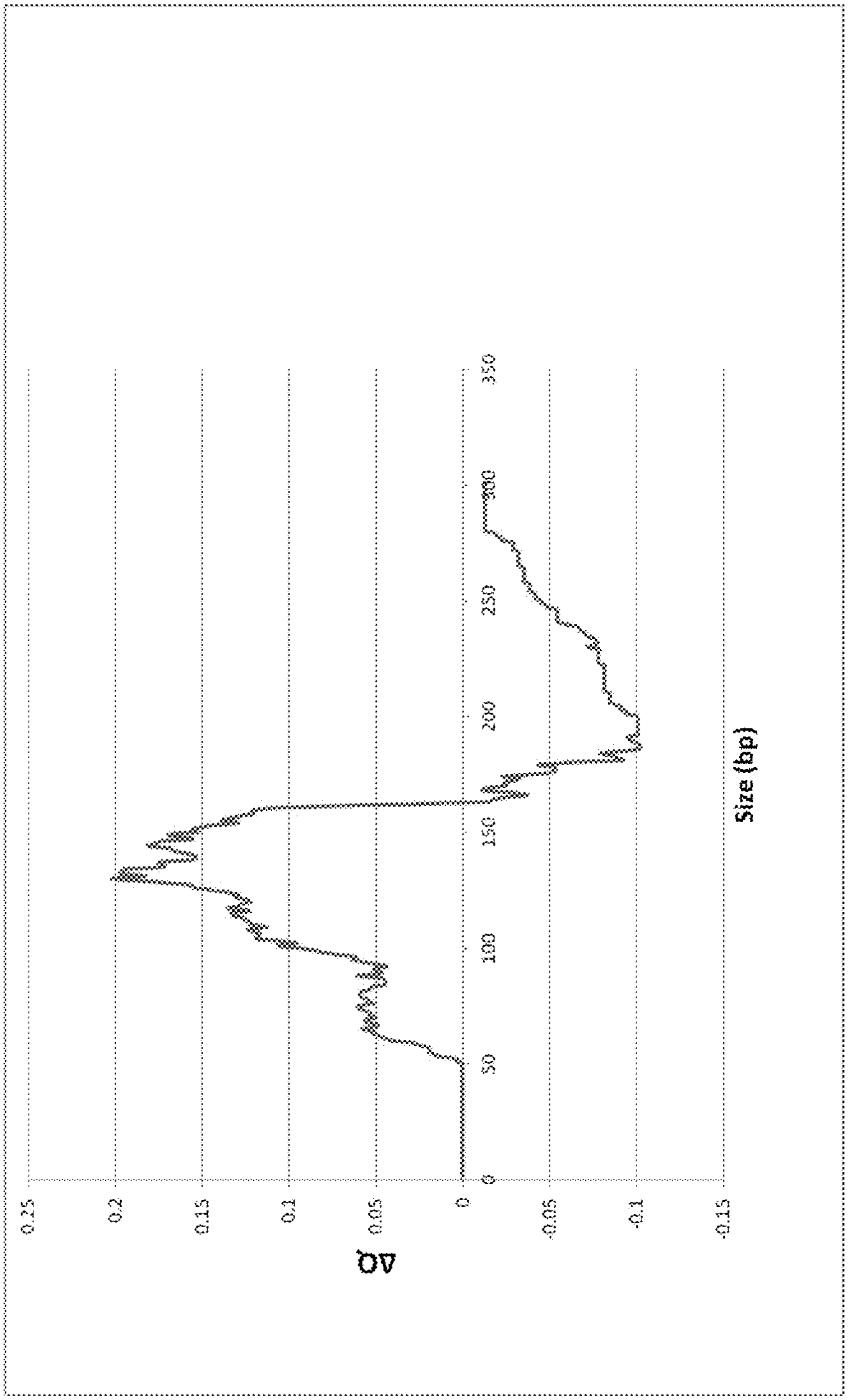
FIG. 26 shows ΔQ against the size of sequenced plasma DNA for the LOH region. ΔQ reaches 0.2 at the size of 130 bp according to embodiments of the present invention.

FIG. 26 shows ΔQ against the size of sequenced plasma DNA for the LOH region. ΔQ reaches 0.2 at the size of 130 bp according to embodiments of the present invention. This indicates that using 130 bp as a cutoff for defining short DNA is optimal, for use in the equations above. Using this cutoff, short DNA molecules are 20% more abundant in the population from the non-deleted haplotype when compared with the population from the deleted haplotype. This percentage difference (or similarly derived value) can then be compared with a threshold value derived from individuals without cancer, For the region with chromosomal amplification, one haplotype was duplicated in the tumor tissue (the amplified haplotype). Because an extra amount of the short tumor-derived DNA molecules from this amplified haplotype would be released into the plasma, the size distribution for the fragments from the amplified haplotype would be shorter than the size distribution for the fragments from the non-amplified haplotype. Similar to the LOH scenario, the difference in the size distributions can be determined by plotting the cumulative frequencies of fragments against the size of DNA fragments. The population of DNA with the shorter size distribution would have more abundant short DNA and hence a more rapid increase in the cumulative frequency at the short end of the size spectrum.

Figure 27:
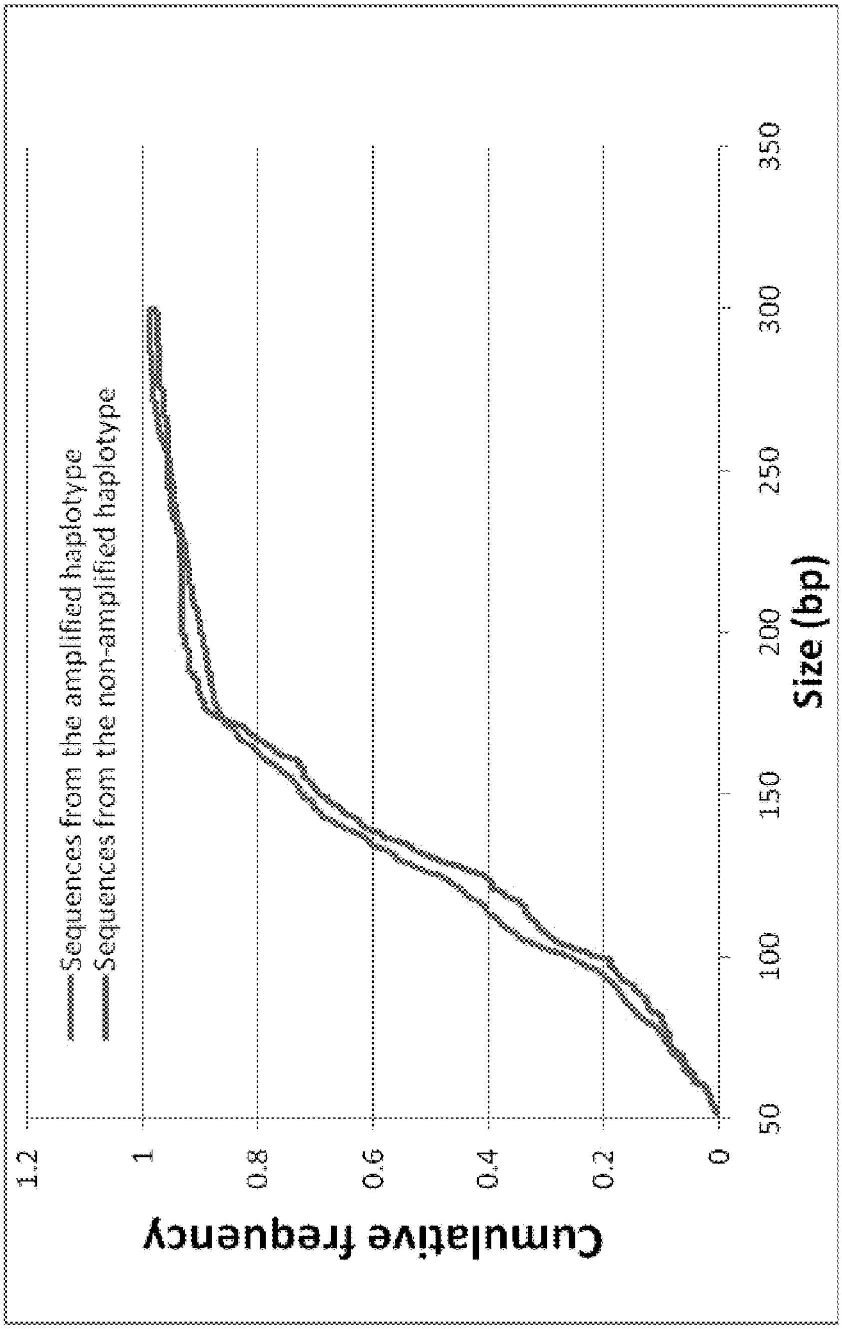
FIG. 27 shows a plot of cumulative frequency of plasma DNA against size for a region with chromosomal duplication in the tumor tissue according to embodiments of the present invention.

FIG. 27 shows a plot of cumulative frequency of plasma DNA against size for a region with chromosome duplication in the tumor tissue according to embodiments of the present invention. The sequences from the amplified haplotype had more rapid increase and higher cumulative frequency below the size of 170 bp when compared with the sequences from the non-amplified haplotype. This indicates that short DNA fragments from the amplified haplotype were more abundant. This is consistent with the prediction shown below because a larger number of short tumor-derived DNA were derived from the amplified haplotype.

Similar to the LOH scenario, the difference in size distribution can be quantified by the difference in the cumulative frequencies of the two populations of DNA molecules. We define ΔQ as the difference of the cumulative frequencies of the two populations. $\Delta Q = Q_{amplified} - Q_{non\text{-}amplified}$, where $Q_{amplified}$ represents the cumulative frequency for sequenced DNA fragments coming from the amplified haplotype; and $Q_{non\text{-}amplified}$ represents the cumulative frequency for sequenced DNA fragments coming from the non-amplified haplotype.

Figure 28:
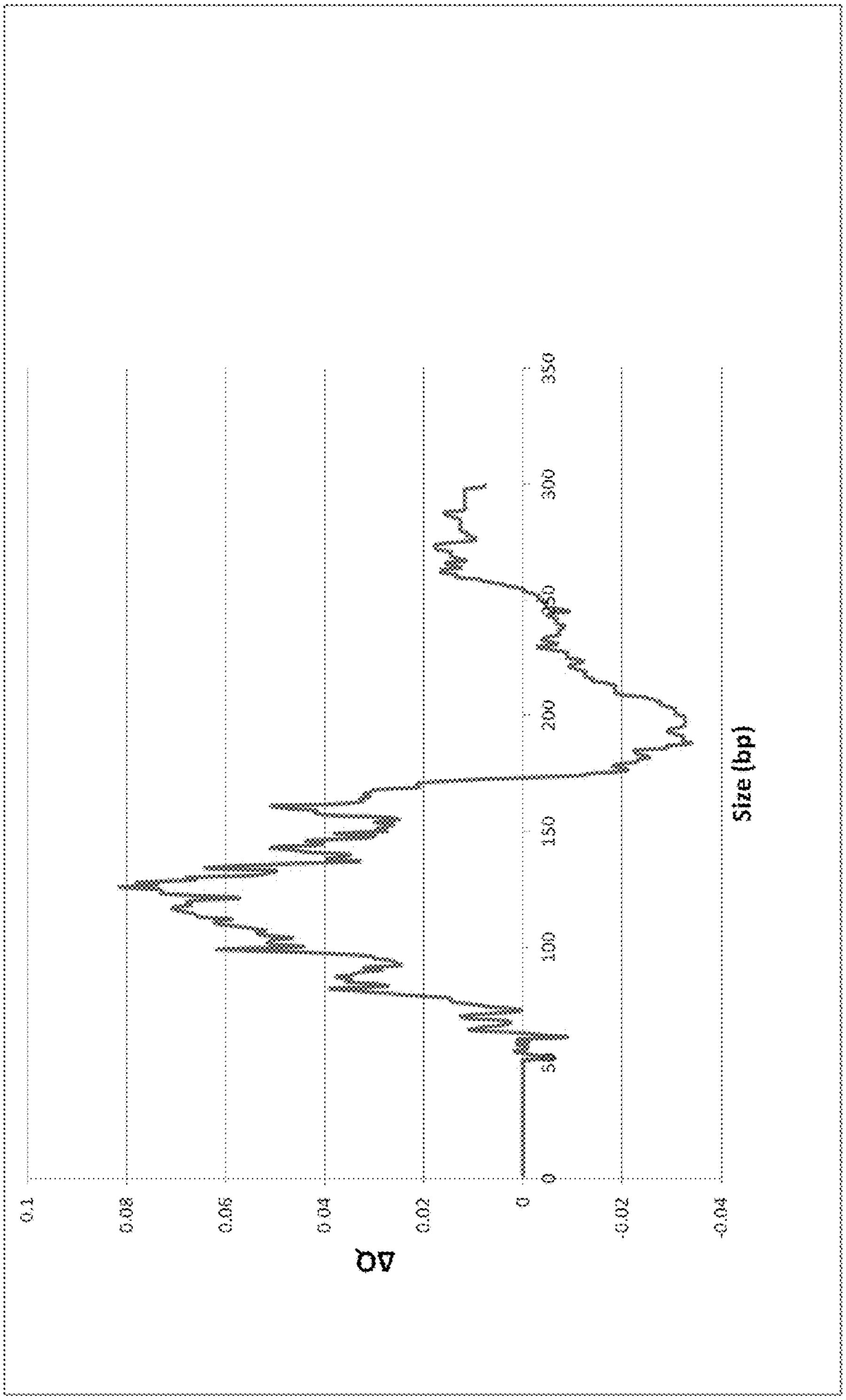
FIG. 28 shows ΔQ against the size of sequenced plasma DNA for the amplified region according to embodiments of the present invention.

FIG. 28 shows ΔQ against the size of sequenced plasma DNA for the amplified region according to embodiments of the present invention. ΔQ reached 0.08 at the size of 126 bp according to embodiments of the present invention. This indicates that using 126 bp as a cutoff for defining short DNA, short DNA molecules are 8% more abundant in the population from the amplified haplotype when compared with the population from the non-amplified haplotype.

D. Additional Techniques

In other embodiments, sequence-specific techniques may be used. For example, oligonucleotides may be designed to hybridize to fragments of a particular region. The oligonucleotides could then be counted, in a similar fashion as the sequenced tag counts. This method may be used for cancers that exhibit particular aberrations.

VIII. COMPUTER SYSTEM

Any of the computer systems mentioned herein may utilize any suitable number of subsystems. Examples of such subsystems are shown in FIG. 9 in computer apparatus 900. In some embodiments, a computer system includes a single computer apparatus, where the subsystems can be the components of the computer apparatus. In other embodiments, a computer system can include multiple computer apparatuses, each being a subsystem, with internal components.

Figure 29:
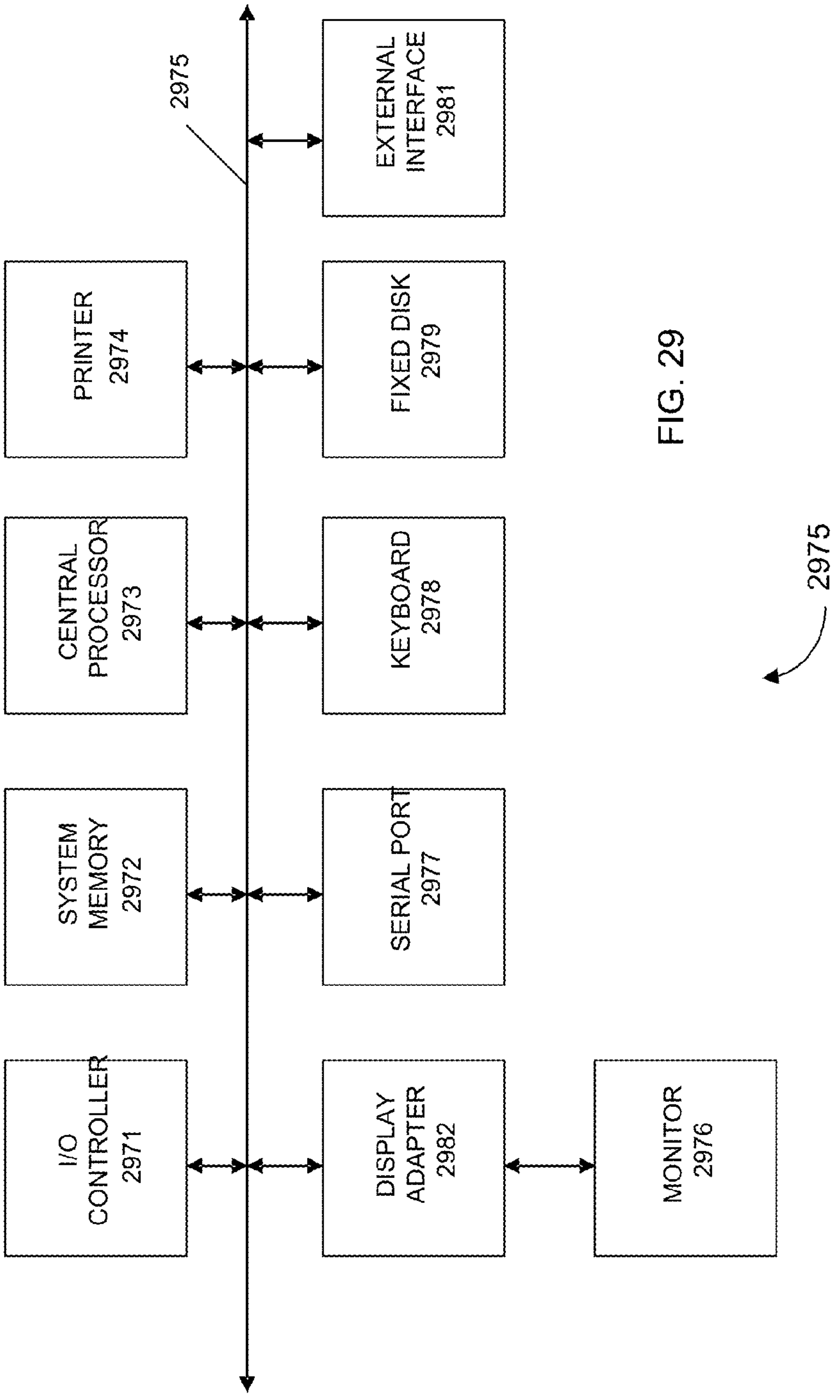
FIG. 29 shows a block diagram of an example computer system 900 usable with system and methods according to embodiments of the present invention.

The subsystems shown in FIG. 29 are interconnected via a system bus 2975. Additional subsystems such as a printer 2974, keyboard 2978, fixed disk 2979, monitor 2976, which is coupled to display adapter 2982, and others are shown. Peripherals and input/output (I/O) devices, which couple to I/O controller 2971, can be connected to the computer system by any number of means known in the art, such as serial port 2977. For example, serial port 2977 or external interface 2981 (e.g. Ethernet, Wi-Fi, etc.) can be used to connect computer system 2900 to a wide area network such as the Internet, a mouse input device, or a scanner. The interconnection via system bus 2975 allows the central processor 2973 to communicate with each subsystem and to control the execution of instructions from system memory 2972 or the fixed disk 2979, as well as the exchange of information between subsystems. The system memory 2972 and/or the fixed disk 2979 may embody a computer readable medium. Any of the values mentioned herein can be output from one component to another component and can be output to the user.

A computer system can include a plurality of the same components or subsystems, e.g., connected together by external interface 2981 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. All patents, patent applications, publications, and descriptions mentioned above are herein incorporated by reference in their entirety for all purposes. None is admitted to be prior art.

What is claimed is:

1. A method of analyzing a biological sample of an organism, the biological sample including nucleic acid molecules originating from normal cells and potentially from cells associated with cancer, wherein at least some of the nucleic acid molecules are cell-free in the biological sample, the method comprising:

identifying, by a computer system, a plurality of non-overlapping chromosomal regions of the organism, wherein each of the plurality of non-overlapping chromosomal regions includes a plurality of loci and is of predetermined length specified by the computer system before analysis of the biological sample, the predetermined length being between 100 kilobases and 50 megabases;

obtaining the biological sample of the organism, wherein the organism is not known to have a tumor;

using sequencing or sequence-specific probes on a plurality of nucleic acid molecules in the biological sample of the organism to obtain sequenced reads;

receiving the sequenced reads at the computer system;

identifying, by the computer system, a location of each of the plurality of nucleic acid molecules in a reference genome corresponding to the organism using the sequenced reads, the plurality of nucleic acid molecules including cell-free nucleic acid molecules, wherein the using sequencing or the sequence-specific probes provides sequenced reads located within the plurality of non-overlapping chromosomal regions in the reference genome;

for each of the plurality of non-overlapping chromosomal regions:

identifying a respective group of nucleic acid molecules among the plurality of nucleic acid molecules as being from the chromosomal region based on the identified locations, the respective group including at least one nucleic acid molecule located at each of the plurality of loci of the chromosomal region;

calculating, with a computer system, a respective value of the respective group of nucleic acid molecules, the respective value defining a property of the nucleic acid molecules of the respective group; and using the respective value and a respective reference value to determine a classification of whether the chromosomal region exhibits a deletion or an amplification;

determining an amount of chromosomal regions classified as exhibiting a deletion or amplification, the amount of chromosomal regions being (i) a number of the chromosomal regions classified as exhibiting a deletion or an amplification, or (ii) a total length of the chromosomal regions classified as exhibiting a deletion or an amplification; and analyzing the amount of chromosomal regions against a threshold value to determine a classification of whether the organism has cancer, the classification including that the organism has cancer when the amount of chromosomal regions is greater than the threshold value, the threshold value being determined based on samples having cancer and samples not having cancer.

2. The method of claim 1, wherein the analyzing the amount of chromosomal regions against the threshold value provides a stage of cancer in the organism or a size of the tumor.

3. The method of claim 1, wherein the organism is classified as having cancer, and wherein the cells associated with cancer derive from a malignant tumor and/or from a premalignant lesion.

4. The method of claim 1, wherein the amount of chromosomal regions corresponds to a number of chromosomal regions that exhibit a deletion or an amplification.

5. The method of claim 1, wherein the using the respective value and the respective reference value includes:

determining a difference or a ratio between the respective value and the respective reference value, and wherein the determining the classification includes analyzing the difference or the ratio against at least one threshold value.

6. The method of claim 5, further comprising:

determining a respective amount of deletion or amplification using the difference or the ratio for each chromosomal region identified as exhibiting a deletion or an amplification; and accumulating the respective amounts to obtain the amount of chromosomal regions.

7. The method of claim 1, wherein a first respective value corresponds to a statistical value of a size distribution of the nucleic acid molecules of a first respective group, and the respective reference value corresponds to a statistical value of a size distribution of nucleic acid molecules of a reference chromosomal region.

8. The method of claim 1, wherein a first respective value of a first respective group of nucleic acid molecules corresponds to a number of nucleic acid molecules located at the plurality of loci of a first chromosomal region, and wherein the respective reference value corresponds to a number of nucleic acid molecules located at a plurality of loci of a reference chromosomal region.

9. The method of claim 8, further comprising:

for each of the chromosomal regions:

calculating a ratio to determine a fractional concentration of cancer DNA in the biological sample for the chromosomal region.

10. The method of claim 9, further comprising:

determining the fractional concentration of cancer DNA in the biological sample at a plurality of times for each of the chromosomal regions; and using the fractional concentrations at the plurality of times to diagnose, stage, prognosticate, or monitor progress of a level of cancer in the organism.

11. The method of claim 1, further comprising:

using classifications of each of the chromosomal regions at a plurality of times to determine a progress of deletions or amplification for the chromosomal regions in the organism.

12. The method of claim 11, wherein the classifications are numerical values that reflect a difference between the respective value and the respective reference value for each chromosomal region at each time.

13. The method of claim 1, further comprising:

at each of a plurality of times:

determining an amount of chromosomal regions classified as exhibiting a deletion or amplification; and wherein the amounts of chromosomal regions are used to monitor a progress of a cancer in the organism.

14. The method of claim 1, wherein the respective reference values are obtained from a group of nucleic acid molecules identified as being from a reference chromosomal region that does not exhibit a deletion or amplification at a time the group of nucleic acid molecules were obtained.

15. The method of claim 1, further comprising:

determining first and second haplotypes for normal cells of the organism at a first chromosomal region of the chromosomal regions, the first chromosomal region including a first plurality of loci, wherein the first and second haplotypes are heterozygous at each of the first plurality of loci, wherein the respective value of the first chromosomal region is obtained from a first group of nucleic acid molecules identified as being from the first haplotype, and wherein the respective reference value for the first chromosomal region is obtained from a second group of nucleic acid molecules identified as being from the second haplotype.

16. The method of claim 1, wherein the plurality of non-overlapping chromosomal regions span the reference genome corresponding to the organism.

17. The method of claim 1, wherein each locus of the plurality of loci of each chromosomal region is at least 500 bases apart from another locus of the plurality of loci.

18. A computer program product comprising a computer readable medium storing a plurality of instructions for controlling a computer system to perform an operation for analyzing a biological sample of an organism for chromosomal deletions or amplifications associated with cancer, the operation comprising:

identifying a plurality of non-overlapping chromosomal regions of the organism, each chromosomal region including a plurality of loci, wherein each of the plurality of non-overlapping chromosomal regions is of predetermined length specified by the computer system before analysis of the biological sample, the predetermined length being between 100 kilobases and 50 megabases;

for each of a plurality of nucleic acid molecules in the biological sample of the organism:

identifying a location of each of the plurality of nucleic acid molecules in a reference genome corresponding to the organism, the plurality of nucleic acid molecules including cell-free nucleic acid molecules;

for each of the plurality of non-overlapping chromosomal regions:

identifying a respective group of nucleic acid molecules among the plurality of nucleic acid molecules as being from the chromosomal region based on the identified locations, the respective group including at least one nucleic acid molecule located at each of the plurality of loci of the chromosomal region;

calculating a respective value of the respective group of nucleic acid molecules, the respective value defining a property of the nucleic acid molecules of the respective group;

using the respective value and a respective reference value to determine a classification of whether the chromosomal region exhibits a deletion or an amplification; and determining an amount of chromosomal regions classified as exhibiting a deletion or amplification, the amount of chromosomal regions being (i) a number of the chromosomal regions classified as exhibiting a deletion or an amplification, or (ii) being a total length of the chromosomal regions classified as exhibiting a deletion or an amplification; and analyzing the amount of chromosomal regions against a threshold value to determine a classification of whether the organism has cancer, the classification including that the organism has cancer when the amount of chromosomal regions is greater than the threshold value, the threshold value being determined based on samples having cancer and samples not having cancer.

19. The method of claim 1, wherein the method provides a screening process for screening a healthy population for cancer.

20. The method of claim 1, wherein the biological sample includes plasma, serum, urine, or saliva.

21. The method of claim 1, wherein the plurality of non-overlapping chromosomal regions are at predetermined locations, and wherein the predetermined length and the predetermined location for each of the plurality of the non-overlapping chromosomal regions are specified in a memory of the computer system for use in analyzing a plurality of samples.

22. The method of claim 1, further comprising:

enriching the biological sample for nucleic acid molecules originating from cells associated with cancer.

23. The method of claim 1, further comprising:

using capturing probes to preferentially capture nucleic acid molecules within the plurality of non-overlapping chromosomal regions of the organism, the plurality of non-overlapping chromosomal regions corresponding to a particular type of cancer.

24. The method of claim 1, wherein the plurality of non-overlapping chromosomal regions comprises at least 3,000 regions, and the plurality of nucleic acid molecules comprises at least 15,000 nucleic acid molecules.

25. The method of claim 1, wherein the amount of chromosomal regions corresponds to a total length of the chromosomal regions classified as exhibiting a deletion or an amplification.

26. The method of claim 1, wherein the obtaining the sequenced reads includes performing random sequencing, the method further comprising:

after a treatment is provided to the organism based on the amount of chromosomal regions being greater than the threshold value, obtaining another biological sample of the organism;

providing sequence-specific probes corresponding to at least a portion of the chromosomal regions classified as exhibiting a deletion or an amplification; and using the sequence-specific probes on another plurality of nucleic acid molecules in the other biological sample of the organism to obtain a new set of sequenced reads for use in determining a number of the at least a portion of the chromosomal regions that are still classified as exhibiting the deletion or the amplification.

27. The method of claim 26, further comprising:

providing the treatment to the organism based on the amount of chromosomal regions being greater than the threshold value.

* * * * *